US012162908B2

(12) United States Patent
Luginbuhl et al.

(10) Patent No.: US 12,162,908 B2
(45) Date of Patent: *Dec. 10, 2024

(54) GENETICALLY ENCODED POLYPEPTIDE FOR AFFINITY CAPTURE AND PURIFICATION OF BIOLOGICS

(71) Applicant: Donaldson Company, Inc., Bloomington, MN (US)

(72) Inventors: Kelli M. Luginbuhl, Durham, NC (US); Ashutosh Chilkoti, Durham, NC (US)

(73) Assignee: Donaldson Company, Inc., Bloomington, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/346,456

(22) Filed: Jul. 3, 2023

(65) Prior Publication Data

US 2024/0002448 A1    Jan. 4, 2024

Related U.S. Application Data

(63) Continuation of application No. 17/349,558, filed on Jun. 16, 2021, now Pat. No. 11,739,126, which is a continuation of application No. 17/268,314, filed as application No. PCT/US2019/046607 on Aug. 15, 2019.

(60) Provisional application No. 62/764,833, filed on Aug. 16, 2018.

(51) Int. Cl.
  *C07K 14/005*    (2006.01)
  *C07K 1/14*    (2006.01)

(52) U.S. Cl.
  CPC ............ *C07K 14/005* (2013.01); *C07K 1/145* (2013.01); *C07K 2319/705* (2013.01)

(58) Field of Classification Search
  None
  See application file for complete search history.

(56) References Cited

U.S. PATENT DOCUMENTS

| | | | |
|---|---|---|---|
| 5,283,173 A | 2/1994 | Fields et al. | |
| 5,468,614 A | 11/1995 | Fields et al. | |
| 6,410,300 B1 | 6/2002 | Samulski et al. | |
| 6,582,926 B1 | 6/2003 | Chilkoti | |
| 6,852,834 B2 | 2/2005 | Chilkoti | |
| 9,616,138 B1 | 4/2017 | Iglesias et al. | |
| 10,385,115 B2 | 8/2019 | Chilkoti et al. | |
| 10,633,662 B2 * | 4/2020 | Pillay | C12N 15/113 |
| 11,015,174 B2 | 5/2021 | Lock et al. | |
| 11,021,689 B2 | 6/2021 | Brument | |
| 11,155,584 B2 | 10/2021 | Chilkoti et al. | |
| 11,156,608 B2 | 10/2021 | Tsourkas et al. | |
| 11,591,576 B2 | 2/2023 | Luginbuhl et al. | |
| 11,739,126 B2 * | 8/2023 | Luginbuhl | G01N 33/53 435/235.1 |
| 2003/0149237 A1 | 8/2003 | Vernet et al. | |
| 2003/0194704 A1 | 10/2003 | Penn et al. | |
| 2005/0255554 A1 | 11/2005 | Chilkoti | |
| 2011/0039776 A1 | 2/2011 | Chilkoti | |
| 2012/0121709 A1 | 5/2012 | Chilkoti et al. | |
| 2012/0122153 A1 | 5/2012 | Bedzyk et al. | |
| 2013/0281624 A1 | 10/2013 | Chilkoti et al. | |
| 2015/0112022 A1 | 4/2015 | Chilkoti et al. | |
| 2018/0037609 A1 | 2/2018 | Chilkoti et al. | |
| 2018/0327752 A1 | 11/2018 | Pillay et al. | |
| 2019/0048039 A1 | 2/2019 | Chen et al. | |
| 2019/0055523 A1 | 2/2019 | Lock et al. | |
| 2019/0282656 A1 | 9/2019 | Mackay et al. | |
| 2019/0328662 A1 | 10/2019 | Chilkoti et al. | |
| 2020/0017557 A1 | 1/2020 | Chilkoti et al. | |
| 2021/0261626 A1 | 8/2021 | Luginbuhl et al. | |
| 2021/0340186 A1 | 11/2021 | Luginbuhl et al. | |
| 2022/0010288 A1 | 1/2022 | Luginbuhl et al. | |
| 2022/0098248 A1 | 3/2022 | Chilkoti et al. | |
| 2023/0099707 A1 | 3/2023 | Luginbuhl et al. | |
| 2023/0340426 A1 | 10/2023 | Luginbuhl et al. | |
| 2023/0348863 A1 | 11/2023 | Luginbuhl et al. | |

(Continued)

FOREIGN PATENT DOCUMENTS

| | | |
|---|---|---|
| CN | 104725515 A | 6/2015 |
| CN | 105175554 A | 12/2015 |
| WO | WO-2004113494 A2 | 12/2004 |

(Continued)

OTHER PUBLICATIONS

Alberti et al., "A User's Guide for Phase Separation Assays with Purified Proteins," Journal of Molecular Biology, Jun. 18, 2018, pp. 4806-4820, Entire Document; https://doi.org/10.1016/j.jmb.2018.06.038.

Balcerak et al., "RNA-protein interactions: disorder, moonlighting and junk contribute to eukaryotic complexity". Open Biology. Jun. 19, 2019; 9(6): pp. 1-13.

Baou et al., "TIS11 family proteins and their roles in post-transcriptional gene regulation". Journal of Biomedicine and Biotechnology. Jan. 1, 2009; 29: 11 pages.

Brennan et al., "HuR and mRNA stability. Cellular and Molecular Life Sciences CMLS". Feb. 2001; 58: 266-77.

Brise et al., "Comparative structure and function analysis of the RIG-I-like receptors: RIG-I and MDA5". Frontiers in immunology. Jul. 17, 2019; 10: pp. 1-27.

(Continued)

*Primary Examiner* — Agnieszka Boesen
(74) *Attorney, Agent, or Firm* — COOLEY LLP

(57) ABSTRACT

The invention relates to genetically encoded fusion proteins comprised of a capture component that binds a target with high affinity and a peptide polymer, such as elastin-like polypeptides, that display phase behavior and can be used for purification. The invention further relates to methods for optimizing capture fusion proteins for individual biologic targets such that phase separation occurs under desirable conditions, such as at room temperature, lower concentrations of salt, and/or at suitable pH ranges and optimized capture domains and polypeptides with phase behavior that have been identified by the optimization methods.

37 Claims, 19 Drawing Sheets

Specification includes a Sequence Listing.

(56) References Cited

U.S. PATENT DOCUMENTS

| | | |
|---|---|---|
| 2023/0391832 A1 | 12/2023 | Luginbuhl |
| 2024/0018202 A1 | 1/2024 | Votaw |

FOREIGN PATENT DOCUMENTS

| | | |
|---|---|---|
| WO | WO-2006110292 A2 | 10/2006 |
| WO | WO-2013111110 A2 | 8/2013 |
| WO | WO-2014026054 A2 | 2/2014 |
| WO | WO-2016154530 A1 | 9/2016 |
| WO | WO-2018057847 A1 | 3/2018 |
| WO | WO-2020037100 A1 | 2/2020 |
| WO | WO-2021106882 A1 | 6/2021 |
| WO | WO-2021168270 A1 | 8/2021 |
| WO | WO-2021168276 A1 | 8/2021 |
| WO | WO-2021178481 A1 | 9/2021 |
| WO | WO-2021178483 A2 | 9/2021 |
| WO | WO-2022178537 A1 | 8/2022 |
| WO | WO-2023212694 A2 | 11/2023 |
| WO | WO-2024015853 A2 | 1/2024 |

OTHER PUBLICATIONS

Carballo et al., "Feedback inhibition of macrophage tumor necrosis factor-α production by tristetraprolin". Science. Aug. 14, 1998; 281(5379): 1001-5.

Corley et al., "How RNA-binding proteins interact with RNA: molecules and mechanisms". Molecular cell. Apr. 2, 2020; 78(1): 9-29.

Costa et al., "Fusion tags for protein solubility, purification and immunogenicity in *Escherichia coli*: the novel Fh8 system". Frontiers in microbiology. Feb. 19, 2014; 5: pp. 1-20.

De Franco et al., "Exploring the suitability of RanBP2-type Zinc Fingers for RNA-binding protein design". Scientific reports. Feb. 21, 2019; 9(1): pp. 1-13.

Dickson et al., "Ribonuclease inhibitor: structure and function", Prog Nucleic Acid Res Mol Biol, 2005; 80: 349-374.

Ehrlich et al., "Isolation of an active heavy-chain variable domain from a homogeneous rabbit antibody by cathepsin B digestion of the aminoethylated heavy chain," Biochemistry, Aug. 1, 1980, vol. 19, No. 17, pp. 4091-4096.

Elbaum-Garfinkle et al., "The disordered P granule protein LAF-1 drives phase separation into droplets with tunable viscosity and dynamics". Proceedings of the National Academy of Sciences. Jun. 9, 2015; 112(23): 7189-94.

Hochman et al., "Folding and interaction of subunits at the antibody combining site," Biochemistry, Jun. 1, 1976, vol. 15, No. 12, pp. 2706-2710.

Inbar et al., "Localization of antibody-combining sites within the variable portions of heavy and light chains". Proceedings of the National Academy of Sciences. Sep. 1972; 69(9): 2659-62.

International Search Report and Written Opinion for Application No. PCT/US22/70727, mailed on Jul. 5, 2022, 12 pages.

International Search Report and Written Opinion for PCT Application No. PCT/US2023/066363 dated Oct. 6, 2023, 12 pages.

Invitation to Pay Fee for International Application No. PCT/US2022/070727 dated May 4, 2022, 2 pages.

Jarvelin et al., "The new (dis) order in RNA regulation". Cell Communication and Signaling. Dec. 2016; 14(1): 1-22.

Kobori et al., "Heat-labile alkaline phosphatase from Antarctic bacteria: rapid 5′ end-labeling of nucleic acids". Proceedings of the National Academy of Sciences. Nov. 1984; 81(21): 6691-5.

Kuroyanagi "Fox-1 family of RNA-binding proteins". Cellular and Molecular Life Sciences. Dec. 2009; 66: 3895-907.

Leacock et al., "MEG-1 and MEG-2 are embryo-specific P-granule components required for germline development in Caenorhabditis elegans". Genetics. Jan. 1, 2008; 178(1): 295-306.

Luo et al., "P-bodies: composition, properties, and functions". Biochemistry. Jan. 30, 2018;57(17): 2424-31.

Luo et al., "The D1 and D12 subunits are both essential for the transcription termination factor activity of vaccinia virus capping enzyme". Journal of Virology. Jun. 1995; 69(6): 3852-6.

Luo et al., "Structural insights into RNA recognition by RIG-I". Cell. Oct. 14, 2011; 147(2): 409-22.

Mazan-Mamczarz et al., "Identification of a signature motif in target mRNAs of RNA-binding protein AUF1". Nucleic acids research. Jan. 1, 2009; 37(1): 204-14.

Mazan-Mamczarz et al., "Post-transcriptional gene regulation by HuR promotes a more tumorigenic phenotype". Oncogene. Oct. 2008; 27(47): 6151-63.

Otsuka et al., "Emerging evidence of translational control by AU-rich element-binding proteins". Frontiers in Genetics. May 2, 2019; 10: 10 pages.

Rehwinkel et al., "RIG-I-like receptors: their regulation and roles in RNA sensing". Nature Reviews Immunology. Sep. 2020; 20(9): 537-51.

Shotwell et al., The potential of engineered eukaryotic RNA-binding proteins as molecular tools and therapeutics. Wiley Interdisciplinary Reviews: RNA. Jan. 2020;11(1): pp. 1-21.

Shuman et al., "Purification and characterization of a GTP-pyrophosphate exchange activity from vaccinia virions. Association of the GTP-pyrophosphate exchange activity with vaccinia mRNA guanylyltransferase. RNA (guanine-7-) methyltransferase complex (capping enzyme)". Journal of Biological Chemistry. Dec. 10, 1980; 255(23): 11588-98.

Simon et al., "Engineered ribonucleoprotein granules inhibit translation in protocells". Molecular cell. Jul. 11, 2019; 75(1): 66-75.

Summerford et al., "AAVR: a multi-serotype receptor for AAV". Molecular Therapy. Apr. 1, 2016; 24(4): 663-6.

Thandapani et al., "Defining the RGG/RG motif". Molecular cell. Jun. 6, 2013; 50(5): 613-23.

UniProt Consortium. "P01730 • CD4_HUMAN", CD4-T-cell surface glycoprotein CD4—*Homo sapiens* (Human) I UniProtKB I UniProt, [Internet: retrieved Oct. 4, 2023], 11 pages Available from: https://www.uniprot.org/uniprotkb/P01730/entry.

UniProt Consortium. "Q70AB8_STAAU", spa-Protein A—*Staphylococcus aureus* I UniProtKB I UniProt, [Internet: retrieved Oct. 4, 2023], 6 pages. Available from: https://www.uniprot.org/uniprotkb/Q70AB8/entry.

UniProtKB Accession No. A0A653CGZ9 "Uncharacterized protein" Sep. 29, 2021 [online]. [Retrieved on Sep. 18, 2023]. Retrieved from the internet: URL: https://rest.uniprot.org/unisave/A0A653CGZ9?format=txt&versions=8; entire document, residues 2172-2214.

Valkov et al. "Structure of the Dcp2-Dcp1 mRNA-decapping complex in the activated conformation". Nature Structural & Molecular Biology. Jun. 2016; 23(6): 574-9.

Varadi et al., "Functional advantages of conserved intrinsic disorder in RNA-binding proteins". PloS one. Oct. 6, 2015; 10(10): pp. 1-16.

Vasudevan et al., "AU-rich-element-mediated upregulation of translation by FXR1 and Argonaute 2". Cell. Mar. 23, 2007; 128(6): 1105-18.

Wu et al., "Single-molecule dynamics of the P granule scaffold MEG-3 in the Caenorhabditis elegans zygote". Molecular biology of the cell. Feb. 1, 2019; 30(3): 333-45.

Zeke et al., "Deep structural insights into RNA-binding disordered protein regions". Wiley Interdisciplinary Reviews: RNA. Sep. 2022; 13(5): pp. 1-20.

Zhang et al., "Adeno-associated virus 2 bound to its cellular receptor AAVR". Nature Microbiology. Apr. 2019; 4(4): 675-82.

Zhang et al., "Divergent engagements between adeno-associated viruses with their cellular receptor AAVR". Nature Communications. Aug. 21, 2019; 10(1): pp. 1-11.

Zhao et al., "Expanding RNA binding specificity and affinity of engineered PUF domains". Nucleic acids research. May 18, 2018; 46(9): 4771-82.

Balu et al., "Resilin-mimetics as a smart biomaterial platform for biomedical applications," Nature Comm, 2021, 12:149, 15 pages.

Bhattacharya et al., "Impact of genetic variation on three dimensional structure and function of proteins," PLoS ONE 12(3): 2017, pp. 1-22.

Bork, P. et al., "Go hunting in sequence databases but watch out for the traps," Trends in Genetics, 12(10):425-427, 1996.

(56) References Cited

OTHER PUBLICATIONS

Bork, P., "Powers and pitfalls in sequence analysis: the 70% hurdle," Genome Res., 10: 398-400, 2000.
Brenner, S. E., "Errors in genome annotation". Trends in Genetics. Apr. 1, 1999; 15(4): 132-3.
Christensen et al., "Fusion order controls expression level and activity of elastin-like polypeptide fusion proteins," Protein Science, 2009, vol. 18, 1377-1387.
Christensen, et al., "Predicting Transition Temperatures of Elastin-Like Polypeptide Fusion Proteins." Biomacromolecules (2013); 14(5): 1514-1519.
Doerks et al., "Protein annotation: detective work for function prediction". Trends in Genetics. Jun. 1, 1998; 14(6): 248-50.
Dzuricky et al., "Convergence of artificial protein polymers and intrinsically disordered proteins," Biochemistry, 2018, 57: 2405-2414.
Dzuricky et al., "De novo engineering of intracellular condensates using artificial disordered proteins," Nature Chemistry, Sep. 2020, vol. 12, pp. 814-825 (18 pages).
Extended European Search Report for European Application No. 19850360.9 dated Apr. 20, 2022, 12 pages.
Fenton et al., "Rheostat positions: A new classification of protein positions relevant to pharmacogenomics," Medicinal Chem Res, 2020, 29: 1133-1146.
Guo et al., "Protein tolerance to random amino acid change", Proc Natl Acad Sci USA. Jun. 22, 2004; 101(25): 9205-10. Epub Jun. 14, 2004.
Guo et al., "Rapid and simplified purification of recombinant adeno-associated virus," Journal of Virological Methods (2012) 183, 139-146.
Hassouneh et al., "Elastin-like Polypeptides as a Purification Tag for Recombinant Proteins," Curr Protoc Protein Sci. Aug. 2010; Chapter: Unit-6.11, 20 pages.
Hassouneh, W., et al., "Fusions of Elastin-like Polypeptides to Pharmaceutical Proteins," Methods in Enzymology, 2012, vol. 502, Chapter 9, pp. 215-237.
Heider et al., "Integrated Method for Purification and Single-Particle Characterization of Lentiviral Vector Systems by Size Exclusion Chromatography and Tunable Resistive Pulse Sensing," Mol Biotechnol (2017) 59:251-259.
Huang et al., "Silk-elastin-like protein biomaterials for the controlled delivery of therapeutics," Expert Opinion on Drug Delivery (2015) 12:5, 779-791.
International Preliminary Report on Patentability for International Application No. PCT/US2019/046607, mailed on Feb. 16, 2021, 10 pages.
International Search Report and Written Opinion of the International Searching Authority for International Application No. PCT/US2019/046607 dated Nov. 29, 2019, 13 pages.
International Search Report and Written Opinion of the International Searching Authority for International Application No. PCT/US2021/018805 dated Jul. 8, 2021, 13 pages.
International Search Report and Written Opinion of the International Searching Authority for International Application No. PCT/US2021/018812 dated Jul. 22, 2021, 14 pages.
Invitation to pay additional fees for International Application No. PCT/US2023/066363, dated Aug. 10, 2023, 2 pages.
International Preliminary Report on Patentability for International Application No. PCT/US2021/018805, mailed on Sep. 1, 2022, 9 pages.
International Preliminary Report on Patentability for International Application No. PCT/US2021/018812, mailed on Sep. 1, 2022, 9 pages.
International Preliminary Report on Patentability for International Application No. PCT/US2022/070727, mailed Aug. 31, 2023, 7 pages.
Kim et al., "Elastin-like polypeptide matrices for enhancing adeno-associated virus-mediated gene delivery to human neural stem cells," Gene Therapy, (2012) 19, 329-337.
Kowalczyk, T., et al., "Elastin-like polypeptides as a promising family of genetically-engineered protein based polymers." World Journal of Microbiology and Biotechnology (2014); 30(8): 2141-2152.
Kuna et al., "Molecular Size Modulates Pharmacokinetics, Biodistribution, and Renal Deposition of the Drug Delivery Biopolymer elastin-like polypeptide," Scientific Rep (2018) 8:7923, 12 pages.
MacEwan et al. Elastin-like polypeptides: biomedical applications of tunable biopolymers, Biopolymers (Pept Sci), 2010, 94: 60-77.
Merten et al., "Production of lentiviral vectors," Molecular Therapy—Methods & Clinical Development (2016) 3, 16017, 15 pages; doi:10.1038/mtm.2016.17.
Miller, A.D., "Cell-surface receptors for retroviruses and implications for gene transfer," Pnas USA, Oct. 1996, vol. 93, pp. 11407-11413.
Monfort and Koria, "Recombinant elastin based nanoparticles for targeted gene therapy," Gene Ther. Oct. 2017; 24(10): 610-620.
Ngo, J.T., et al., "Computational Complexity, Protein Structure Prediction, and The Levinthal Paradox," The Protein Folding Problem and Tertiary Structure Prediction, Merz et al., (ed.), Birkhauser, Boston, MA, 1994, pp. 491-495.
Ohainle et al., "A balancing act between primate lentiviruses and their receptor," PNAS, 2021, vol. 118, No. 20, e2104741118, 3 pages.
Pillay et al., "Adeno-associated Virus (AAV) Serotypes Have Distinctive Interactions with Domains of the Cellular AAV Receptor," J. Virol (2017) 91:e00891-17, 17 pages.
Pillay et al., "An essential receptor for adeno-associated virus infection," Nature, Feb. 2016, vol. 530, pp. 108-112, 17 pages.
Roberts et al., "Elastin-like polypeptides as models of intrinsically disordered proteins," FEBS Letters, 2015, 589: 2477-2486.
Skolnick J., et al., "From Genes to Protein Structure and Function: Novel Applications of Computational Approaches in The Genomic Era," Trends in Biotechnology, Jan. 2000, vol. 18, pp. 34-39.
Smith et al., "The challenges of genome sequence annotation or 'The devil is in the details,'" Nature Biotech., 15:1222-1223, 1997.
Sommerfelt et al., "Retrovirus receptors," J Gen Virol, 1999, 80: 3049-3064.
Teschner et al., "rAAV for Tumor Therapy Using Transcriptional and Translational Control of Suicide Gene Expression Purified by a Newly Developed Affinity Chromatography Based on the PKD Domains of AAVR," Molecular Therapy, Pharmacology/Toxicology Studies, Abstract 970, vol. 28, No. 4S1, Apr. 28, 2020, p. 422.
Teschner, K. E., "Optimization of rAAV mediated targeted suicide gene therapy, rAAV manufacturing and downstream processing," Dissertation, Universitat Bielefeld, 2019, 229 pages.
Tokuriki et al., "Stability effects of mutations and protein evolvability," Curr Opin Structural Biol, 2009, 19: 596-604.
Uniprot Accession No. P01130 (LDLR_HUMAN), Jul. 21, 1986, 40 pages, retrieved from https://www.uniprot.org/uniprot/P01130.txt.
Wells, James A, "Additivity of mutational effects in proteins", Biochemistry (1990); 29(37): 8509-8517.
Wu et al., "Single-step concentration and purification of adenoviruses by coxsackievirus-adenovirus receptor-binding capture and elastin-like polypeptide-mediated precipitation," Archives of Virology (2016) 161: 279-287.
Yeboah et al., "Elastin-Like Polypeptides: A Strategic Fusion Partner for Biologics," Biotechnology and Bioengineering, Aug. 2016, vol. 113, No. 8, pp. 1617-1627.
Gilroy et al., "Fusion of fibroblast growth factor 21 to a thermally responsive biopolymer forms an injectable depot with sustained anti-diabetic action," Journal of Controlled Release, May 2018, 277: 154-164.
Extended European Search Report for European Application No. EP21756728.8 dated Feb. 26, 2024, 10 pages.
Extended European Search Report for European Application No. EP21757068.8 dated Mar. 4, 2024, 13 pages.
Guo et al., "A novel elastin-like polypeptide drug carrier for cyclosporine A improves tear flow in a mouse model of Sjogren's Syndrome". J Control Release. 2018, vol. 292, p. 183-195.
International Search Report and Written Opinion for International Application No. PCT/US2023/070044 dated Feb. 15, 2024, 15 pages.

(56) References Cited

OTHER PUBLICATIONS

Kim et al., "AAVR-displaying interfaces: serotype-independent adeno-associated virus capture and local delivery systems". Molecular Therapy-Nucleic Acids. Dec. 6, 2019; 18: 432-43.

Nikolic et al., "Structural basis for the recognition of LDL-receptor family members by VSV glycoprotein". Nat Commun. 2018, vol. 9: 12 pages.

Ruff et al., Advances in Understanding Stimulus Responsive Phase Behavior of Intrinsically Disordered Protein Polymers. J Mol Biol. 2018, vol. 430(23), p. 4619-4635.

Segura et al., "New developments in lentiviral vector design, production and purification". Expert opinion on biological therapy. Aug. 1, 2013; 13(7): 987-1011.

Velho et al., "Divergent low-density lipoprotein receptor (LDLR) linked to low VSV G-dependent viral infectivity and unique serum lipid profile in zebra finches". Proc Natl Acad Sci US A. 2021, vol. 118(18): 3 pages.

Votaw et al., "IsoTag(TM) LV—A faster and more effective purification solution for lentiviral applications", Human Gene Therapy; 29th Annual Congress of Theeuropean-Society-of-Gene-and-Cell-Therapy (ESCGT) Edinburgh, UK Oct. 11-14, 2022, vol. 33, Oct. 11, 2022, 2 pages.

\* cited by examiner

FIG. 25A
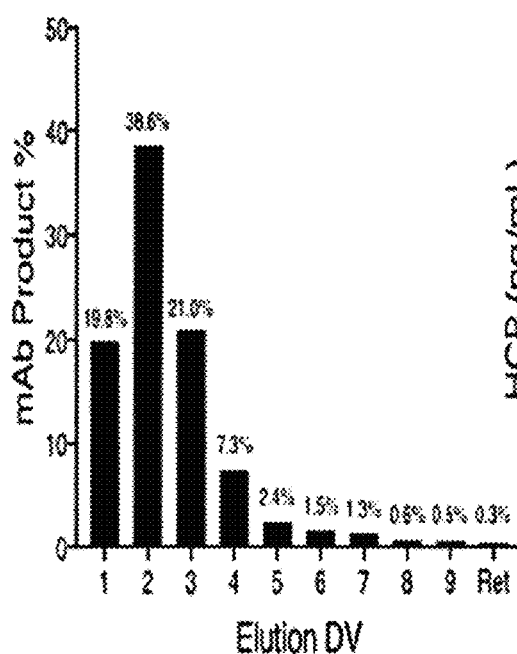
FIG. 25B
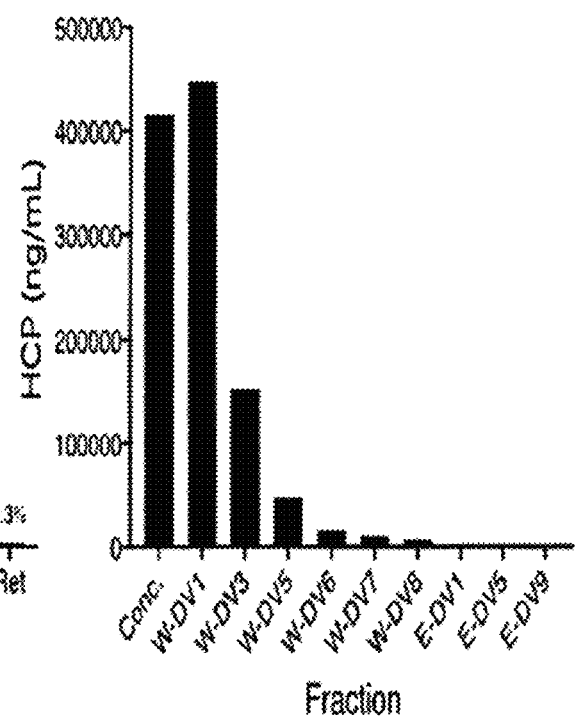
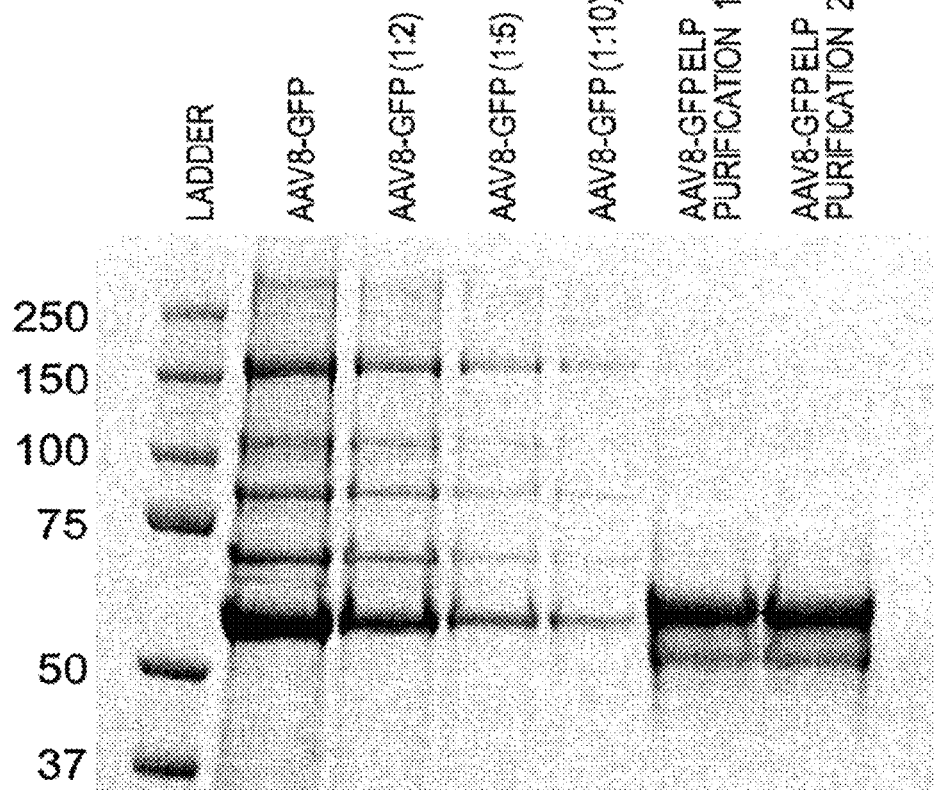
FIG. 26

```
                          SEQUENCE LISTING

Sequence total quantity: 48
SEQ ID NO: 1            moltype = AA  length = 58
FEATURE                 Location/Qualifiers
REGION                  1..58
                        note = capture domain
source                  1..58
                        mol_type = protein
                        organism = synthetic construct
SEQUENCE: 1
VDNKFNKEQQ NAFYEILHLP NLNEEQRNAF IQSLKDDPSQ SANLLAEAKK LNDAQAPK          58

SEQ ID NO: 2            moltype = AA  length = 59
FEATURE                 Location/Qualifiers
REGION                  1..59
                        note = capture domain
source                  1..59
                        mol_type = protein
                        organism = synthetic construct
SEQUENCE: 2
VDNKFNKEQQ NAFYEILSLP NLNEEQRAAF IQSLKDDPSQ SANLLAEAKK LNDAQAPKG         59

SEQ ID NO: 3            moltype = AA  length = 59
FEATURE                 Location/Qualifiers
REGION                  1..59
                        note = capture domain
source                  1..59
                        mol_type = protein
                        organism = synthetic construct
SEQUENCE: 3
VDNKFNKEHQ NAFYEILHLP NLNEEQRNAF IQSLKHDPSQ SANLLAEAKK LNDAQAPKG         59

SEQ ID NO: 4            moltype = AA  length = 254
FEATURE                 Location/Qualifiers
REGION                  1..254
                        note = capture domain
source                  1..254
                        mol_type = protein
                        organism = synthetic construct
SEQUENCE: 4
AQHDEAQQNA FYQVLNMPNL NADQRNGFIQ SLKDDPSQSA NVLGEAQKLN DSQAPKADAQ        60
QNKFNKDQQS AFYEILNMPN LNEEQRNGFI QSLKDDPSQS TNVLGEAKKL NESQAPKADN        120
NFNKEQQNAF YEILNMPNLN EEQRNGFIQS LKDDPSQSAN LLAEAKKLNE SQAPKADNKF        180
NKEQQNAFYE ILHLPNLNEE QRNGFIQSLK DDPSQSANLL AEAKKLNDAQ APKADNKFNK        240
EQQNAFYEIL HLPN                                                         254

SEQ ID NO: 5            moltype = AA  length = 56
FEATURE                 Location/Qualifiers
REGION                  1..56
                        note = capture domain
source                  1..56
                        mol_type = protein
```

```
                        organism = synthetic construct
SEQUENCE: 5
TYKLILNGKT LKGETTTEAV DAATAEKVFK QYANDNGVDG EWTYDDATKT FTVTEG          56

SEQ ID NO: 6            moltype = AA  length = 189
FEATURE                 Location/Qualifiers
REGION                  1..189
                        note = capture domain
source                  1..189
                        mol_type = protein
                        organism = synthetic construct
SEQUENCE: 6
KTDTYKLILN GKTLKGETTT EAVDAATAEK VFKQYANDNG VDGEWTYDDA TKTFTVTEKP      60
EVIDASELTP AVTTYKLVIN GKTLKGETTT KAVDAETAEK AFKQYANDNG VDGVWTYDDA     120
TKTFTVTEMV TEVPGDAPTE PEKPEASIPL VPLTPATPIA KDDAKKDDTK KEDAKKPEAK     180
KDDAKKAET                                                             189

SEQ ID NO: 7            moltype = AA  length = 76
FEATURE                 Location/Qualifiers
REGION                  1..76
                        note = capture domain
source                  1..76
                        mol_type = protein
                        organism = synthetic construct
SEQUENCE: 7
KEETPETPET DSEEEVTIKA NLIFANGSTQ TAEFKGTFEK ATSEAYAYAD TLKKDNGEYT      60
VDVADKGYTL NIKFAG                                                      76

SEQ ID NO: 8            moltype = AA  length = 7
FEATURE                 Location/Qualifiers
REGION                  1..7
                        note = capture domain
VARIANT                 5
                        note = R, H or K
VARIANT                 6
                        note = R or H
VARIANT                 7
                        note = P or S
source                  1..7
                        mol_type = protein
                        organism = synthetic construct
SEQUENCE: 8
GYVSXXX                                                                 7

SEQ ID NO: 9            moltype = AA  length = 226
FEATURE                 Location/Qualifiers
REGION                  1..226
                        note = capture domain
source                  1..226
                        mol_type = protein
                        organism = synthetic construct
SEQUENCE: 9
SDVQLQESGP DLVKPSQSLS LTCTVTGYSI TSGYTWHWIR QFPGNKQEWG YIHFSGYTNY      60
NPSLKSRVSI TRDTSKNQFF LHLNSVTTED TATYYCARGD YGYEWFTYWG QGTLVTVSAD     120
IQMTQSSSSF SVSLGDRVTI TCKASEDIHN RLAWYKQKPG NAPRLLISGA TSLETGVPSR     180
FSGSGSGKDY TLSITSLQNE DVATYYCQQY WIGPFTFGSG TNLEIK                    226

SEQ ID NO: 10           moltype = AA  length = 11
FEATURE                 Location/Qualifiers
REGION                  1..11
                        note = capture domain
source                  1..11
                        mol_type = protein
                        organism = synthetic construct
SEQUENCE: 10
GYVSRHPGGG C                                                           11

SEQ ID NO: 11           moltype = AA  length = 12
FEATURE                 Location/Qualifiers
REGION                  1..12
                        note = capture domain
source                  1..12
                        mol_type = protein
                        organism = synthetic construct
SEQUENCE: 11
GYVSRHPGGG GS                                                          12

SEQ ID NO: 12           moltype = AA  length = 11
FEATURE                 Location/Qualifiers
```

```
REGION                  1..11
                        note = capture domain
source                  1..11
                        mol_type = protein
                        organism = synthetic construct
SEQUENCE: 12
FHENWPSGGG C                                                                11

SEQ ID NO: 13           moltype = AA   length = 12
FEATURE                 Location/Qualifiers
REGION                  1..12
                        note = capture domain
source                  1..12
                        mol_type = protein
                        organism = synthetic construct
SEQUENCE: 13
FHENWPSGGG GS                                                               12

SEQ ID NO: 14           moltype = AA   length = 7
FEATURE                 Location/Qualifiers
REGION                  1..7
                        note = capture domain
source                  1..7
                        mol_type = protein
                        organism = synthetic construct
SEQUENCE: 14
GVVTINP                                                                     7

SEQ ID NO: 15           moltype = AA   length = 7
FEATURE                 Location/Qualifiers
REGION                  1..7
                        note = capture domain
source                  1..7
                        mol_type = protein
                        organism = synthetic construct
SEQUENCE: 15
GLVTPSG                                                                     7

SEQ ID NO: 16           moltype = AA   length = 7
FEATURE                 Location/Qualifiers
REGION                  1..7
                        note = capture domain
source                  1..7
                        mol_type = protein
                        organism = synthetic construct
SEQUENCE: 16
GYVSHRS                                                                     7

SEQ ID NO: 17           moltype = AA   length = 7
FEATURE                 Location/Qualifiers
REGION                  1..7
                        note = capture domain
source                  1..7
                        mol_type = protein
                        organism = synthetic construct
SEQUENCE: 17
KVWILTP                                                                     7

SEQ ID NO: 18           moltype = AA   length = 7
FEATURE                 Location/Qualifiers
REGION                  1..7
                        note = capture domain
source                  1..7
                        mol_type = protein
                        organism = synthetic construct
SEQUENCE: 18
KLWVIPQ                                                                     7

SEQ ID NO: 19           moltype = AA   length = 479
FEATURE                 Location/Qualifiers
REGION                  1..479
                        note = capture domain
source                  1..479
                        mol_type = protein
                        organism = synthetic construct
SEQUENCE: 19
GVSAGESVQI TLPKNEVQLN AYVLQEPPKG ETYTYDWQLI THPRDYSGEM EGKHSQILKL            60
SKLTPGLYEF KVIVEGQNAH GEGYVNVTVK PEPRKNRPPI AIVSPQFQEI SLPTTSTVID           120
GSQSTDDDKI VQYHWEELKG PLREEKISED TAILKLSKLV PGNYTFSLTV VDSDGATNST           180
```

-continued

```
TANLTVNKAV DYPPVANAGP NQVITLPQNS ITLFGNQSTD DHGITSYEWS LSPSSKGKVV   240
EMQGVRTPTL QLSAMQEGDY TYQLTVTDTI GQQATAQVTV IVQPENNKPP QADAGPDKEL   300
TLPVDSTTLD GSKSSDDQKI ISYLWEKTQG PDGVQLENAN SSVATVTGLQ VGTYVFTLTV   360
KDERNLQSQS SVNVIVKEEI NKPPIAKITG NVVITLPTST AELDGSKSSD DKGIVSYLWT   420
RDEGSPAAGE VLNHSDHHPI LFLSNLVEGT YTFHLKVTDA KGESDTDRTT VEVKPDPRG    479

SEQ ID NO: 20            moltype = AA   length = 90
FEATURE                  Location/Qualifiers
REGION                   1..90
                         note = capture domain
source                   1..90
                         mol_type = protein
                         organism = synthetic construct
SEQUENCE: 20
SAGESVQITL PKNEVQLNAY VLQEPPKGET YTYDWQLITH PRDYSGEMEG KHSQILKLSK    60
LTPGLYEFKV IVEGQNAHGE GYVNVTVKPE                                    90

SEQ ID NO: 21            moltype = AA   length = 90
FEATURE                  Location/Qualifiers
REGION                   1..90
                         note = capture domain
source                   1..90
                         mol_type = protein
                         organism = synthetic construct
SEQUENCE: 21
IAIVSPQFQE ISLPTTSTVI DGSQSTDDDK IVQYHWEELK GPLREEKISE DTAILKLSKL    60
VPGNYTFSLT VVDSDGATNS TTANLTVNKA                                    90

SEQ ID NO: 22            moltype = AA   length = 190
FEATURE                  Location/Qualifiers
REGION                   1..190
                         note = capture domain
source                   1..190
                         mol_type = protein
                         organism = synthetic construct
SEQUENCE: 22
MGVSAGESVQ ITLPKNEVQL NAYVLQEPPK GETYTYDWQL ITHPRDYSGE MEGKHSQILK    60
LSKLTPGLYE FKVIVEGQNA HGEGYVNVTV KPEPRKNRPP IAIVSPQFQE ISLPTTSTVI   120
DGSQSTDDDK IVQYHWEELK GPLREEKISE DTAILKLSKL VPGNYTFSLT VVDSDGATNS   180
TTANLTVNKA                                                         190

SEQ ID NO: 23            moltype = AA   length = 91
FEATURE                  Location/Qualifiers
REGION                   1..91
                         note = capture domain
source                   1..91
                         mol_type = protein
                         organism = synthetic construct
SEQUENCE: 23
VANAGPNQVI TLPQNSITLF GNQSTDDHGI TSYEWSLSPS SKGKVVEMQG VRTPTLQLSA    60
MQEGDYTYQL TVTDTIGQQA TAQVTVIVQP E                                  91

SEQ ID NO: 24            moltype = AA   length = 89
FEATURE                  Location/Qualifiers
REGION                   1..89
                         note = capture domain
source                   1..89
                         mol_type = protein
                         organism = synthetic construct
SEQUENCE: 24
QADAGPDKEL TLPVDSTTLD GSKSSDDQKI ISYLWEKTQG PDGVQLENAN SSVATVTGLQ    60
VGTYVFTLTV KDERNLQSQS SVNVIVKEE                                     89

SEQ ID NO: 25            moltype = AA   length = 93
FEATURE                  Location/Qualifiers
REGION                   1..93
                         note = capture domain
source                   1..93
                         mol_type = protein
                         organism = synthetic construct
SEQUENCE: 25
IAKITGNVVI TLPTSTAELD GSKSSDDKGI VSYLWTRDEG SPAAGEVLNH SDHHPILFLS    60
NLVEGTYTFH LKVTDAKGES DTDRTTVEVK PDP                                93

SEQ ID NO: 26            moltype = AA   length = 46
FEATURE                  Location/Qualifiers
REGION                   1..46
                         note = capture domain
source                   1..46
```

```
SEQUENCE: 26
LAEAKVLANR ELDKYGVSDY YKNLINNAKT VEGVKALIDE ILAALP                    46

SEQ ID NO: 27           moltype = AA  length = 5
FEATURE                 Location/Qualifiers
REGION                  1..5
                        note = polypeptide with phase behavior
source                  1..5
                        mol_type = protein
                        organism = synthetic construct
SEQUENCE: 27
GVGVP                                                                 5

SEQ ID NO: 28           moltype = AA  length = 25
FEATURE                 Location/Qualifiers
REGION                  1..25
                        note = polypeptide with phase behavior
source                  1..25
                        mol_type = protein
                        organism = synthetic construct
SEQUENCE: 28
GVGVPGLGVP GVGVPGLGVP GVGVP                                           25

SEQ ID NO: 29           moltype = AA  length = 25
FEATURE                 Location/Qualifiers
REGION                  1..25
                        note = polypeptide with phase behavior
source                  1..25
                        mol_type = protein
                        organism = synthetic construct
SEQUENCE: 29
GVGVPGVGVP GAGVPGVGVP GVGVP                                           25

SEQ ID NO: 30           moltype = AA  length = 25
FEATURE                 Location/Qualifiers
REGION                  1..25
                        note = polypeptide with phase behavior
source                  1..25
                        mol_type = protein
                        organism = synthetic construct
SEQUENCE: 30
GVGVPGWGVP GVGVPGWGVP GVGVP                                           25

SEQ ID NO: 31           moltype = AA  length = 45
FEATURE                 Location/Qualifiers
REGION                  1..45
                        note = polypeptide with phase behavior
source                  1..45
                        mol_type = protein
                        organism = synthetic construct
SEQUENCE: 31
GVGVPGVGVP GVGVPGVGVP GVGVPGVGVP GEGVPGFGVP GVGVP                     45

SEQ ID NO: 32           moltype = AA  length = 45
FEATURE                 Location/Qualifiers
REGION                  1..45
                        note = polypeptide with phase behavior
source                  1..45
                        mol_type = protein
                        organism = synthetic construct
SEQUENCE: 32
GVGVPGVGVP GVGVPGVGVP GVGVPGVGVP GKGVPGFGVP GVGVP                     45

SEQ ID NO: 33           moltype = AA  length = 25
FEATURE                 Location/Qualifiers
REGION                  1..25
                        note = polypeptide with phase behavior
source                  1..25
                        mol_type = protein
                        organism = synthetic construct
SEQUENCE: 33
GAGVPGVGVP GAGVPGVGVP GAGVP                                           25

SEQ ID NO: 34           moltype = AA  length = 5
FEATURE                 Location/Qualifiers
REGION                  1..5
                        note = polypeptide with phase behavior
```

```
VARIANT              4
                     note = any naturally occurring amino acid except P
source               1..5
                     mol_type = protein
                     organism = synthetic construct
SEQUENCE: 34
VPGXG                                                                    5

SEQ ID NO: 35        moltype = AA  length = 25
FEATURE              Location/Qualifiers
REGION               1..25
                     note = polypeptide with phase behavior
source               1..25
                     mol_type = protein
                     organism = synthetic construct
SEQUENCE: 35
VPGVGVPGVG VPGVGVPGVG VPGVG                                             25

SEQ ID NO: 36        moltype = AA  length = 25
FEATURE              Location/Qualifiers
REGION               1..25
                     note = polypeptide with phase behavior
source               1..25
                     mol_type = protein
                     organism = synthetic construct
SEQUENCE: 36
VPGVGVPGLG VPGVGVPGLG VPGVG                                             25

SEQ ID NO: 37        moltype = AA  length = 25
FEATURE              Location/Qualifiers
REGION               1..25
                     note = polypeptide with phase behavior
source               1..25
                     mol_type = protein
                     organism = synthetic construct
SEQUENCE: 37
VPGVGVPGVG VPGAGVPGVG VPGVG                                             25

SEQ ID NO: 38        moltype = AA  length = 457
FEATURE              Location/Qualifiers
REGION               1..457
                     note = capture fusion protein
source               1..457
                     mol_type = protein
                     organism = synthetic construct
SEQUENCE: 38
MSKGPGVGVP GLGVPGVGVP GLGVPGVGVP GVGVPGLGVP GVGVPGLGVP GVGVPVGVPG        60
LGVPGVGVPG LGVPGVGVPG VGVPGLGVPG VGVPGLGVPG VGVPVGVPGL GVPGVGVPGL       120
GVPGVGVPGV GVPGLGVPGV GVPGLGVPGV GVPVGVPGLG VPGVGVPGLG VPGVGVPGVG       180
VPGLGVPGVG VPGLGVPGVG VPVGVPGLGV PGVGVPGLGV PGVGVPGVGV PGLGVPGVGV       240
PGLGVPGVGV PVGVPGLGVP GVGVPGLGVP GVGVPGVGVP GLGVPGVGVP GLGVPGVGVP       300
VGVPGLGVPG VGVPGLGVPG VGVPGVGVPG LGVPGVGVPV GVPGLGVPGV GVPGLGVPGV       360
GVPGLGVPGV GVPGVGVPGL GVPGVGVPGL GVPGVGVPGV DNKFNKEQQN AFYEILHLPN       420
LNEEQRNAFI QSLKDDPSQS ANLLAEAKKL NDAQAPK                                457

SEQ ID NO: 39        moltype = AA  length = 452
FEATURE              Location/Qualifiers
REGION               1..452
                     note = capture fusion protein
source               1..452
                     mol_type = protein
                     organism = synthetic construct
SEQUENCE: 39
MVDNKFNKEQ QNAFYEILHL PNLNEEQRNA FIQSLKDDPS QSANLLAEAK KLNDAQAPKG        60
VGVPGLGVPG VGVPGLGVPG VGVPGVGVPG LGVPGVGVPG LGVPGVGVPV GVPGLGVPGV       120
GVPGLGVPGV GVPGVGVPGL GVPGVGVPGL GVPGVGVPVG VPGLGVPGVG VPGLGVPGVG       180
VPGVGVPGLG VPGVGVPGLG VPGVGVPVGV PGLGVPGVGV PGLGVPGVGV PGVGVPGLGV       240
PGVGVPGLGV PGVGVPVGVP GLGVPGVGVP GLGVPGVGVP GVGVPGLGVP GVGVPGLGVP       300
GVGVPVGVPG LGVPGVGVPG LGVPGVGVPG VGVPGLGVPG VGVPGLGVPG VGVPVGVPGL       360
GVPGVGVPGL GVPGVGVPGV GVPGLGVPGV GVPGLGVPGV GVPVGVPGLG VPGVGVPGLG       420
VPGVGVPGVG VPGLGVPGVG VPGLGVPGVG VP                                    452

SEQ ID NO: 40        moltype = AA  length = 452
FEATURE              Location/Qualifiers
REGION               1..452
                     note = capture fusion protein
source               1..452
                     mol_type = protein
                     organism = synthetic construct
```

```
SEQUENCE: 40
MVGVPGLGVP GVGVPGLGVP GVGVPGVGVP GLGVPGVGVP GLGVPGVGVP VGVPGLGVPG    60
VGVPGLGVPG VGVPGLGVPG LGVPGVGVPG LGVPGVGVPV GVPGLGVPGV VGVPGLGVPG   120
GVPGVGVPGL GVPGVGVPGL GVPGVGVPVG VPGLGVPGVG VPGLGVPGVG VPGVGVPGLG   180
VPGVGVPGLG VPGVGVPVGV PGLGVPGVGV PGLGVPGVGV PGVGVPGLGV PGVGVPGLGV   240
PGVGVPVGVP GLGVPGVGVP GLGVPGVGVP GVGVPGLGVP GVGVPGLGVP GVGVPVGVPG   300
LGVPGVGVPG LGVPGVGVPG VGVPGLGVPG VGVPGLGVPG VGVPVGVPGL GVPGVGVPGL   360
GVPGVGVPGV GVPGLGVPGV GVPGLGVPGV GVPGVDNKFN KEQQNAFYEI LHLPNLNEEQ   420
RNAFIQSLKD DPSQSANLLA EAKKLNDAQA PK                                 452

SEQ ID NO: 41           moltype = AA  length = 649
FEATURE                 Location/Qualifiers
REGION                  1..649
                        note = capture fusion protein
source                  1..649
                        mol_type = protein
                        organism = synthetic construct
SEQUENCE: 41
MGVDNKFNKE QQNAFYEILH LPNLNEEQRN AFIQSLKDDP SQSANLLAEA KKLNDAQAPK    60
GVGVPGLGVP GVGVPGLGVP GVGVPGVGVP GLGVPGVGVP GLGVPGVGVP VGVPGLGVPG   120
VGVPGLGVPG VGVPGLGVPG LGVPGVGVPG LGVPGVGVPV GVPGLGVPGV VGVPGLGVPG   180
GVPGVGVPGL GVPGVGVPGL GVPGVGVPVG VPGLGVPGVG VPGLGVPGVG VPGVGVPGLG   240
VPGVGVPGLG VPGVGVPVGV PGLGVPGVGV PGLGVPGVGV PGVGVPGLGV PGVGVPGLGV   300
PGVGVPVGVP GLGVPGVGVP GLGVPGVGVP GVGVPGLGVP GVGVPGLGVP GVGVPVGVPG   360
LGVPGVGVPG LGVPGVGVPG VGVPGLGVPG VGVPGLGVPG VGVPVGVPGL GVPGVGVPGL   420
GVPGVGVPGV GVPGLGVPGV GVPGLGVPGV GVPVGVPGLG VPGVGVPGLG VPGVGVPGVG   480
VPGLGVPGVG VPGLGVPGVG VPVGVPGLGV PGVGVPGLGV PGVGVPGVGV PGLGVPGVGV   540
PGLGVPGVGV PVGVPGLGVP GVGVPGLGVP GVGVPGVGVP GLGVPGVGVP GLGVPGVGVP   600
VGVPGLGVPG VGVPGLGVPG VGVPGVGVPG LGVPGVGVPG LGVPGVGVP                649

SEQ ID NO: 42           moltype = AA  length = 708
FEATURE                 Location/Qualifiers
REGION                  1..708
                        note = capture fusion protein
source                  1..708
                        mol_type = protein
                        organism = synthetic construct
SEQUENCE: 42
MVGVPGLGVP GVGVPGLGVP GVGVPGVGVP GLGVPGVGVP GLGVPGVGVP VGVPGLGVPG    60
VGVPGLGVPG VGVPGLGVPG LGVPGVGVPG LGVPGVGVPV GVPGLGVPGV VGVPGLGVPG   120
GVPGVGVPGL GVPGVGVPGL GVPGVGVPVG VPGLGVPGVG VPGLGVPGVG VPGVGVPGLG   180
VPGVGVPGLG VPGVGVPVGV PGLGVPGVGV PGLGVPGVGV PGVGVPGLGV PGVGVPGLGV   240
PGVGVPVGVP GLGVPGVGVP GLGVPGVGVP GVGVPGLGVP GVGVPGLGVP GVGVPVGVPG   300
LGVPGVGVPG LGVPGVGVPG VGVPGLGVPG VGVPGLGVPG VGVPVGVPGL GVPGVGVPGL   360
GVPGVGVPGV GVPGLGVPGV GVPGLGVPGV GVPVGVPGLG VPGVGVPGLG VPGVGVPGVG   420
VPGLGVPGVG VPGLGVPGVG VPVGVPGLGV PGVGVPGLGV PGVGVPGVGV PGLGVPGVGV   480
PGLGVPGVGV PVGVPGLGVP GVGVPGLGVP GVGVPGVGVP GLGVPGVGVP GLGVPGVGVP   540
VGVPGLGVPG VGVPGLGVPG VGVPGVGVPG LGVPGVGVPG LGVPGVGVPG VDNKFNKEQQ   600
NAFYEILHLP NLNEEQRNAF IQSLKDDPSQ SANLLAEAKK LNDAQAPKGV DNKFNKEQQN   660
AFYEILHLPN LNEEQRNAFI QSLKDDPSQS ANLLAEAKKL NDAQAPKG                708

SEQ ID NO: 43           moltype = AA  length = 709
FEATURE                 Location/Qualifiers
REGION                  1..709
                        note = capture fusion protein
source                  1..709
                        mol_type = protein
                        organism = synthetic construct
SEQUENCE: 43
MGVDNKFNKE QQNAFYEILH LPNLNEEQRN AFIQSLKDDP SQSANLLAEA KKLNDAQAPK    60
GVGVPGLGVP GVGVPGLGVP GVGVPGVGVP GLGVPGVGVP GLGVPGVGVP VGVPGLGVPG   120
VGVPGLGVPG VGVPGLGVPG LGVPGVGVPG LGVPGVGVPV GVPGLGVPGV VGVPGLGVPG   180
GVPGVGVPGL GVPGVGVPGL GVPGVGVPVG VPGLGVPGVG VPGLGVPGVG VPGVGVPGLG   240
VPGVGVPGLG VPGVGVPVGV PGLGVPGVGV PGLGVPGVGV PGVGVPGLGV PGVGVPGLGV   300
PGVGVPVGVP GLGVPGVGVP GLGVPGVGVP GVGVPGLGVP GVGVPGLGVP GVGVPVGVPG   360
LGVPGVGVPG LGVPGVGVPG VGVPGLGVPG VGVPGLGVPG VGVPVGVPGL GVPGVGVPGL   420
GVPGVGVPGV GVPGLGVPGV GVPGLGVPGV GVPVGVPGLG VPGVGVPGLG VPGVGVPGVG   480
VPGLGVPGVG VPGLGVPGVG VPVGVPGLGV PGVGVPGLGV PGVGVPGVGV PGLGVPGVGV   540
PGLGVPGVGV PVGVPGLGVP GVGVPGLGVP GVGVPGVGVP GLGVPGVGVP GLGVPGVGVP   600
VGVPGLGVPG VGVPGLGVPG VGVPGVGVPG LGVPGVGVPG LGVPGVGVPG VDNKFNKEQQ   660
NAFYEILHLP NLNEEQRNAF IQSLKDDPSQ SANLLAEAKK LNDAQAPKG                709

SEQ ID NO: 44           moltype = AA  length = 649
FEATURE                 Location/Qualifiers
REGION                  1..649
                        note = capture fusion protein
source                  1..649
                        mol_type = protein
                        organism = synthetic construct
```

```
SEQUENCE: 44
MVGVPGLGVP GVGVPGLGVP GVGVPGVGVP GLGVPGVGVP GLGVPGVGVP VGVPGLGVPG    60
VGVPGLGVPG VGVPGVGVPG LGVPGVGVPG LGVPGVGVPV GVPGLGVPGV GVPGLGVPGV   120
GVPGVGVPGL GVPGVGVPGL GVPGVGVPVG VPGLGVPGVG VPGLGVPGVG VPGVGVPGLG   180
VPGVGVPGLG VPGVGVPVGV PGLGVPGVGV PGLGVPGVGV PGVGVPGLGV PGVGVPGLGV   240
PGVGVPVGVP GLGVPGVGVP GLGVPGVGVP GVGVPGLGVP GVGVPGLGVP GVGVPVGVPG   300
LGVPGVGVPG LGVPGVGVPG VGVPGLGVPG VGVPGLGVPG VGVPVGVPGL GVPGVGVPGL   360
GVPGVGVPGV GVPGLGVPGV GVPGLGVPGV GVPVGVPGLG VPGVGVPGLG VPGVGVPGVG   420
VPGLGVPGVG VPGLGVPGVG VPVGVPGLGV PGVGVPGVGV PGVGVPGLGV VPGLGVPGVG   480
PGLGVPGVGV PVGVPGLGVP GVGVPGLGVP GVGVPGVGVP GLGVPGVGVP GLGVPGVGVP   540
VGVPGLGVPG VGVPGLGVPG VGVPGVGVPG LGVPGVGVPG LGVPGVGVPG VDNKFNKEQQ   600
NAFYEILHLP NLNEEQRNAF IQSLKDDPSQ SANLLAEAKK LNDAQAPKG              649

SEQ ID NO: 45        moltype = AA   length = 661
FEATURE              Location/Qualifiers
REGION               1..661
                     note = capture fusion protein
source               1..661
                     mol_type = protein
                     organism = synthetic construct
SEQUENCE: 45
MVGVPGVGVP GVGVPGVGVP GVGVPGVGVP GVGVPGVGVP GVGVPGVGVP GVGVPGVGVP    60
GVGVPGVGVP GVGVPGVGVP GVGVPGVGVP GVGVPGVGVP GVGVPGVGVP GVGVPGVGVP   120
GVGVPGVGVP GVGVPGVGVP GVGVPGVGVP GVGVPGVGVP GVGVPGVGVP GVGVPGVGVP   180
GVGVPGVGVP GVGVPGVGVP GVGVPGVGVP GVGVPGVGVP GVGVPGVGVP GVGVPGVGVP   240
GVGVPGVGVP GVGVPGVGVP GVGVPGVGVP GVGVPGVGVP GVGVPGVGVP GVGVPGVGVP   300
GVGVPGVGVP GVGVPGVGVP GVGVPGVGVP GVGVPGVGVP GVGVPGVGVP GVGVPGVGVP   360
GVGVPGVGVP GVGVPGVGVP GVGVPGVGVP GVGVPGVGVP GVGVPGVGVP GVGVPGVGVP   420
GVGVPGVGVP GVGVPGVGVP GVGVPGVGVP GVGVPGVGVP GVGVPGVGVP GVGVPGVGVP   480
GVGVPGVGVP GVGVPGVGVP GVGVPGVGVP GVGVPGVGVP GVGVPGVGVP GVGVPGVGVP   540
GVGVPGVGVP GVGVPGVGVP GVGVPGVGVP GVGVPGVGVP GVGVPGVGVP GVGVPGVGVP   600
GGVDNKFNKE QQNAFYEILH LPNLNEEQRN AFIQSLKDDP SQSANLLAEA KKLNDAQAPK   660
G                                                                  661

SEQ ID NO: 46        moltype = AA   length = 461
FEATURE              Location/Qualifiers
REGION               1..461
                     note = capture fusion protein
source               1..461
                     mol_type = protein
                     organism = synthetic construct
SEQUENCE: 46
MVGVPGAGVP GVGVPGAGVP GVGVPGAGVP GVGVPGAGVP GVGVPGAGVP GVGVPGAGVP    60
GVGVPGAGVP GVGVPGAGVP GVGVPGAGVP GVGVPGAGVP GVGVPGAGVP GVGVPGAGVP   120
GVGVPGAGVP GVGVPGAGVP GVGVPGAGVP GVGVPGAGVP GVGVPGAGVP GVGVPGAGVP   180
GVGVPGAGVP GVGVPGAGVP GVGVPGAGVP GVGVPGAGVP GVGVPGAGVP GVGVPGAGVP   240
GVGVPGAGVP GVGVPGAGVP GVGVPGAGVP GVGVPGAGVP GVGVPGAGVP GVGVPGAGVP   300
GVGVPGAGVP GVGVPGAGVP GVGVPGAGVP GVGVPGAGVP GVGVPGAGVP GVGVPGAGVP   360
GVGVPGAGVP GVGVPGAGVP GVGVPGAGVP GVGVPGAGVP GGVDNKFNKE QQNAFYEILH   420
LPNLNEEQRN AFIQSLKDDP SQSANLLAEA KKLNDAQAPK G                      461

SEQ ID NO: 47        moltype = AA   length = 461
FEATURE              Location/Qualifiers
REGION               1..461
                     note = capture fusion protein
source               1..461
                     mol_type = protein
                     organism = synthetic construct
SEQUENCE: 47
MVGVPGAGVP GVGVPGAGVP GVGVPGAGVP GVGVPGAGVP GVGVPGAGVP GVGVPGAGVP    60
GVGVPGAGVP GVGVPGAGVP GVGVPGAGVP GVGVPGAGVP GVGVPGAGVP GVGVPGAGVP   120
GVGVPGAGVP GVGVPGAGVP GVGVPGAGVP GVGVPGAGVP GVGVPGAGVP GVGVPGAGVP   180
GVGVPGAGVP GVGVPGAGVP GVGVPGAGVP GVGVPGAGVP GVGVPGAGVP GVGVPGAGVP   240
GVGVPGAGVP GVGVPGAGVP GVGVPGAGVP GVGVPGAGVP GVGVPGAGVP GVGVPGAGVP   300
GVGVPGAGVP GVGVPGAGVP GVGVPGAGVP GVGVPGAGVP GVGVPGAGVP GVGVPGAGVP   360
GVGVPGAGVP GVGVPGAGVP GVGVPGAGVP GVGVPGAGVP GGVDNKFNKE QQNAFYEILH   420
LPNLNEEQRN AFIQSLKDDP SQSANLLAEA KKLNDAQAPK G                      461

SEQ ID NO: 48        moltype = AA   length = 455
FEATURE              Location/Qualifiers
REGION               1..455
                     note = capture fusion protein
source               1..455
                     mol_type = protein
                     organism = synthetic construct
SEQUENCE: 48
MSKGPGVGVP GLGVPGVGVP GLGVPGVGVP GVGVPGLGVP GVGVPGLGVP GVGVPVGVPG    60
LGVPGVGVPG LGVPGVGVPG VGVPGLGVPG VGVPGLGVPG VGVPVGVPGL GVPGVGVPGL   120
GVPGVGVPGV GVPGLGVPGV GVPGLGVPGV GVPVGVPGLG VPGVGVPGLG VPGVGVPGVG   180
```

-continued

```
VPGLGVPGVG VPGLGVPGVG VPVGVPGLGV PGVGVPGLGV PGVGVPGVGV PGLGVPGVGV   240
PGLGVPGVGV PVGVPGLGVP GVGVPGLGVP GVGVPGVGVP GLGVPGVGVP GLGVPGVGVP   300
VGVPGLGVPG VGVPGLGVPG VGVPGVGVPG LGVPGVGVPG LGVPGVGVPV GVPGLGVPGV   360
GVPGLGVPGV GVPGVGVPGL GVPGVGVPGL GVPGVGVPGT YKLILNGKTL KGETTTEAVD   420
AATAEKVFKQ YANDNGVDGE WTYDDATKTF TVTEG                              455
```

GENETICALLY ENCODED POLYPEPTIDE FOR AFFINITY CAPTURE AND PURIFICATION OF BIOLOGICS

STATEMENT OF PRIORITY

This application is a continuation of U.S. patent application Ser. No. 17/349,558, filed Jun. 16, 2021, which is a continuation of U.S. patent application Ser. No. 17/268,314, filed Feb. 12, 2021, which is the U.S. National Phase Application, filed under 35 U.S.C. § 371, of International Patent Application No. PCT/2019/046607, filed Aug. 15, 2019, which claims the benefit of priority, under 35 U.S.C. § 119(e), of U.S. Provisional Application No. 62/764,833, filed on Aug. 16, 2018, the entire contents of which are incorporated by reference herein.

DESCRIPTION OF THE TEXT FILE SUBMITTED ELECTRONICALLY

The contents of the electronic sequence listing (ISOL_001_03US_SeqList_ST26.xml; Size: 70,501 bytes; and Date of Creation: Jul. 3, 2023) are herein incorporated by reference in its entirety.

FIELD OF THE INVENTION

The invention relates to genetically encoded fusion proteins comprised of a capture component that binds a target with high affinity and a peptide polymer, such as elastin-like polypeptides, that display phase behavior and can be used for purification. The invention further relates to methods for optimizing capture fusion proteins for individual biologic targets such that phase separation occurs under desirable conditions, such as at room temperature, lower concentrations of salt, and/or at suitable pH ranges and optimized capture domains and polypeptides with phase behavior that have been identified by the optimization methods.

BACKGROUND OF THE INVENTION

Biologics make up a rapidly expanding drug class and they are attractive because of high affinity and specificity for a given target, as well as low toxicity and biodegradability. However, their manufacturing and purification can be quite difficult. Biologics, including therapeutic enzymes, antibodies, gene delivery vectors, and other fusion proteins, are typically manufactured recombinantly in bacteria, yeast, or mammalian host cells. They must then go through many downstream purification processes in order to meet FDA standards of purity. Host cell proteins, nucleic acids, endotoxins, and viruses are the main contaminants that must be cleared. One commonly used method of purification is affinity chromatography. For example, in antibody purification, affinity capture with Protein A chromatography is often the first step after clarification of the cell culture harvest. While affinity chromatography achieves high levels of purity (>90%) due to its selectivity for the target biologic, it is expensive, time consuming, and requires technical equipment that is expensive to maintain and requires skilled labor. It is also difficult to scale because conditions are not linear as column diameters become large.

There is a need in the art for improved tools and methods for rapidly and cost-effectively purifying biologics to a high degree while achieving acceptable levels of contaminants.

SUMMARY OF THE INVENTION

Combining liquid-liquid phase separation with affinity capture is a useful alternative to affinity chromatography. The present invention provides a capture fusion protein comprising a polypeptide with phase behavior fused to an affinity capture molecule such that the phase behavior can be conferred to the target biologic. Because contaminants do not display phase behavior, this can be leveraged to separate contaminants from the complexed biologic of interest. The captured biologic can then be separated from the purification reagent by adjusting ionic strength or pH, or by adding in a competitive binder with greater affinity for the capture component. The phase behavior is then leveraged again to separate the capture fusion protein from the biologic. One caveat to this method is that one must be able to trigger the phase separation under mild conditions, such as with a small addition of salt, because high concentrations of salt will begin to salt out other contaminants. Ideally, this phase separation will also occur at or below room temperature, to better maintain the stability of the target biologic and to prevent the need for expensive jacketed heating or cooling during the unit operation.

The present invention is based in part on the development of methods for optimizing capture fusion proteins for individual biologic targets such that phase separation occurs under desirable conditions, such as at room temperature, lower concentrations of salt, and/or at suitable pH ranges. The invention is further based on optimized capture domains and polypeptides with phase behavior that have been identified by the optimization methods.

Thus, one aspect of the invention relates to a method for preparing a capture fusion protein that is optimized for capturing and purifying a biologic target, the method comprising:

a. preparing a capture fusion protein comprising at least one capture domain that specifically binds the biologic target and at least one polypeptide with phase behavior;

b. determining one or more parameters under which the capture fusion protein captures the biologic target, the captured biologic target aggregates, the aggregate resolubilizes, and/or the biologic target elutes from the capture fusion protein;

c. modifying the at least one capture domain that specifically binds the biologic target and/or at least one polypeptide with phase behavior to alter the one or more parameters under which the capture fusion protein binds to the biologic target, purifies the biologic target, and/or elutes the biologic target; and d. identifying a modified capture fusion protein that provides optimized parameters under which the capture fusion protein captures the biologic target, the captured biologic target aggregates, the aggregate resolubilizes, and/or the biologic target elutes from the capture fusion protein.

Another aspect of the invention relates to a capture fusion protein made by the optimization method of the invention.

A further aspect of the invention relates to a capture fusion protein comprising at least one capture domain that specifically binds the biologic target and at least one polypeptide with phase behavior, wherein the capture domain comprises an amino acid sequence selected from:

a.
(SEQ ID NO: 1)
VDNKFNKEQQNAFYEILHLPNLNEEQRNAFIQSLKDDPSQSANLLAEAKKLN
DAQAPK;

b.
(SEQ ID NO: 2)
VDNKFNKEQQNAFYEILSLPNLNEEQRAAFIQSLKDDPSQSANLLAEAKKLN
DAQAPKG;

c.
(SEQ ID NO: 3)
VDNKFNKEIIQNAFYEILHLPNLNEEQRNAFIQSLKHDPSQSANLLAEAKKLN
DAQAPKG;

d.
(SEQ ID NO: 4)
AQHDEAQQNAFYQVLNMPNLNADQRNGFIQSLKDDPSQSANVLGEAQKLN

DSQAPKADAQQNKFNKDQQSAFYEILNMPNLNEEQRNGFIQSLKDDPSQSTNVLGE

AKKLNESQAPKADNNFNKEQQNAFYEILNMPNLNEEQRNGFIQSLKDDPSQSANLL

AEAKKLNESQAPKADNKFNKEQQNAFYEILHLPNLNEEQRNGFIQSLKDDPSQSAN

LLAEAKKLNDAQAPKADNKFNKEQQNAFYEILHLPN;

e.
(SEQ ID NO: 5)
TYKLILNGKTLKGETTTEAVDAATAEKVFKQYANDNGVDGEWTYDDATKT
FTVTEG;

f.
(SEQ ID NO: 6)
KTDTYKLILNGKTLKGETTTEAVDAATAEKVFKQYANDNGVDGEWTYDDA

TKTFTVTEKPEVIDASELTPAVTTYKLVINGKTLKGETTTKAVDAETAEKAFKQYAN

DNGVDGVWTYDDATKTFTVTEMVTEVPGDAPTEPEKPEASIPLVPLTPATPIAKDDA

KKDDTKKEDAKKPEAKKDDAKKAET;

g.
(SEQ ID NO: 7)
KEETPETPETDSEEEVTIKANLIFANGSTQTAEFKGTFEKATSEAYAYADTLKK
DNGEYTVDVADKGYTLNIKFAG;

h
(SEQ ID NO: 8)
GYVS(R/H/K)(R/H)(P/S);

i.
(SEQ ID NO: 9)
SDVQLQESGPDLVKPSQSLSLTCTVTGYSITSGYTWHWIRQFPGNKQEWGYIH

FSGYTNYNPSLKSRVSITRDTSKNQFFLHLNSVTTEDTATYYCARGDYGYEWFTY

WGQGTLVTVSADIQMTQSSSSFSVSLGDRVTITCKASEDIHNRLAWYKQKPGNAP

RLLISGATSLETGVPSRFSGSGSGKDYTLSITSLQNEDVATYYCQQYWIGPFTEGSG

TNLEIK;

j.
(SEQ ID NO: 10)
GYVSRHPGGC;

k
(SEQ ID NO: 11)
GYVSRHPGGGS;

l.
(SEQ ID NO: 12)
FHENWPSGGGC;

m.
(SEQ ID NO: 13)
FIIENWPSGGGGS;

-continued n.
(SEQ ID NO: 14)
GVVTINP;

o.
(SEQ ID NO: 15)
GLVTPSG;

p.
(SEQ ID NO: 16)
GYVSHRS;

q.
(SEQ ID NO: 17)
KVWILTP;

r.
(SEQ ID NO: 18)
KLWVIPQ;

s.
(SEQ ID NO: 19)
GVSAGESVQITLPKNEVQLNAYVLQEPPKGETYTYDWQLITHPRDYSGEM

EGKHSQILKLSKLTPGLYEFKVIVEGQNAHGEGYVNVTVKPEPRKNRPPIAIVS

PQFQEISLPTTSTVIDGSQSTDDDKIVQYHWEELKGPLREEKISEDTAILKLSKLV

PGNYTFSLTVVDSDGATNSTTANLTVNKAVDYPPVANAGPNQVITLPQNSITLF

GNQSTDDHGITSYEWSLSPSSKGKVVEMQGVRTPTLQLSAMQEGDYTYQLTVT

DTIGQQATAQVTVIVQPENNKPPQADAGPDKELTLPVDSTTLDGSKSSDDQKIIS

YLWEKTQGPDGVQLENANSSVATVTGLQVGTYVFTLTVKDERNLQSQSSVNVI

VKEEINKPPIAKITGNVVITLPTSTAELDGSKSSDDKGIVSYLWTRDEGSPAAGEV

LNHSDHHPILFLSNLVEGTYTFHLKVTDAKGESDTDRTTVEVKPDPRG;

t.
(SEQ ID NO: 20)
SAGES VQITLPKNEVQLNAYVLQEPPKGETYTYDWQLITHPRDYSGEMEGK
HSQ1LKLSKLTPGLYEFKVIVEGQNAHGEGYVNVTVKPE;

u.
(SEQ ID NO: 21)
IAIVSPQFQEISLPTTSTVIDGSQSTDDDKIVQYHWEELKGPLREEKISEDTAIL
KLSKLVPGNYTESLTVVDSDGATNSTTANLTVNK A;

v.
(SEQ ID NO: 22)
MGVSAGESVQITLPKNEVQLNAYVLQEPPKGETYTYDWQLITHPRDYSGEM

EGKHSQILKLSKLTPGLYEFKVIVEGQNAHGEGYVNVTVKPEPRKNRPPIAIVSPQ

FQEISLPTTSTVIDGSQSTDDDKIVQYHWEELKGPLREEKISEDTAILKLSKLVPGN

YTFSLTVVDSDGATNSTTANLTVNKA;

w.
(SEQ ID NO: 23)
VANAGPNQVITLPQNSITLFGNQSTDDHGITSYEWSLSPSSKGKVVEMQGVRT
PTLQLSAMQEGDYTYQLTVTDTIGQQATAQVTVIVQPE;

x.
(SEQ ID NO: 24)
QADAGPDKELTLPVDSTTLDGSKSSDDQKIISYLWEKTQGPDGVQLENANSS
VATVTGLQVGTYVFTLTVKDERNLQSQSSVNVIVKEE;

y.
(SEQ ID NO: 25)
IAKITGNVVITLPTSTAELDGSKSSDDKGIVSYLWTRDEGSPAAGEVLNHSDHH
PILFLSNLVEGTYTFHLKVTDAKGESDTDRTTVEVKPDP;
or z.
(SEQ ID NO: 26)
LAEAKVLANRELDKYGVSDYYKNLINNAKTVEGVKALIDEILAALP.

An additional aspect of the invention relates to a capture fusion protein comprising at least one capture domain that specifically binds the biologic target and at least one polypeptide with phase behavior, wherein the polypeptide with phase behavior comprises an amino acid sequence selected from:

a.
(SEQ ID NO: 27)
(GVGVP)$_n$;

b.
(SEQ ID NO: 28)
(GVGVPGLGVPGVGVPGLGVPGVGVP)$_m$;

c.
(SEQ ID NO: 29)
(GVGVPGVGVPGAGVPGVGVPGVGVP)$_m$;

d.
(SEQ ID NO: 30)
(GVGVPGWGVPGVGVPGWGVPGVGVP)$_m$;

e.
(SEQ ID NO: 31)
(GVGVPGVGVPGVGVPGVGVPGVGVPGVGVPGEGVPGFGVPGVGVP)$_m$;

f.
(SEQ ID NO: 32)
(GVGVPGVGVPGVGVPGVGVPGVGVPGVGVPGKGVPGFGVPGVGVP)$_m$;
or g.
(SEQ ID NO: 33)
GAGVPGVGVPGAGVPGVGVPGAGVP)$_m$;

or a randomized, scrambled analog thereof; wherein:
n is 20-120; and
m is 4-25.

Another aspect of the invention relates to a capture fusion protein comprising at least one capture domain that specifically binds the biologic target and at least one polypeptide with phase behavior, wherein the capture domain comprises an amino acid sequence selected from:

a.
(SEQ ID NO: 1)
VDNKFNKEQQNAFYEILHLPNLNEEQRNAFIQSLKDDPSQSANLLAEAKKLNDAQAPK;

b.
(SEQ ID NO: 2)
VDNKFNKEQQNAFYEILSLPNLNEEQRAAFIQSLKDDPSQSANLLAEAKKLNDAQAPKG;

c.
(SEQ ID NO: 3)
VDNKFNKEIIQNAFYEILHLPNLNEEQRNAFIQSLKHDPSQSANLLAEAKKLNDAQAPKG;

d.
(SEQ ID NO: 4)
AQHDEAQQNAFYQVLNMPNLNADQRNGFIQSLKDDPSQSANVLGEAQKLN

DSQAPKADAQQNKFNKDQQSAFYEILNMPNLNEEQRNGFIQSLKDDPSQSTNVLGE

AKKLNESQAPKADNNFNKEQQNAFYEILNMPNLNEEQRNGFIQSLKDDPSQSANLL

AEAKKLNESQAPKADNKFNKEQQNAFYEILHLPNLNEEQRNGFIQSLKDDPSQSAN

LLAEAKKLNDAQAPKADNKFNKEQQNAFYEILHLPN;

e.
(SEQ ID NO: 5)
TYKLILNGKTLKGETTTEAVDAATAEKVFKQYANDNGVDGEWTYDDATKTFTVTEG;

f.
(SEQ ID NO: 6)
KTDTYKLILNGKTLKGETTTEAVDAATAEKVFKQYANDNGVDGEWTYDDA

TKTFTVTEKPEVIDASELTPAVTTYKLVINGKTLKGETTTKAVDAETAEKAFKQYAN

DNGVDGVWTYDDATKTFTVTEMVTEVPGDAPTEPEKPEASIPLVPLTPATPIAKDDA

KKDDTKKEDAKKPEAKKDDAKKAET;

g.
(SEQ ID NO: 7)
KEETPETPETDSEEEVTIKANLIFANGSTQTAEFKGTFEKATSEAYAYADTLKK
DNGEYTVDVADKGYTLNIKFAG;

h
(SEQ ID NO: 8)
GYVS(R/H/K)(R/H)(P/S);

-continued i.
(SEQ ID NO: 9)
SDVQLQESGPDLVKPSQSLSLTCTVTGYSITSGYTWHWIRQFPGNKQEWGYIH

FSGYTNYNPSLKSRVSITRDTSKNQFFLHLNSVTTEDTATYYCARGDYGYEWFTY

WGQGTLVTVSADIQMTQSSSSFSVSLGDRVTITCKASEDIHNRLAWYKQKPGNAP

RLLISGATSLETGVPSRFSGSGSGKDYTLSITSLQNEDVATYYCQQYWIGPFTEGSG

TNLEIK;

j.
(SEQ ID NO: 10)
GYVSRHPGGGC;

k.
(SEQ ID NO: 11)
GYVSRHPGGGGS;

l.
(SEQ ID NO: 12)
FHENWPSGGGC;

m.
(SEQ ID NO: 13)
FHENWPSGGGGS;

n.
(SEQ ID NO: 14)
GVVTINP;

o.
(SEQ ID NO: 15)
GLVTPSG;

p.
(SEQ ID NO: 16)
GYVSHRS;

q.
(SEQ ID NO: 17)
KVWILTP;

r.
(SEQ ID NO: 18)
KLWVIPQ;

s.
(SEQ ID NO: 19)
GVSAGESVQITLPKNEVQLNAYVLQEPPKGETYTYDWQLITHPRDYSGEM

EGKHSQILKLSKLTPGLYEFKVIVEGQNAHGEGYVNVTVKPEPRKNRPPIAIVS

PQFQEISLPTTSTVIDGSQSTDDDKIVQYHWEELKGPLREEKISEDTAILKLSKLV

PGNYTFSLTVVDSDGATNSTTANLTVNKAVDYPPVANAGPNQVITLPQNSITLF

GNQSTDDHGITSYEWSLSPSSKGKVVEMQGVRTPTLQLSAMQEGDYTYQLTVT

DTIGQQATAQVTVIVQPENNKPPQADAGPDKELTLPVDSTTLDGSKSSDDQKIIS

YLWEKTQGPDGVQLENANSSVATVTGLQVGTYVFTLTVKDERNLQSQSSVNVI

VKEEINKPPIAKITGNVVITLPTSTAELDGSKSSDDKGIVSYLWTRDEGSPAAGEV

LNHSDHHPILFLSNLVEGTYTFHLKVTDAKGESDTDRTTVEVKPDPRG;

t.
(SEQ ID NO: 20)
SAGESVQITLPKNEVQLNAYVLQEPPKGETYTYDWQLITHPRDYSGEMEGK
HSQILKLSKLTPGLYEFKVIVEGQNAHGEGYVNVTVKPE;

u.
(SEQ ID NO: 21)
IAIVSPQFQEISLPTTSTVIDGSQSTDDDKIVQYHWEELKGPLREEKISEDTAIL
KLSKLVPGNYTESLTVVDSDGATNSTTANLTVNKA;

-continued v.
(SEQ ID NO: 22)
MGVSAGESVQITLPKNEVQLNAYVLQEPPKGETYTYDWQLITHPRDYSGEM

EGKHSQILKLSKLTPGLYEFKVIVEGQNAHGEGYVNVTVKPEPRKNRPPIAIVSPQ

FQEISLPTTSTVIDGSQSTDDDKIVQYHWEELKGPLREEKISEDTAILKLSKLVPGN

YTFSLTVVDSDGATNSTTANLTVNKA;

w.
(SEQ ID NO: 23)
VANAGPNQVITLPQNSITLFGNQSTDDHGITSYEWSLSPSSKGKVVEMQGVRT
PTLQLSAMQEGDYTYQLTVTDTIGQQATAQVTVIVQPE;

x.
(SEQ ID NO: 24)
QADAGPDKELTLPVDSTTLDGSKSSDDQKIISYLWEKTQGPDGVQLENANSS
VATVTGLQVGTYVFTLTVKDERNLQSQSSVNVIVKEE;

y.
(SEQ ID NO: 25)
IAKITGNVVITLPTSTAELDGSKSSDDKGIVSYLWTRDEGSPAAGEVLNHSDHH
PILFLSNLVEGTYTFHLKVTDAKGESDTDRTTVEVKPDP;
or z.
(SEQ ID NO: 26)
LAEAKVLANRELDKYGVSDYYKNLINNAKTVEGVKALIDEILAALP;

and the polypeptide with phase behavior comprises an amino acid
sequence selected from:
a.
(SEQ ID NO: 27)
$(GVGVP)_n$;

b.
(SEQ ID NO: 28)
$(GVGVPGLGVPGVGVPGLGVPGVGVP)_m$;

c.
(SEQ ID NO: 29)
$(GVGVPGVGVPGAGVPGVGVPGVGVP)_m$;

d.
(SEQ ID NO: 30)
$(GVGVPGWGVPGVGVPGWGVPGVGVP)_m$;

e.
(SEQ ID NO: 31)
$(GVGVPGVGVPGVGVPGVGVPGVGVPGVGVPGEGVPGFGVPGVGVP)_m$;

f.
(SEQ ID NO: 32)
$(GVGVPGVGVPGVGVPGVGVPGVGVPGVGVPGKGVPGFGVPGVGVP)_m$;
or g.
(SEQ ID NO: 33)
$GAGVPGVGVPGAGVPGVGVPGAGVP)_m$;

or a randomized, scrambled analog thereof;
wherein:
n is 20-120; and
m is 4-25.

A further aspect of the invention relates to a capture fusion protein comprising a secretion signal, at least one capture domain that specifically binds a biologic target, and at least one polypeptide with phase behavior.

An additional aspect of the invention relates to a capture fusion protein comprising at least one capture domain that specifically binds a biologic target and at least one polypeptide with phase behavior, wherein the biologic target is a cell or a virus particle.

Another aspect of the invention relates to a polynucleotide encoding the capture fusion protein of the invention, a vector comprising the polynucleotide of the invention, and a cell comprising the polynucleotide or the vector of the invention.

A further aspect of the invention relates to a method of purifying a biologic target from a composition, comprising:
 a. adding the capture fusion protein of the invention to the composition to capture the biologic target;
 b. triggering a phase transition and allowing the captured biologic target to aggregate;
 c. separating the aggregate from the composition; and
 d. eluting the biologic target from the capture fusion protein.

An additional aspect of the invention relates to a method of producing and purifying a biologic target, comprising:
 a. culturing the cell of the invention under conditions in which the capture fusion protein and the biologic target are expressed;

b. lysing the cells if the biologic target is expressed intracellularly or collecting the cell culture media if the biologic target is secreted;
c. triggering a phase transition to allow the captured biologic target to aggregate;
d. separating the aggregate from contaminants; and
e. eluting the biologic target from the capture fusion protein.

Another aspect of the invention relates to a method of producing and purifying a polypeptide of interest, comprising:
a. culturing the cell of the invention under conditions in which the capture fusion protein and the polypeptide of interest are expressed;
b. lysing the cells if the polypeptide of interest is expressed intracellularly or collecting the cell culture media if the polypeptide of interest is secreted;
c. triggering a phase transition to allow the captured polypeptide of interest to aggregate;
d. separating the aggregate from contaminants; and
e. eluting the polypeptide of interest from the capture fusion protein.

These and other aspects of the invention are set forth in more detail in the description of the invention below.

BRIEF DESCRIPTION OF THE DRAWINGS

(FIG. 14A) HERCEPTIN® (trastuzumab, IgG1); (FIG. 14B) XGEVA® (denosumab, IgG2); and (FIG. 14C) KEYTRUDA® (pembrolizumab, IgG4). Abbreviations: "CCH" cell culture harvest, "FT" flow through, "PS" phase separation, "SN" supernatant, "pel" pellet, "HC" heavy chain, LC "light chain".

(FIG. 15A) dsDNA by Biotium AccuClear assay, (FIG. 15B) HCP by Cygnus HEK293 assay, and (FIG. 15C) endotoxin by Charles River Endosafe® system.

FIGS. 25A-25B show antibody yields in each elution diavolume (FIG. 25A) and host cell protein (HCP) contaminant removal (FIG. 25B) in an optimized tangential flow filtration setup using $ELP_{1,80}$-Cap. Antibody yields are >90% with 3-log HCP removal.

FIG. 26 is an SDS-PAGE protein gel with Coomassie stain showing various dilutions of the starting material (1x to 1:10) as well as the AAV8 purified with the ELP-CapAAv material (far right two lanes). The final material is quite clean and has protein bands at the expected molecular weight of the AAV8 capsid proteins, VP1-3. Large molecular weight contaminants are no longer seen in the purified product.

DETAILED DESCRIPTION OF THE INVENTION

Figures 1A, 1B:
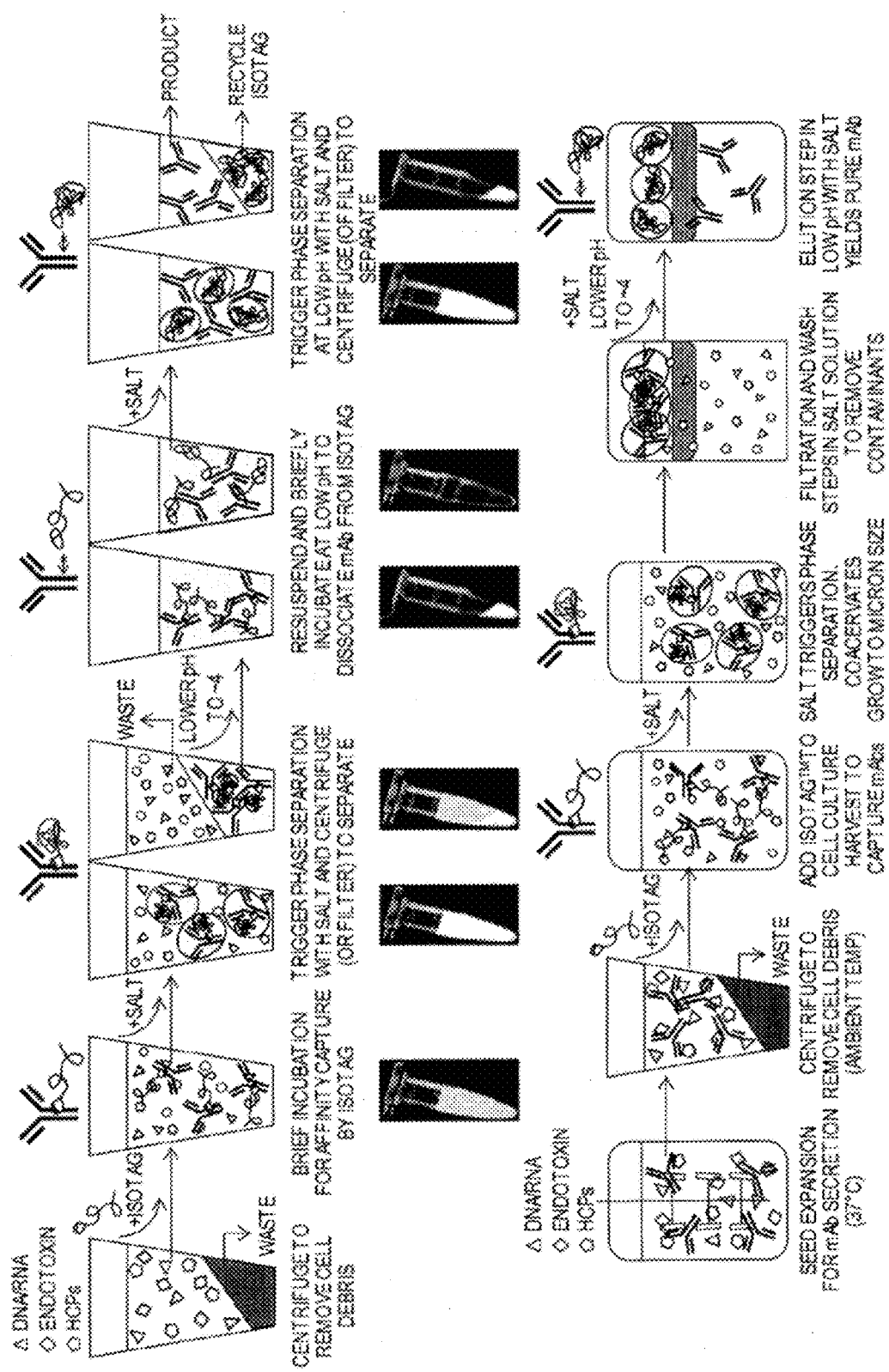
FIGS. 1A-1C are schematics showing one application of affinity/liquid-liquid phase separation for the purification of monoclonal antibodies from cell culture harvest using centrifugation (FIG. 1A), dead-end filtration (FIG. 1B), or tangential flow filtration (FIG. 1C).
Figure 1C:
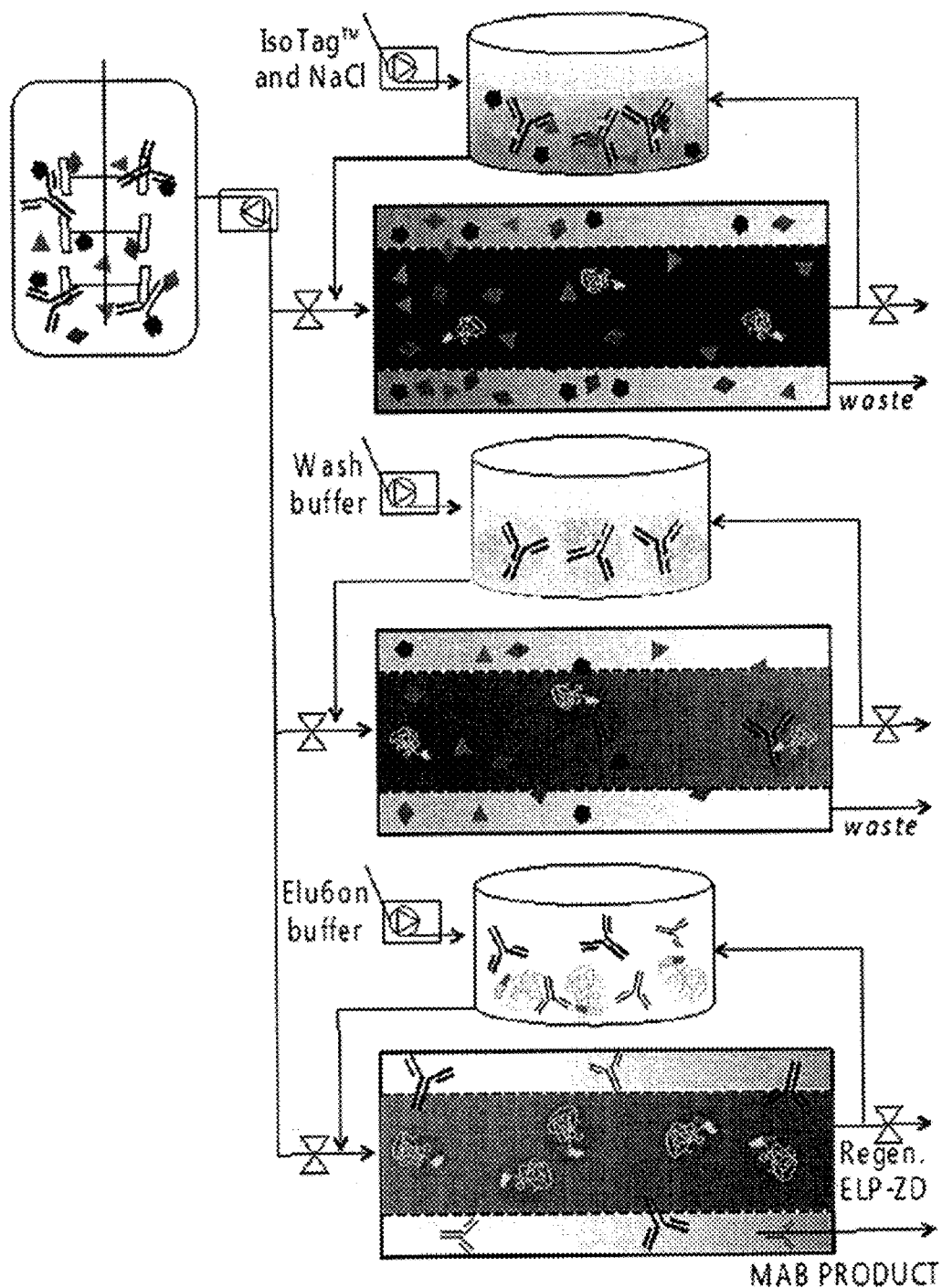

The present invention will now be described in more detail with reference to the accompanying drawings, in which preferred embodiments of the invention are shown. This invention may, however, be embodied in different forms and should not be construed as limited to the embodiments set forth herein. Rather, these embodiments are provided so that this disclosure will be thorough and complete, and will fully convey the scope of the invention to those skilled in the art.

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a complex comprises components A, B and C, it is specifically intended that any of A, B or C, or a combination thereof, can be omitted and disclaimed singularly or in any combination.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

Nucleotide sequences are presented herein by single strand only, in the 5' to 3' direction, from left to right, unless specifically indicated otherwise. Nucleotides and amino acids are represented herein in the manner recommended by the IUPAC-IUB Biochemical Nomenclature Commission, or (for amino acids) by either the one-letter code, or the three letter code, both in accordance with 37 C.F.R. § 1.822 and established usage.

Except as otherwise indicated, standard methods known to those skilled in the art may be used for cloning genes, amplifying and detecting nucleic acids, and the like. Such techniques are known to those skilled in the art. See, e.g., Sambrook et al., Molecular Cloning: A Laboratory Manual 2nd Ed. (Cold Spring Harbor, NY, 1989); Ausubel et al. Current Protocols in Molecular Biology (Green Publishing Associates, Inc. and John Wiley & Sons, Inc., New York).

As used in the description of the invention and the appended claims, the singular forms "a," "an," and "the" are intended to include the plural forms as well, unless the context clearly indicates otherwise.

Also as used herein, "and/or" refers to and encompasses any and all possible combinations of one or more of the associated listed items, as well as the lack of combinations when interpreted in the alternative ("or").

The term "about," as used herein when referring to a measurable value such as an amount of polypeptide, dose, time, temperature, enzymatic activity or other biological activity and the like, is meant to encompass variations of ±10%, ±5%, ±1%, ±0.5%, or even ±0.1% of the specified amount.

The transitional phrase "consisting essentially of means that the scope of a claim is to be interpreted to encompass the specified materials or steps recited in the claim, and those that do not materially affect the basic and novel characteristic(s) of the claimed invention.

The term "consists essentially of (and grammatical variants), as applied to a polynucleotide or polypeptide sequence of this invention, means a polynucleotide or polypeptide that consists of both the recited sequence (e.g., SEQ ID NO) and a total of ten or less (e.g., 1, 2, 3, 4, 5, 6, 7, 8, 9, or 10) additional nucleotides or amino acids on the 5' and/or 3' or N-terminal and/or C-terminal ends of the recited sequence such that the function of the polynucleotide or polypeptide is not materially altered. The total of ten or less additional nucleotides or amino acids includes the total number of additional nucleotides or amino acids on both ends added together. The term "materially altered," as applied to polynucleotides of the invention, refers to an increase or decrease in ability to express the encoded polypeptide of at least about 50% or more as compared to the expression level of a polynucleotide consisting of the recited sequence. The term "materially altered," as applied to polypeptides of the invention, refers to an increase or decrease in coagulation-stimulating activity of at least about 50% or more as compared to the activity of a polypeptide consisting of the recited sequence.

The term "enhance" or "increase" or grammatical variations thereof as used herein refers to an increase in the specified parameter of at least about 1.25-fold, 1.5-fold, 2-fold, 3-fold, 4-fold, 5-fold, 6-fold, 8-fold, 10-fold, twelve-fold, or even fifteen-fold.

The term "inhibit" or "reduce" or grammatical variations thereof as used herein refers to a decrease or diminishment in the specified level or activity of at least about 15%, 25%, 35%, 40%, 50%, 60%, 75%, 80%, 90%, 95% or more. In particular embodiments, the inhibition or reduction results in little or essentially no detectible activity (at most, an insignificant amount, e.g., less than about 10% or even 5%).

An "effective" amount as used herein is an amount that provides a desired effect.

As used herein, "nucleic acid," "nucleotide sequence," and "polynucleotide" are used interchangeably and encompass both RNA and DNA, including cDNA, genomic DNA, mRNA, synthetic (e.g., chemically synthesized) DNA or RNA and chimeras of RNA and DNA. The term polynucleotide, nucleotide sequence, or nucleic acid refers to a chain of nucleotides without regard to length of the chain. The nucleic acid can be double-stranded or single-stranded. Where single-stranded, the nucleic acid can be a sense strand or an antisense strand. The nucleic acid can be synthesized using oligonucleotide analogs or derivatives (e.g., inosine or phosphorothioate nucleotides). Such oligonucleotides can be used, for example, to prepare nucleic acids that have altered base-pairing abilities or increased resistance to nucleases. The present invention further provides a nucleic acid that is the complement (which can be either a full complement or a partial complement) of a nucleic acid, nucleotide sequence, or polynucleotide of this invention.

An "isolated polynucleotide" is a nucleotide sequence (e.g., DNA or RNA) that is not immediately contiguous with nucleotide sequences with which it is immediately contiguous (one on the 5' end and one on the 3' end) in the naturally occurring genome of the organism from which it is derived. Thus, in one embodiment, an isolated nucleic acid includes some or all of the 5' non-coding (e.g., promoter) sequences that are immediately contiguous to a coding sequence. The term therefore includes, for example, a recombinant DNA that is incorporated into a vector, into an autonomously replicating plasmid or virus, or into the genomic DNA of a prokaryote or eukaryote, or which exists as a separate molecule (e.g., a cDNA or a genomic DNA fragment produced by PCR or restriction endonuclease treatment), independent of other sequences. It also includes a recombinant DNA that is part of a hybrid nucleic acid encoding an additional polypeptide or peptide sequence. An isolated polynucleotide that includes a gene is not a fragment of a chromosome that includes such gene, but rather includes the coding region and regulatory regions associated with the gene, but no additional genes naturally found on the chromosome.

The term "fragment," as applied to a polynucleotide, will be understood to mean a nucleotide sequence of reduced length relative to a reference nucleic acid or nucleotide sequence and comprising, consisting essentially of, and/or consisting of a nucleotide sequence of contiguous nucleotides identical or almost identical (e.g., 90%, 92%, 95%, 98%, 99% identical) to the reference nucleic acid or nucleotide sequence. Such a nucleic acid fragment according to the invention may be, where appropriate, included in a larger polynucleotide of which it is a constituent. In some embodiments, such fragments can comprise, consist essentially of, and/or consist of oligonucleotides having a length of at least about 8, 10, 12, 15, 20, 25, 30, 35, 40, 45, 50, 75, 100, 150, 200, or more consecutive nucleotides of a nucleic acid or nucleotide sequence according to the invention.

The term "isolated" can refer to a nucleic acid, nucleotide sequence or polypeptide that is substantially free of cellular material, viral material, and/or culture medium (when produced by recombinant DNA techniques), or chemical precursors or other chemicals (when chemically synthesized). Moreover, an "isolated fragment" is a fragment of a nucleic acid, nucleotide sequence or polypeptide that is not naturally occurring as a fragment and would not be found in the natural state. "Isolated" does not mean that the preparation is technically pure (homogeneous), but it is sufficiently pure to provide the polypeptide or nucleic acid in a form in which it can be used for the intended purpose.

The term "fragment," as applied to a polypeptide, will be understood to mean an amino acid sequence of reduced length relative to a reference polypeptide or amino acid sequence and comprising, consisting essentially of, and/or consisting of an amino acid sequence of contiguous amino acids identical or almost identical (e.g., 90%, 92%, 95%, 98%, 99% identical) to the reference polypeptide or amino acid sequence. Such a polypeptide fragment according to the invention may be, where appropriate, included in a larger polypeptide of which it is a constituent. In some embodiments, such fragments can comprise, consist essentially of, and/or consist of peptides having a length of at least about 4, 6, 8, 10, 12, 15, 20, 25, 30, 35, 40, 45, 50, 75, 100, 150, 200, or more consecutive amino acids of a polypeptide or amino acid sequence according to the invention.

A "vector" is any nucleic acid molecule for the cloning of and/or transfer of a nucleic acid into a cell. A vector may be a replicon to which another nucleotide sequence may be attached to allow for replication of the attached nucleotide sequence. A "replicon" can be any genetic element (e.g., plasmid, phage, cosmid, chromosome, viral genome) that functions as an autonomous unit of nucleic acid replication in vivo, i.e., capable of replication under its own control. The term "vector" includes both viral and nonviral (e.g., plasmid) nucleic acid molecules for introducing a nucleic acid into a cell in vitro, ex vivo, and/or in vivo. A large number of vectors known in the art may be used to manipulate nucleic acids, incorporate response elements and promoters into genes, etc. For example, the insertion of the nucleic acid fragments corresponding to response elements and promoters into a suitable vector can be accomplished by ligating the appropriate nucleic acid fragments into a chosen vector that has complementary cohesive termini. Alternatively, the ends of the nucleic acid molecules may be enzymatically modified or any site may be produced by ligating nucleotide sequences (linkers) to the nucleic acid termini Such vectors may be engineered to contain sequences encoding selectable markers that provide for the selection of cells that contain the vector and/or have incorporated the nucleic acid of the vector into the cellular genome. Such markers allow identification and/or selection of host cells that incorporate and express the proteins encoded by the marker. A "recombinant" vector refers to a viral or non-viral vector that comprises one or more heterologous nucleotide sequences (i.e., transgenes), e.g., two, three, four, five or more heterologous nucleotide sequences.

Viral vectors have been used in a wide variety of gene delivery applications in cells, as well as living animal subjects. Viral vectors that can be used include, but are not limited to, retrovirus, lentivirus, adeno-associated virus, poxvirus, alphavirus, baculovirus, vaccinia virus, herpes virus, Epstein-Ban virus, and adenovirus vectors. Non-viral vectors include plasmids, liposomes, electrically charged lipids (cytofectins), nucleic acid-protein complexes, and biopolymers. In addition to a nucleic acid of interest, a vector may also comprise one or more regulatory regions, and/or selectable markers useful in selecting, measuring, and monitoring nucleic acid transfer results (delivery to specific tissues, duration of expression, etc.).

Vectors may be introduced into the desired cells by methods known in the art, e.g., transfection, electroporation, microinjection, transduction, cell fusion, DEAE dextran, calcium phosphate precipitation, lipofection (lysosome fusion), use of a gene gun, or a nucleic acid vector transporter (see, e.g., Wu et al., *J. Biol. Chem.* 267:963 (1992); Wu et al., *J. Biol. Chem.* 263:14621 (1988); and Hartmut et al., Canadian Patent Application No. 2,012,311, filed Mar. 15, 1990). In various embodiments, other molecules can be used for facilitating delivery of a nucleic acid in vivo, such as a cationic oligopeptide (e.g., WO95/21931), peptides derived from nucleic acid binding proteins (e.g., WO96/25508), and/or a cationic polymer (e.g, WO95/21931). It is also possible to introduce a vector in vivo as naked nucleic acid (see U.S. Pat. Nos. 5,693,622, 5,589,466 and 5,580,859). Receptor-mediated nucleic acid delivery approaches can also be used (Curiel et al., *Hum. Gene Ther.* 3:147 (1992); Wu et al., *J. Biol. Chem.* 262:4429 (1987)).

As used herein, the terms "protein" and "polypeptide" are used interchangeably and encompass both peptides and proteins, unless indicated otherwise.

A "fusion protein" is a polypeptide produced when two heterologous nucleotide sequences or fragments thereof coding for two (or more) different polypeptides not found fused together in nature are fused together in the correct translational reading frame.

As used herein, a "functional" polypeptide or "functional fragment" is one that substantially retains at least one biological activity normally associated with that polypeptide (e.g., protein binding, ligand or receptor binding). In particular embodiments, the "functional" polypeptide or "functional fragment" substantially retains all of the activities possessed by the unmodified peptide. By "substantially retains" biological activity, it is meant that the polypeptide retains at least about 20%, 30%, 40%, 50%, 60%, 75%, 85%, 90%, 95%, 97%, 98%, 99%, or more, of the biological activity of the native polypeptide (and can even have a higher level of activity than the native polypeptide). A "non-functional" polypeptide is one that exhibits little or essentially no detectable biological activity normally associated with the polypeptide (e.g., at most, only an insignificant amount, e.g., less than about 10% or even 5%). Biological activities such as protein binding can be measured using assays that are well known in the art and as described herein.

By the term "express" or "expression" of a polynucleotide coding sequence, it is meant that the sequence is transcribed, and optionally, translated. Typically, according to the present invention, expression of a coding sequence of the invention will result in production of the polypeptide of the invention. The entire expressed polypeptide or fragment can also function in intact cells without purification.

As used herein, a "transformed" or "transfected" cell is a cell that has been transformed, transduced and/or transfected with a nucleic acid molecule encoding polynucleotide or vector of this invention.

A first aspect of the invention relates to a method for preparing a capture fusion protein that is optimized for capturing and purifying a biologic target, the method comprising:
 a. preparing a capture fusion protein comprising at least one capture domain that specifically binds the biologic target and at least one polypeptide with phase behavior;
 b. determining one or more parameters under which the capture fusion protein captures the biologic target, the captured biologic target aggregates, the aggregate resolubilizes, and/or the biologic target elutes from the capture fusion protein;
 c. modifying the at least one capture domain that specifically binds the biologic target and/or the at least one polypeptide with phase behavior to alter the one or more parameters under which the capture fusion protein captures the biologic target, the captured biologic target aggregates, the aggregate resolubilizes, and/or the biologic target elutes from the capture fusion protein; and
 d. identifying a modified capture fusion protein that provides optimized parameters under which the capture fusion protein captures the biologic target, the captured biologic target aggregates, the aggregate resolubilizes, and/or the biologic target elutes from the capture fusion protein.

The parameters that may be determined may be any parameters that relate to purification of a biologic target and maintaining the viability and biological function of the biologic target. Examples of parameters that may be determined include, without limitation:
 a. temperature at which the capture fusion protein captures the biologic target, the captured biologic target aggregates, the aggregate resolubilizes, and/or the biologic target elutes from the capture fusion protein;
 b. ionic strength at which the capture fusion protein captures the biologic target, the captured biologic target aggregates, the aggregate resolubilizes, and/or the biologic target elutes from the capture fusion protein; and
 c. pH at which the capture fusion protein captures the biologic target, the captured biologic target aggregates, the aggregate resolubilizes, and/or the biologic target elutes from the capture fusion protein.

With respect to the parameter of temperature, in some embodiments, the capture fusion protein may be optimized such that it captures the biologic target, the captured biologic target aggregates, the aggregate resolubilizes, and/or the biologic target elutes from the capture fusion protein at a temperature that does not harm the biologic target, e.g., about room temperature, e.g., about 10° C. to about 40° C., e.g., about 15° C. to about 35° C., e.g., about 20° C. to about 30° C., e.g., about 10, 15, 20, 25, 30, 35, or 40° C. or any range therein.

With respect to ionic strength, in some embodiments, the capture fusion protein may be optimized such that it captures the biologic target, the captured biologic target aggregates, the aggregate resolubilizes, and/or the biologic target elutes from the capture fusion protein at a salt concentration that does not harm the biologic target, e.g., less than 1 M, e.g., about 0.1 M to about 0.8 M, e.g., about 0.1 M to about 0.6 M, e.g., about 0.1, 0.2, 0.3, 0.4, 0.5, 0.6, 0.7, 0.8, 0.9, or 1 M or any range therein.

With respect to pH, in some embodiments, the capture fusion protein may be optimized such that it captures the biologic target, the captured biologic target aggregates, the aggregate resolubilizes, and/or the biologic target elutes from the capture fusion protein at a pH that does not harm the biologic target, e.g., greater than 2 and/or less than 9, e.g., about 2 to about 6, e.g., about 8 to about 9 e.g., about 2, 2.5, 3, 3.5, 4, 4.5, 5, 5.5, 6, 6.5, 7, 7.5, 8.5, or 9 or any range therein.

The modification of the capture fusion protein may comprise alterations (e.g., additions, deletions, substitutions) to the amino acid sequence of any of the domains of the capture fusion protein. Exemplary modification include, without limitation:
 a. modifying the number of capture domains;
 b. modifying the affinity of the capture domain;
 c. modifying the sequence of the capture domain;

d. modifying the number of polypeptides with phase behavior;
e. modifying the number of repeats within the polypeptide with phase behavior; and
f. modifying the sequence of the polypeptide with phase behavior; or any combination thereof.

The capture fusion protein may be modified by altering the number of capture domains, e.g., by having 1, 2, 3, 4, 5, or more capture domains, thereby altering the number of biologic targets to which the capture fusion protein can bind and/or the affinity of the capture fusion protein for the biologic target.

The capture fusion protein may be modified by altering the affinity of the capture domain for the biologic target. The optimal affinity is one that provides specific binding to the capture domain sufficient to survive the phase transition but low enough that the biologic target can be eluted from the capture fusion protein under mild conditions.

The capture fusion protein may be modified by altering the sequence of the capture domain for the biologic target, e.g., by adding, deleting, or substituting amino acids. In some embodiments, the sequence is altered such that only a portion of the capture domain is present, which may alter the affinity of the capture domain for the biologic target. In some embodiments, the capture domain may be subjected to random mutagenesis to alter the affinity of the capture domain for the biologic target.

The capture fusion protein may be modified by altering the number of polypeptides with phase behavior, e.g., by having 1, 2, 3, 4, 5, or more of such polypeptides, thereby altering the parameters under which the phase transition occurs.

The capture fusion protein may be modified by altering the number of sequence repeats within the polypeptide with phase behavior, e.g., by having 2 to about 1000 repeats of the sequence, e.g., about 10 to about 500 repeats, e.g., about 20 to about 200 repeats, e.g, about 20 to about 120 repeats, e.g., about 2 to about 50 repeats, e.g., about 4 to about 25 repeats. In some embodiments, the number of repeats is dependent on the length of the repeat sequence, with shorter repeat sequences having a larger number of repeats. In some embodiments, each repeat has the same amino acid sequence. In some embodiments, the repeats may have different sequences, e.g., having 1 or 2 different amino acids between repeats.

The capture fusion protein may be modified by altering the sequence of the polypeptide with phase behavior, e.g., by adding, deleting, or substituting 1 or more amino acids within the polypeptide, e.g., 1, 2, 3, 4, or 5 or more amino acids. If there are multiple sequence repeats within the polypeptide with phase behavior, some or all of the repeats may have different sequences, e.g., some or all of the repeats may have the same alteration. In some embodiments, a certain percentage of the repeats have a particular sequence, e.g., 10, 20, 30, 40, 50, 60, 70, 80, or 90% of the repeats. In some embodiments, a certain percentage of the repeats have a different particular sequence, e.g., 10, 20, 30, 40, 50, 60, 70, 80, or 90% of the repeats. In some embodiments, a certain percentage of the repeats have a third, fourth or fifth different particular sequence, e.g., 10, 20, 30, 40, 50, 60, 70, 80, or 90% of the repeats. Examples include, without limitation, ELPs having a guest residue that is 40% Leu/60% Val, 100% Val, or 20% Ala/80% Val.

The optimization method may include characterizing the purified fusion protein and characterizing its phase behavior at concentrations that may range from 0.001 to 10 mM with added salt in concentrations that may range from 0 to 1 M in the following conditions: (1) capture buffer with and without the target biologic, (2) resolubilization buffer with and without the target biologic, and (3) in the elution conditions. This will enable determination of the amount of salt needed to trigger phase separation at room temperature. In some embodiments, the salt may be sodium chloride, sodium sulfate, ammonium sulfate, potassium sulfate, disodium phosphate, sodium citrate, or other kosmotropic salt that triggers phase separation.

The method may include an iterative procedure if needed, wherein adjustments are made to the polypeptide's molecular composition to tune its phase behavior if it is not optimally occurring at, or just above, ambient conditions. For example, if the transition temperature ($T_t$) of an ELP fused to a protein A capture domain is too high, the 'Xaa' guest residue composition can be modified to contain a higher percentage of more hydrophobic residues, to suppress the $T_t$ into the desired ambient range. Examples of suitable hydrophobic guest residues include valine, leucine, isoleucine, phenylalanine, tryptophan and methionine. Tyrosine, which is moderately hydrophobic, may also be used. Conversely, the $T_t$ can be increased by incorporating residues, such as those selected from the group consisting of: glutamic acid, cysteine, lysine, aspartate, alanine, asparagine, serine, threonine, arginine, and glutamine; preferably selected from alanine, serine, threonine and glutamic acid.

As another example, if the $T_t$ of an ELP fused to a capture domain is too high, the number of ELP repeats can be increased. If it is too low, the number of ELP repeats can be reduced.

As a further example, if the $T_t$ of an ELP fused to a capture domain is too low, the capture step can be conducted in a more dilute solution, as lowering the concentration raises the Tt.

The biologic target may be any biological material that it is desirable to purify. In some embodiments, the biologic target may be, without limitation, a polypeptide, a polynucleotide, a polysaccharide, a cell, or a virus particle (e.g., a protein or gene delivery vector). In some embodiments, the biologic target is an antibody, e.g., a monoclonal antibody, or a fragment thereof (e.g., a Fab, Fab', F(ab')$_2$, or scFv). In some embodiments, the biologic target is a virus particle and the capture domain specifically binds a polypeptide on the surface of the virus particle. In some embodiments, the virus particle is an adeno-associated virus particle and the capture domain specifically binds a capsid protein. In some embodiments, the capture domain is a phage-derived peptide, such as HEPTAPEPTIDE or all or part of a native protein known to bind the virus particle, such as the AAV receptor, e.g., the PKD1 and/or PKD2 domains of the AAV receptor. In some embodiments, the biologic target is a cell and the capture domain specifically binds a polypeptide on the surface of the cell.

The capture domain may be any suitable domain that specifically bind the biologic target. The capture domain may be, without limitation, an antibody-binding protein, an antibody, an antigen, or an artificial affinity protein. In some embodiments, the capture domain is protein A or a domain thereof, protein G or a domain thereof, or protein L or a domain thereof.

In some embodiments, the capture domain is domain Z derived from protein A. The Z domain is a 58-residue binding protein derived from the B domain of staphylococcal Protein A that binds most isotypes of IgG from various species with nanomolar affinity This cysteine-free protein is attractive for its small size, rapid folding, high bacterial expression, and enhanced chemical stability, which are a result of mutations introduced at key positions. The affinity of the Z domain for antibodies is abolished under low pH conditions. With the present invention, at low pH, the non-covalent bonds between the Z domain and monoclonal antibodies are broken, allowing for separate recovery of the purified biologic target and the capture fusion protein.

In some embodiments, the affinity capture component is selected from a library, such as phage-display, to select a peptide or protein with nanomolar to low micromolar affinity for the target.

Artificial affinity proteins (artificial scaffold proteins) can act as ligands of immunoglobulins. Examples include, without limitation, the Z domain, affitins (variants of Sac7d, Sso7d), carbohydrate-binding module variants, designed Ankyrin repeat proteins (DARPins), cystine knot miniproteins (knottins), fibronectin type III domain (monobody), and computationally-designed IgG-binding proteins.

The phase separating polypeptide may be any amino acid sequence that provides phase transition characteristics to the capture fusion protein. In some embodiments, the phase separating polypeptide is an elastin-like polypeptide (ELP), a polymer of the tropoelastin-derived pentapeptide motif: Val-Pro-Gly-Xaa-Gly (SEQ ID NO:34), where Xaa can be any amino acid except Pro. In other embodiments, the phase separating polypeptide may be randomized versions of the ELP sequence with identical or similar amino acids compositions (e.g., at least 80%, 85%, 90%, 91%, 92%, 93%, 94%, 95%, 6%, 97%, 98%, or 99% identical amino acid composition).

The guest residue X may be any amino acid that does not eliminate the phase transition characteristics of the ELP. X may be a naturally occurring or non-naturally occurring amino acid. For example, X may be selected from the group consisting of: alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine and valine. X may be a non-classical amino acid. Examples of non-classical amino acids include: D-isomers of the common amino acids, 2,4-diaminobutyric acid, α-amino isobutyric acid, 4-aminobutyric acid, Abu, 2-amino butyric acid, γ-Abu, ε-Ahx, 6-amino hexanoic acid, Aib, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, β-alanine, fluoro-amino acids, designer amino acids such as β-methyl amino acids, Cα-methyl amino acids, Na-methyl amino acids, and amino acid analogs in general.

ELPs display lower critical solution temperature (LCST) phase behavior whereby they undergo liquid-liquid phase separation with the addition of heat or, isothermally, with the addition of salt. Once the phase separation is triggered, the complexed biologic will form dense, liquid droplets that can be separated from the soluble contaminants (1) passively by allowing the denser droplets to settle, (2) by centrifugation, or (3) by filtration with a membrane whose pore sizes retain the micron-scale coacervates. In one example, an ELP is fused to a single domain from Protein A, which is a protein from Staphylococcal aureus that binds the constant region of antibodies. This fusion has been strategically designed to have phase behavior just above room temperature. The temperature at which phase separation occurs (the transition temperature, Tt) can be tuned by manipulating the number of pentapeptide repeats in the ELP or the molecular composition of the 'Xaa' residue.

ELPs exhibit LCST phase behavior, undergoing a reversible phase transition from a soluble to insoluble phase above their cloud point temperature (also called inverse transition temperature, $T_t$). The $T_t$ can be precisely tuned by adjusting intrinsic factors such as molecular weight (number of VPGXG (SEQ ID NO:34) repeats) and guest residue composition. The $T_t$ can also be tuned by manipulating solution conditions, such as pH, salt type, and salt concentration. Adding kosmotropic salts such as NaCl or $(NH_4)_2SO_4$ is a convenient way to isothermally trigger the LCST phase transition of ELPs by depressing the $T_t$ below a specified temperature of interest, which in this context would be the desired operating temperature of the standard biologic target purification process. When added to a solution containing ELP, these salts enhance water-water interactions and remove the hydration shielding of the ELP's hydrophobic residues. This reduces the ELP's solubility and causes it to undergo a liquid-liquid phase separation, similar to oil-in-water behavior.

In inverse transition cycling, the addition of salt lowers the LCST below a desired temperature (typically ambient temperature) and causes the ELP fusion to become insoluble, phase separating from water without unfolding or damaging the fused protein of interest. This phase separation allows it to be isolated from other soluble contaminant molecules by unit operations like centrifugation or microfiltration. Because the LCST phase transition of ELPs and ELP fusions is completely reversible, this isolated insoluble phase (containing the ELP fusion) can be subsequently resolubilized and concentrated by adding a small volume of buffer with low salt concentration or by lowering the operating temperature below the Tt. The resolubilized fusion can be centrifuged again, this time removing any insoluble contaminants. Repetition of these steps provides a simple, non-chromatographic method for the purification of proteins. Classically, ELPs have been expressed in E. coli. However, more recent studies have published on the expression of ELP fusions in mammalian cells.

In some embodiments, the ELP may be a diblock ELP, comprised of a soluble ELP block fused to an insoluble ELP block. The diblock's inherent amphiphilicity will cause self-assembly into nanoparticles rather than coacervation in the cell, which could improve its progress through the secretion pathway. The multivalent nanoparticle will then bind the biologic target and, if the biologic has multiple binding sites, form a gel-like network that can be leveraged for purification.

In some embodiments, the phase separating polypeptide is derived from other biologically inspired molecules with phase behavior, such as resilin.

In some embodiments, the phase separating polypeptide is a non-repetitive polypeptide derived from a target ELP sequence, with its molecular composition kept constant, but its sequence scrambled. In some embodiments, the non-repetitive polypeptide is selected from a library of peptide polymers with rationally designed compositions.

The phase separating polypeptide may comprise a non-repetitive unstructured polypeptide. In some embodiments, the non-repeated unstructured polypeptide comprises a sequence of at least 60 amino acids, wherein at least about 10% (e.g., at least about 10%, 15%, 20%, 25%, 30%, 35%, 40%, 45%, or 50%) of the amino acids are proline (P), and wherein at least about 20% (e.g., at least about 20%, 25%, 30%, 35%, 40%, 45%, 50%, 55%, or 60%) of the amino acids are glycine (G). In some embodiments, the non-repeated unstructured polypeptide comprises a sequence wherein at least about 40% (e.g., at least about 40%, 45%, 50%, 55%, 60%, 65%, or 70%) of the amino acids are selected from the group consisting of valine (V), alanine (A), leucine (L), lysine (K), threonine (T), isoleucine (I), tyrosine (Y), serine (S), and phenylalanine (F). In some embodiments, the non-repeated unstructured polypeptide comprises a sequence that does not contain three contiguous identical amino acids, wherein any 5-10 amino acid subsequence does not occur more than once in the non-repeated unstructured polypeptide, and wherein when the non-repeated unstructured polypeptide comprises a subsequence starting and ending with proline (P), the subsequence further comprises at least one glycine (G). In some embodiments, the non-repeated unstructured polypeptide comprises a sequence of at least 60 amino acids, wherein at least about 10% of the amino acids are proline (P), wherein at least about 20% of the amino acids are glycine (G), wherein at least about 40% of the amino acids are selected from the group consisting of valine (V), alanine (A), leucine (L), lysine (K), threonine (T), isoleucine (I), tyrosine (Y), serine (S), and phenylalanine (F), wherein the sequence does not contain three contiguous identical amino acids, wherein any 5-10 amino acid subsequence does not occur more than once in the non-repeated unstructured polypeptide, and wherein when the non-repeated unstructured polypeptide comprises a subsequence starting and ending with proline (P), the subsequence further comprises at least one glycine (G).

In certain embodiments, the capture fusion protein may further comprise a spacer sequence between the at least one capture domain that specifically binds the biologic target and the at least one polypeptide with phase behavior. In some embodiments, the spacer sequence comprises from one to about twenty-six amino acids, e.g., about 1, 2, 3, 4, 5, 6, 7, 8, 9, 10, 12, 14, 16, 18, 20, 22, 24, or 26 amino acids or any range therein. In some embodiments, the spacer sequence comprises at least one proline.

A further aspect of the invention relates to a capture fusion protein made by the optimization method of the invention.

Another aspect of the invention relates to a capture fusion protein comprising at least one capture domain that specifically binds the biologic target and at least one polypeptide with phase behavior, wherein the capture domain comprises, consists essentially of, or consists of an amino acid sequence selected from:

a.
(SEQ ID NO: 1)
VDNKFNKEQQNAFYEILHLPNLNEEQRNAFIQSLKDDPSQSANLLAEAKKLN
DAQAPK;

b.
(SEQ ID NO: 2)
VDNKFNKEQQNAFYEILSLPNLNEEQRAAFIQSLKDDPSQSANLLAEAKKLN
DAQAPKG;

c.
(SEQ ID NO: 3)
VDNKFNKEHQNAFYEILHLPNLNEEQRNAFIQSLKHDPSQSANLLAEAKKLN
DAQAPKG;

d.
(SEQ ID NO: 4)
AQHDEAQQNAFYQVLNMPNLNADQRNGFIQSLKDDPSQSANVLGEAQKLN

DSQAPKADAQQNKFNKDQQSAFYEILNMPNLNEEQRNGFIQSLKDDPSQSTNVLGE

AKKLNESQAPKADNNFNKEQQNAFYEILNMPNLNEEQRNGFIQSLKDDPSQSANLL

AEAKKLNESQAPKADNKFNKEQQNAFYEILHLPNLNEEQRNGFIQSLKDDPSQSAN

LLAEAKKLNDAQAPKADNKFNKEQQNAFYEILHLPN;

e.
(SEQ ID NO: 5)
TYKLILNGKTLKGETTTEAVDAATAEKVFKQYANDNGVDGEWTYDDATKT
FTVTEG;

f.
(SEQ ID NO: 6)
KTDTYKLILNGKTLKGETTTEAVDAATAEKVFKQYANDNGVDGEWTYDDA

TKTFTVTEKPEVIDASELTPAVTTYKLVINGKTLKGETTTKAVDAETAEKAFKQYAN

DNGVDGVWTYDDATKTFTVTEMVTEVPGDAPTEPEKPEASIPLVPLTPATPIAKDDA

KKDDTKKEDAKKPEAKKDDAKKAET;

g.
(SEQ ID NO: 7)
KEETPETPETDSEEEVTIKANLIFANGSTQTAEFKGTFEKATSEAYAYADTLKK
DNGEYTVDVADKGYTLNIKFAG;

h
(SEQ ID NO: 8)
GYVS(R/H/K)(R/H)(P/S);

-continued i.
(SEQ ID NO: 9)
SDVQLQESGPDLVKPSQSLSLTCTVTGYSITSGYTWHWIRQFPGNKQEWGYIH

FSGYTNYNPSLKSRVSITRDTSKNQFFLHLNSVTTEDTATYYCARGDYGYEWFTY

WGQGTLVTVSADIQMTQSSSSFSVSLGDRVTITCKASEDIHNRLAWYKQKPGNAP

RLLISGATSLETGVPSRFSGSGSGKDYTLSITSLQNEDVATYYCQQYWIGPFTEGSG

TNLEIK;

j.
(SEQ ID NO: 10)
GYVSRHPGGGC;

k.
(SEQ ID NO: 11)
GYVSRHPGGGGS;

l.
(SEQ ID NO: 12)
FHENWPSGGGC;

m.
(SEQ ID NO: 13)
FHENWPSGGGGS;

n.
(SEQ ID NO: 14)
GVVTINP;

o.
(SEQ ID NO: 15)
GLVTPSG;

p.
(SEQ ID NO: 16)
GYVSHRS;

q.
(SEQ ID NO: 17)
KVWILTP;

r.
(SEQ ID NO: 18)
KLWVIPQ;

s.
(SEQ ID NO: 19)
GVSAGESVQITLPKNEVQLNAYVLQEPPKGETYTYDWQLITHPRDYSGEM

EGKHSQILKLSKLTPGLYEFKVIVEGQNAHGEGYVNVTVKPEPRKNRPPIAIVS

PQFQEISLPTTSTVIDGSQSTDDDKIVQYHWEELKGPLREEKISEDTAILKLSKLV

PGNYTFSLTVVDSDGATNSTTANLTVNKAVDYPPVANAGPNQVITLPQNSITLF

GNQSTDDHGITSYEWSLSPSSKGKVVEMQGVRTPTLQLSAMQEGDYTYQLTVT

DTIGQQATAQVTVIVQPENNKPPQADAGPDKELTLPVDSTTLDGSKSSDDQKIIS

YLWEKTQGPDGVQLENANSSVATVTGLQVGTYVFTLTVKDERNLQSQSSVNVI

VKEEINKPPIAKITGNVVITLPTSTAELDGSKSSDDKGIVSYLWTRDEGSPAAGEV

LNHSDHHPILFLSNLVEGTYTFHLKVTDAKGESDTDRTTVEVKPDPRG;

t.
(SEQ ID NO: 20)
SAGESVQITLPKNEVQLNAYVLQEPPKGETYTYDWQLITHPRDYSGEMEGK
HSQILKLSKLTPGLYEFKVIVEGQNAHGEGYVNVTVKPE;

u.
(SEQ ID NO: 21)
IAIVSPQFQEISLPTTSTVIDGSQSTDDDKIVQYHWEELKGPLREEKISEDTAIL
KLSKLVPGNYTESLTVVDSDGATNSTTANLTVNKA;

-continued v.
(SEQ ID NO: 22)
MGVSAGESVQITLPKNEVQLNAYVLQEPPKGETYTYDWQLITHPRDYSGEM

EGKHSQILKLSKLTPGLYEFKVIVEGQNAHGEGYVNVTVKPEPRKNRPPIAIVSPQ

FQEISLPTTSTVIDGSQSTDDDKIVQYHWEELKGPLREEKISEDTAILKLSKLVPGN

YTFSLTVVDSDGATNSTTANLTVNKA;

w.
(SEQ ID NO: 23)
VANAGPNQVITLPQNSITLFGNQSTDDHGITSYEWSLSPSSKGKVVEMQGVRT
PTLQLSAMQEGDYTYQLTVTDTIGQQATAQVTVIVQPE;

x.
(SEQ ID NO: 24)
QADAGPDKELTLPVDSTTLDGSKSSDDQKIISYLWEKTQGPDGVQLENANSS
VATVTGLQVGTYVFTLTVKDERNLQSQSSVNVIVKEE;

y.
(SEQ ID NO: 25)
IAKITGNVVITLPTSTAELDGSKSSDDKGIVSYLWTRDEGSPAAGEVLNHSDHH
PILFLSNLVEGTYTFHLKVTDAKGESDTDRTTVEVKPDP;
or z.
(SEQ ID NO: 26)
LAEAKVLANRELDKYGVSDYYKNLINNAKTVEGVKALIDEILAALP.

An additional aspect of the invention relates to a capture fusion protein comprising at least one capture domain that specifically binds the biologic target and at least one polypeptide with phase behavior, wherein the polypeptide with phase behavior comprises, consists essentially of, or consists of an amino acid sequence selected from:

a.
(SEQ ID NO: 27)
$(GVGVP)_n$;

b.
(SEQ ID NO: 28)
$(GVGVPGLGVPGVGVPGLGVPGVGVP)_m$;

c.
(SEQ ID NO: 29)
$(GVGVPGVGVPGAGVPGVGVPGVGVP)_m$;

d.
(SEQ ID NO: 30)
$(GVGVPGWGVPGVGVPGWGVPGVGVP)_m$;

e.
(SEQ ID NO: 31)
$(GVGVPGVGVPGVGVPGVGVPGVGVPGVGVPGEGVPGFGVPGVGVP)_m$;

f.
(SEQ ID NO: 32)
$(GVGVPGVGVPGVGVPGVGVPGVGVPGVGVPGKGVPGFGVPGVGVP)_m$;
or g.
(SEQ ID NO: 33)
$GAGVPGVGVPGAGVPGVGVPGAGVP)_m$;

or a randomized, scrambled analog thereof;
wherein:
n is 20-120; and
m is 4-25.
In some embodiments, n is 10-40, 40-60, 60-80, 80-100, 100-120, 20-50, 50-80, 80-120, 20-60, 60-100, 10-70, 70, 120, 10-80, 80-120, at least 10, 20, 30, 40, 50, 60, 70, 80, 90, or 100, and/or less than 120, 120, 100, 90, 80, 70, 60, 50, 40, or 30 or any range therein. In some embodiments, m is 4-10, 10-15, 15-20, 20-25, 4-15, 15-25, 4-20, 10-25, at least, 4, 5, 6, 7, 8, 9, 10, 11, 12, 13, 14, 15, 16, 17, 18, 19, or 20 and/or less than 25, 24, 23, 22, 21, 20, 19, 18, 17, 16, 15, 14, 13, 12, 11, or 10 or any range therein.

In some embodiments, the capture fusion protein comprises the capture domain of one of SEQ ID NOS:1-26 and the polypeptide with phase behavior of one of SEQ ID NOS:27-33.

A further aspect of the invention relates to a capture fusion protein that can be secreted from the cell in which it is produced, e.g., a mammalian cell. In one embodiment, the capture fusion protein comprises a secretion signal (e.g., a signal peptide), at least one capture domain that specifically binds a biologic target, and at least one polypeptide with phase behavior. The secretion signal will typically be located on the N-terminus of the capture fusion protein and is typically less than 50 amino acids in length, e.g., about 15-30 amino acids in length. The secretion signal my be any known secretion signal including, without limitation, mammalian signals such as tropoelastin, azurocidin, insulin, luciferase, albumin, chymotrypsinogen, trypsinogen-2, interleukin-2, or BM40, bacterial signals such as OmpA or PelB, and yeast signals such as alpha amylase or full length alpha factor. In some embodiments, the secretion signal may be a synthetic signal. The biologic target of the capture fusion protein may be any of the biologic targets described herein. The capture domain that specifically binds a biologic target and the polypeptide with phase behavior may be any of the domains and sequences described herein.

Another aspect of the invention relates to a capture fusion protein comprising at least one capture domain that specifically binds a biologic target and at least one polypeptide with phase behavior, wherein the biologic target is a cell or a virus particle. In some embodiments, the cell or virus particle comprises multiple binding sites for the capture fusion protein, e.g., at least about 5, 10, 15, 20, 25, 30, 35, 40, 45, or 50 or more binding sites. The biologic target of the capture fusion protein may be any of the cell or viral biologic targets described herein. The capture domain that specifically binds a biologic target and the polypeptide with phase behavior may be any of the domains and sequences described herein.

The present invention described herein presents a novel method for AAV purification of viral particles such as AAV that combines affinity capture with liquid-liquid phase separation by genetically fusing and recombinantly expressing a capture domain with a stimulus-responsive polypeptide. Although affinity-based phase separation has been used to purify biologic proteins, these proteins have been relatively small (>200 kDa) and only have 1-2 binding sites. In contrast, AAVs are comprised of 60 or more subunits that are themselves 60-80 kDa. Thus, the application of affinity capture with liquid-liquid phase separation is significantly different than the more simplistic single protein purification done to date.

Because they are made up of 60 subunits, the size of this target is much larger and it has many copies of that target to which the capture domain will bind. During the affinity capture step, the virus particle will be coated in the fusion protein. The multivalency, high local concentration, and very large total molecular weight of the complex will have significant effects on the phase transition temperature ($T_t$), or cloud point. Self-assembly diblock ELPs demonstrate nearly concentration-independent phase behavior and large molecular weights can substantially lower the cloud point.

An additional aspect of the invention relates to a polynucleotide encoding the capture fusion protein of the invention. In some embodiments, the polynucleotide is codon optimized for expression in a particular host cell. For example, the polynucleotide may be optimized for expression in *E. coli*, human, mouse, hamster, or insect cells. In some embodiments, the polynucleotide is part of an expression cassette for production of the capture fusion protein. The expression cassette may further comprise expression elements useful for increasing expression of the capture fusion protein. The need for such control sequences will vary depending upon the host cell selected and the transformation method chosen. Generally, control sequences include a transcriptional promoter, an optional operator sequence to control transcription, a sequence encoding suitable mRNA ribosomal binding sites, and sequences that control the termination of transcription and translation.

In some embodiments, the polynucleotide of the invention is operably linked to a promoter. The promoter may be a constitutive promoter, an inducible promoter, or a tissue-specific or tissue-preferred promoter. In some embodiments, the polynucleotide of the invention is operably linked to a polyadenylation element. In some embodiments, the polynucleotide is part of an expression cassette comprising, consisting essentially of, or consisting of the polynucleotide operably linked to a promoter and a polyadenylation element.

Another aspect of the invention relates to a vector comprising the polynucleotides of the invention. Suitable vectors include, but are not limited to, a plasmid, phage, viral vector (e.g., an AAV vector, adenovirus vector, herpesvirus vector, alphavirus, or baculovirus vector), bacterial artificial chromosome (BAC), or yeast artificial chromosome (YAC). In some embodiments, the vector further comprises a polynucleotide encoding a polypeptide of interest. In some embodiments, the polypeptide of interest is an antibody, e.g., a monoclonal antibody, or a fragment thereof.

A further aspect of the invention relates to a cell comprising the polynucleotide or vector of the invention. In some embodiments, the cell is stably transformed or transfected with the polynucleotide or the vector of the invention. The cell may be any cell suitable for production of the capture fusion protein. Suitable host cells include prokaryote, yeast, or higher eukaryotic cells such as mammalian cells and insect cells. Examples of useful mammalian host cell lines are VERO and HeLa cells, Chinese hamster ovary (CHO) cell lines, and W1138, HEK 293, BHK, COS-7, CV, and MDCK cell lines.

Host cells such as insect cells (e.g., cultured *Spodoptera frugiperda* cells) and expression vectors such as the baculovirus expression vector (e.g., vectors derived from *Autographa californica* MNPV, *Trichoplusia ni* MNPV, *Rachiplusia ou* MNPV, or *Galleria ou* MNPV) may be employed.

Prokaryote host cells include gram negative or gram positive organisms, for example *Escherichia coli* (*E. coli*) or bacilli, respectively. Higher eukaryotic cells include established cell lines of mammalian origin as described herein. Exemplary bacterial host cells are *E. coli* W3110 (ATCC 27,325), *E. coli* B, *E. coli* X1776 (ATCC 31,537) and *E. coli* 294 (ATCC 31,446). A broad variety of suitable prokaryotic and microbial vectors are available.

Eukaryotic microbes such as yeast cultures may also be transformed with protein-encoding vectors. *Saccharomyces cerevisiae* is the most commonly used among lower eukaryotic host microorganisms, although a number of other strains are commonly available.

In some embodiments, the cell expressing the capture fusion protein also expresses the biologic target. Thus, the cell may further comprise a heterologous polynucleotide encoding the biologic target, e.g., a polypeptide of interest. In some embodiments, the polypeptide of interest is an antibody, e.g., a monoclonal antibody, or a fragment thereof One aspect of the invention relates to a method of preparing a capture fusion protein for the purification of biologics. The method may include (a) transforming a cell with a recombinant expression vector carrying a polynucleotide encoding the polypeptide with phase behavior fused to a polynucleotide encoding the capture domain and (b) culturing the transformed cell to express the first and second polypeptides as a single fusion protein. In some embodiments, the method further includes (c) isolating the capture fusion protein. In some embodiments, the cell is a bacterial cell, e.g., *E. coli*. In some embodiments, the bacteria is cultured in media comprising an antibiotic.

The method may include transfecting a mammalian cell with a recombinant expression vector carrying a polynucleotide encoding the polypeptide with phase behavior fused to a polynucleotide encoding the capture domain, as well as a selection marker. In some embodiments, this method may further include (a) selecting a stably transfected cell line with optimal expression, (b) culturing the stably transfected mammalian cell to express the capture fusion protein, and (c) isolating the capture fusion protein. In some embodiments, the mammalian cells comprise human embryonic kidney (HEK) cells or Chinese hamster ovary (CHO) cells. In some embodiments, the cells are cultured in media comprising a selection chemical, such as an antibiotic.

In some embodiments, the vector also encodes a single antibiotic selection marker. In some embodiments, the polynucleotide may also encode a leader sequence to promote better expression, a signal peptide to direct the fusion to a specific cellular location that makes isolation easier, or a linker between the phase sensitive biopolymer and the affinity domain to improve target capture and minimize steric hindrance.

An additional aspect of the invention relates to methods of purifying a biologic target using the capture fusion proteins of the invention. The methods rely on phase transition and separation. The phase of the polypeptide may be described as, for example, soluble or an aggregate. The aggregate may be a variety of forms depending on the sequence of the polypeptide and the capture domain to which it is fused. The aggregate may be a self-assembled micelle, a rod-like structure, a sheet, a coacervated liquid droplet, or a combination thereof. The aggregates may be of a variety of sizes, depending on the phase, temperature, and time in transitioned state. The aggregate may be, for example, nanoscale aggregates, micron-sized aggregates, or macroscale aggregates.

One aspect of the invention is a method of purifying a biologic target from a composition, comprising:
a. adding the capture fusion protein of the invention to the composition to capture the biologic target;
b. triggering a phase transition and allowing the captured biologic target to aggregate;
c. separating the aggregate from the composition; and
d. eluting the biologic target from the capture fusion protein.

The composition may be, for example, cell lysate from cells cultured to produce the biologic target. If the biologic target is secreted from the cultured cells, the composition may be the culture medium in which the cells were grown.

Another aspect of the invention relates to a method of producing and purifying a biologic target, comprising:
a. culturing the cell of the invention under conditions in which the capture fusion protein and the biologic target are expressed;
b. lysing the cells if the biologic target is expressed intracellularly or collecting the cell culture media if the biologic target is secreted;
c. triggering a phase transition to allow the captured biologic target to aggregate;
d. separating the aggregate from contaminants; and
e. eluting the biologic target from the capture fusion protein.

A further aspect of the invention relates to a method of producing and purifying a polypeptide of interest, comprising:
a. culturing the cell of the invention under conditions in which the capture fusion protein and the polypeptide of interest are expressed;
b. lysing the cells if the polypeptide of interest is expressed intracellularly or collecting the cell culture media if the polypeptide of interest is secreted;
c. triggering a phase transition to allow the captured polypeptide of interest to aggregate;
d. separating the aggregate from contaminants; and
e. eluting the polypeptide of interest from the capture fusion protein.

In each of the purification methods of the invention, the separating step may be carried out, for example, by centrifugation, microfiltration, or flocculation. The microfiltration may be, for example, tangential flow filtration or normal flow filtration.

In some embodiments, the eluting step is carried out by triggering a phase transition and separating the capture fusion protein from the biologic target.

Having described the present invention, the same will be explained in greater detail in the following examples, which are included herein for illustration purposes only, and which are not intended to be limiting to the invention.

EXAMPLE 1

Materials and Methods

The pETDuet-1 vector was purchased from EMD Millipore (Billerica, MA). All the restriction enzymes, ligase, and corresponding buffers were purchased from New England Biolabs (Ipswich, MA). Chemically competent Eb5alpha and BL21(DE3) cells were purchased from Edge Bio (Gaithersburg, MD). DNA extraction and purification kits were purchased from Qiagen (Valencia, CA). Terrific broth medium (TB) was purchased from Amresco (Solon, OH). Isopropyl β-D-1-thiogalactopyranoside (IPTG) was purchased from Bioline USA (Boston, MA). Alexa Fluor® NHS ester dyes and anhydrous dimethyl sulfoxide (DMSO) were purchased from Thermo Fisher Scientific (Waltham, MA). Deionized water was obtained from a Milli-Q® system (Thermo Scientific, CA).

Gene Synthesis

Construction of the Fusion Protein Expression Vector. A pET24 vector was obtained from EMD Millipore. This vector contains a kanamycin resistance gene and a multiple cloning sites (MCS) preceded by a T7 promoter, lac operator, and ribosomal binding site. Codon optimized genes were purchased from Integrated DNA Technologies and coded for an MSK leader, a capture domain (Cap), or small 5-mer ELPs with varied molecular compositions such as:

(VPGVG)5 (SEQ ID NO: 35), (VPGVGVPGLGVPGVGVPGLGVPGVG (SEQ ID NO: 36)),
and (VPGVGVPGVGVPGAGVPGVGVPGVG (SEQ ID NO: 37)).

These genes contained recognition sequences for the BseRI and AcuI Type Its restriction enzymes, to facilitate seamless cloning, as well as NdeI and BamHI cut sites for insertion into the pET24 vector. After inserting each gene into separate vectors, the ELP was recursively ligated to itself to create a longer peptide polymer ranging from 20- to 120-mers of the pentapeptide Val-Pro-Gly-Xaa-Gly (VPGXG) (SEQ ID NO:34). The genes were then ligated to the capture domain and the MSK leader sequence. At each step of this cloning, the ligated DNA was transformed into EB5alpha (25 µL) competent cells (EdgeBio) and spread onto agar plates containing 45 µg/mL kanamycin. Positive clones were identified with Sanger sequencing (Eton Biosciences) using the universal T7 Promoter or T7 Reverse primers. Final fusion constructs were transformed into BL21(DE3) competent cells (EdgeBio) for expression.

Construction of the Fusion Protein Expression Vector. The genes for codon optimized heavy and light chains for HERCEPTIN®, XGEVA®, and KEYTRUDA® were purchased as gBlocks from Integrated DNA Technologies. This cDNA was preceded by a gene for the azurocidin secretion signal and then flanked by 15-50 nucleotides that corresponded to the MCS of the pcDNA5 vector. After cutting and gel purifying the pcDNA5 vector with NheI and XhoI, the antibody heavy and light chain genes were each inserted into MCS 1 using the Gibson Assembly® Master Mix (New England Biolabs) according to the manufacturer's instructions. Ligated DNA was transformed into EB5alpha (25 µL) competent cells (EdgeBio) and spread onto agar plates containing 100 m/mL ampicillin. Positive clones were identified with Sanger sequencing (Eton Bioscience). Amino Acid Sequence of Proteins. The amino acid sequences of the proteins used in this study are reported below. N-terminal methionine is shown in italics and is removed co-translationally by methionine aminopeptidase in *E. coli* cells.

(SEQ ID NO: 38)
*M*SKGPG(VGVPGLGVPGVGVPGLGVPGVGVPGVGVPGLGVPGVGVPGLGVP

GVGVP)₈GVDNKFNKEQQNAFYEILHLPNLNEEQRNAFIQSLKDDPSQSAN

LLAEAKKLNDAQAPK (SEQ ID NO: 39)
*M*VDNKFNKEQQNAFYEILHLPNLNEEQRNAFIQSLKDDPSQSANLLAEAKK

LNDAQAPKG(VGVPGLGVPGVGVPGLGVPGVGVPGVGVPGLGVPGVGVPGL

GVPGVGVP)₈

"ELP₁,₈₀-Cap"

(SEQ ID NO: 40)
*M*(VGVPGLGVPGVGVPGLGVPGVGVPGVGVPGLGVPGVGVPGLGVPGVGV

P)₈GVDNKFNKEQQNAFYEILHLPNLNEEQRNAFIQSLKDDPSQSANLLAE

AKKLNDAQAPK (SEQ ID NO: 41)
*M*GVDNKFNKEQQNAFYEILHLPNLNEEQRNAFIQSLKDDPSQSANLLAEAK

KLNDAQAPKG(VGVPGLGVPGVGVPGLGVPGVGVPGVGVPGLGVPGVGVPG

LGVPGVGVP)₁₂

(SEQ ID NO: 42)
*M*(VGVPGLGVPGVGVPGLGVPGVGVPGVGVPGLGVPGVGVPGLGVPGVGV

P)₁₂GVDNKFNKEQQNAFYEILHLPNLNEEQRNAFIQSLKDDPSQSANLLAE

AKKLNDAQAPKGVDNKFNKEQQNAFYEILHLPNLNEEQRNAFIQSLKDDPS

QSANLLAEAKKLNDAQAPKG (SEQ ID NO: 43)
*M*GVDNKFNKEQQNAFYEILHLPNLNEEQRNAFIQSLKDDPSQSANLLAEAK

KLNDAQAPKG(VGVPGLGVPGVGVPGLGVPGVGVPGVGVPGLGVPGVGVPG

LGVPGVGVP)₁₂GVDNKFNKEQQNAFYEILHLPNLNEEQRNAFIQSLKDDPS

QSANLLAEAKKLNDAQAPKG

"ELP1-Cap":

(SEQ ID NO: 44)
*M*(VGVPGLGVPGVGVPGLGVPGVGVPGVGVPGLGVPGVGVPGLGVPGVGV

P)₁₂GVDNKFNKEQQNAFYEILHLPNLNEEQRNAFIQSLKDDPSQSANLLAE

AKKLNDAQAPKG

"ELP₂-Cap"

(SEQ ID NO: 45)
*M*(VGVPG)₁₂₀GVDNKFNKEQQNAFYEILHLPNLNEEQRNAFIQSLKDDPSQ

SANLLAEAKKLNDAQAPKG

"ELP₃-Cap"

(SEQ ID NO: 46)
*M*(VGVPGAGVPG)₄₀GVDNKFNKEQQNAFYEILHLPNLNEEQRNAFIQSLKD

DPSQSANLLAEAKKLNDAQAPKG (SEQ ID NO: 47)
*M*(VGVPGAGVPG)₄₀GVDNKFNKEQQNAFYEILHLPNLNEEQRNAFIQSLKD

DPSQSANLLAEAKKLNDAQAPKG

"ELP₁,₈₀-CapG"

(SEQ ID NO: 48)
*M*SKGPG(VGVPGLGVPGVGVPGLGVPGVGVPGVGVPGLGVPGVGVPGLGVP

GVGVP)₈GTYKLILNGKTLKGETTTEAVDAATAEKVFKQYANDNGVDGEWT

YDDATKTFTVTEG

ELP-cap Expression Protocol

A single bacterial colony harboring the ELP-Cap gene was selected to inoculate 50 mL of autoclaved TB medium containing 45 µg/mL kanamycin at 37° C. on an orbital shaker at 200 rpm. After 12 h, the seed culture was centrifuged at 3500 rpm and 4° C. for 15 min to harvest the cells. The *E. coli* pellet was re-suspended in 6 mL of phosphate buffer saline (PBS) solution. 1 mL of this suspension was used to inoculate 1 L of autoclaved TB media containing 45 µg/mL kanamycin. The bacteria were cultivated in an orbital shaker incubator at 37° C. at 180 rpm. After 6 h, expression was induced by the addition of IPTG to a final concentration of 0.5 mM.

Purification Protocol

After 18 h post-induction, the cells were harvested by centrifugation at 3500 rpm and 4° C. for 15 min. The bacterial pellet was re-suspended in PBS (5 mL PBS for each 1 L of expression culture). The cells were then lysed by two cycles of sonication at 4° C. using sequential pulses of 10 s at 85 W followed by 40 s resting-time for a total sonication period of 90 s. The lysed bacterial solution was transferred to polycarbonate centrifuge tubes and 20% w/v polyethylenimine (1 mL per every 1 L of expression culture) was added to remove the nucleic acid fragments. Each tube was vortexed several times to ensure complete mixing until a white homogenous precipitate appeared in the entire volume of the solution, after which, the solution was centrifuged at 14 krpm and 4° C. for 15 min to separate the protein from insoluble cell debris and contaminants. The clear supernatant layer was transferred to clear polycarbonate tubes and was then subjected to one to three rounds of inverse transition cycling (ITC) or one to two rounds of 'bakeout'.

For ITC, the phase transition of the ELP-Cap was triggered isothermally by the addition of solid NaCl. The phase separated coacervates were then collected by a centrifugation step at 14 krpm for 15 min, after which the supernatant was discarded. The pellet was then resuspended in 4 ml, of deionized H2O or PBS, and the tubes were placed on a tube rotisserie within a 4° C. refrigerator. Once fully resuspended, the mixture was centrifuged at 14 krpm and 4° C. for 15 min and the pellet was discarded. The supernatant was transferred to a clean tube and was subjected to another round of ITC. For the subsequent round(s) of ITC, a 5 M NaCl aqueous solution was used to trigger the phase separation instead of NaCl solids. After the final spin, the ELP-Cap was analyzed by SDS-PAGE to ensure purity (>95%).

Monoclonal Antibody Expression

A single bacterial colony for each antibody heavy and light chain gene were selected to inoculate 50 mL of autoclaved TB medium containing 100 µg/mL ampicillin at 37° C. on an orbital shaker at 200 rpm. After 12 h, the plasmid DNA was purified using a Qiagen Midiprep Kit, according to the manufacturer's instructions. ExpiHEK and ExpiCHO cells were cultured and transiently transfected with both heavy and light chain-containing plasmids for each antibody according to manufacture protocols. After the recommended culture times, the cell culture harvest was centrifuged to pellet the cells and the supernatant was clarified by filtration through a 0.45 μm PES filter.

Monoclonal Antibody Purification

Antibody from the clarified cell culture harvest was purified by either a 1 mL Pierce Protein A column or a GE Predictor Plate containing 50 μL of mAb Select SuRe resin, according the manufacture protocols. Alternatively, an equivalent volume of clarified cell culture harvest was purified using the new affinity/liquid-liquid phase separation method with the purified ELP-Cap reagent. Product purity was compared qualitatively using SDS-PAGE and quantitatively using size exclusion chromatography (SEC) with a Shodex OHpak KB-804 column and PBS mobile phase. Contaminant removal was assessed using a HEK host cell protein ELISA (Cygnus), a CHO host cell protein ELISA (Canopy), dsDNA kits (Quant¬iT PicoGreen Assay by Thermo Fisher or AccuClear Assay by Biotium), and an endotoxin assay (Endosafe, Charles River). Yield was determined using UV-Vis spectrophotometry by measuring absorbance at 280 nm, normalized to 340 nm absorbance (NanoDrop OneC, Thermo Fisher or BioTek Synergy HT plate reader).

The conditions for purification with ELP-Cap by affinity/phase separation were fully optimized. The conditions optimized include: (1) the fusion protein's transition temperature, (2) the amount of salt added to trigger phase separation, (3) the centrifugation speed needed to optimally pellet the complexed antibody, (4) the elution pH, (5) the ELP-Cap to antibody molar ratio, and (6) the affinity (using isothermal titration calorimetry and surface plasmon resonance). The method was validated using centrifugation in both a spin tube and 96-well plate format as well as with filtration.

EXAMPLE 2

Optimization of Capture Fusion Proteins

Cap-ELP fusion proteins were expressed in *E. coli* and purified as detailed above. Mammalian cells (ExpiCHO and ExpiHEK) were cultured and transiently transfected for antibody expression as per manufacturer protocols (ThermoFisher).

Figure 2:
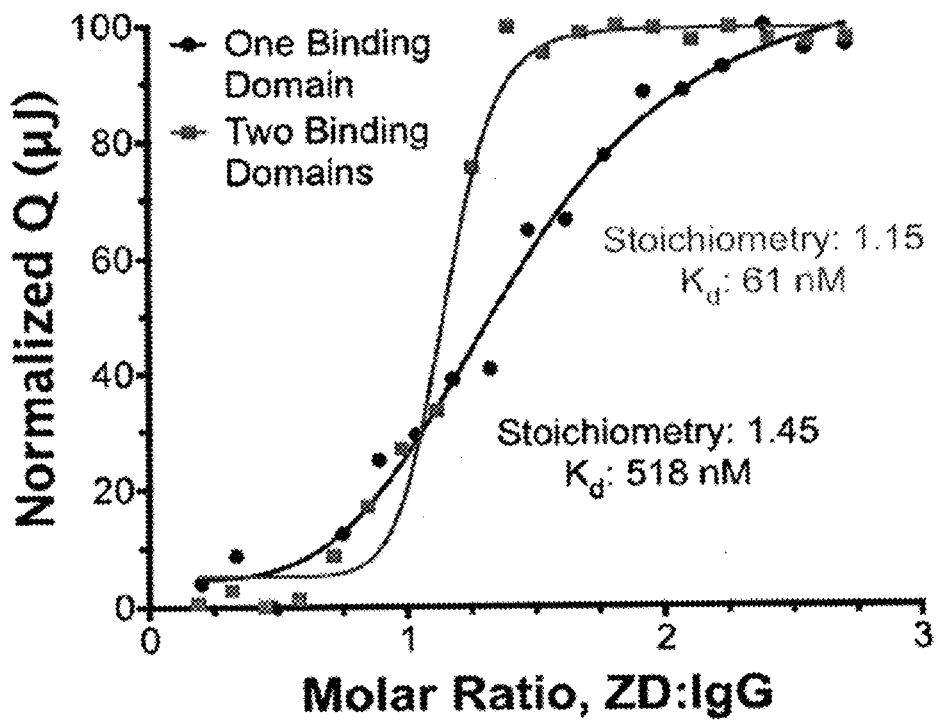
FIG. 2 shows the affinity of the ELP-Cap for its target can be tuned by adjusting the number of capture domain fusions at the genetic level. For example, a fusion containing two capture domains has a 10-fold higher affinity than a fusion with just a single capture domain.

For the Isothermal Titration calorimetry experiment (FIG. 2), pure human IgG (hIgG) was purchased from Sigma. The hIgG was made to 10 μM in PBS and added to the cell of a NanoITC microcalorimeter (TA Instruments). Cap-ELP fusion with either one or two Cap binding domains was made to 125 μM in PBS. The machine was set to 10° C. with 350 rpm stir speed, 25×10 μinjections, 300 s equilibration time. The heat of dilution was subtracted and the data was fit using built-in models. This demonstrates the control and tunability over the capture fusion's affinity for the target biologic.

Figure 3:
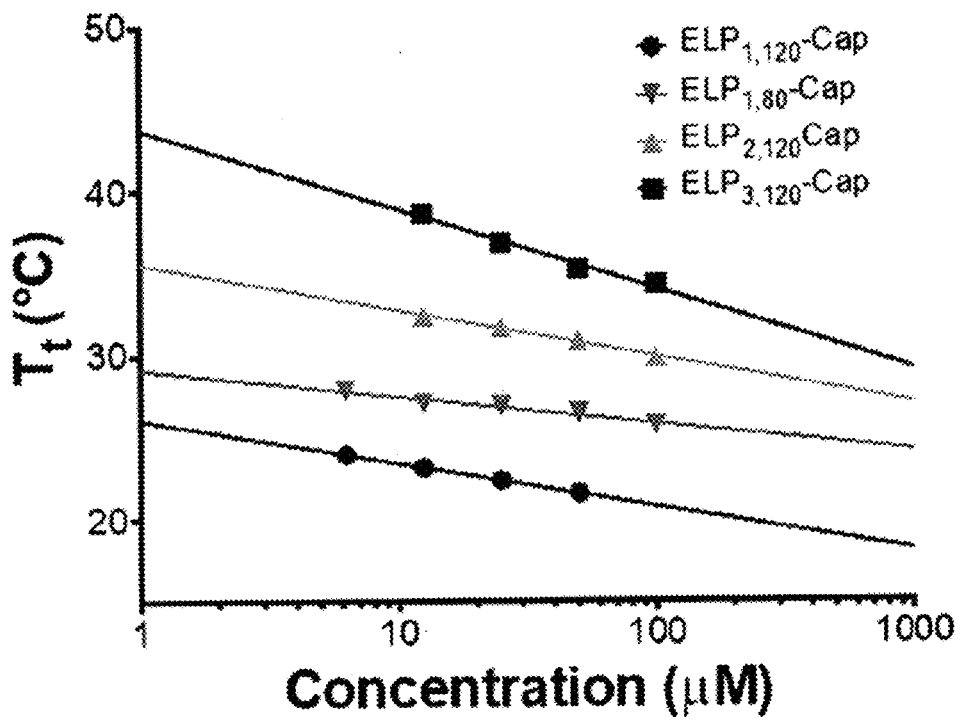
FIG. 3 shows the highly tunable phase transition of an ELP-Cap fusion protein can be easily manipulated by changing the molecular composition of the guest residue, 'Xaa', or the molecular weight (number of pentapeptide repeats). Here, $ELP_1$ is comprised of 40% Leu/60% Val, $ELP_2$ of 100% Val, and $ELP_3$ of 20% Ala/80% Val.
Figure 4:
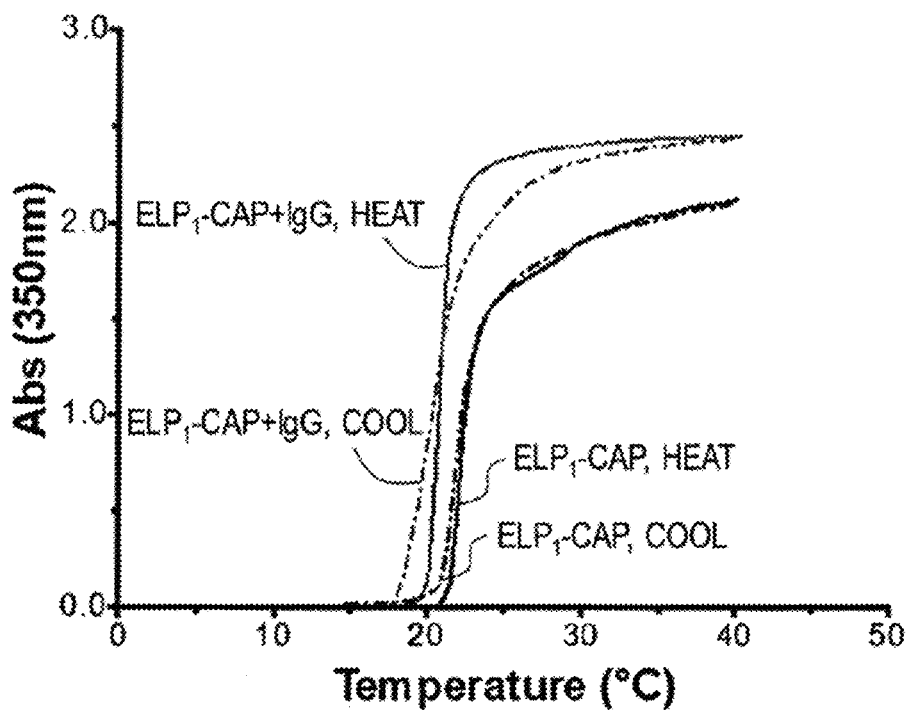
FIG. 4 shows the phase behavior of the ELP-Cap fusion protein is fully reversible on its own and with antibody bound to it.
Figure 5:
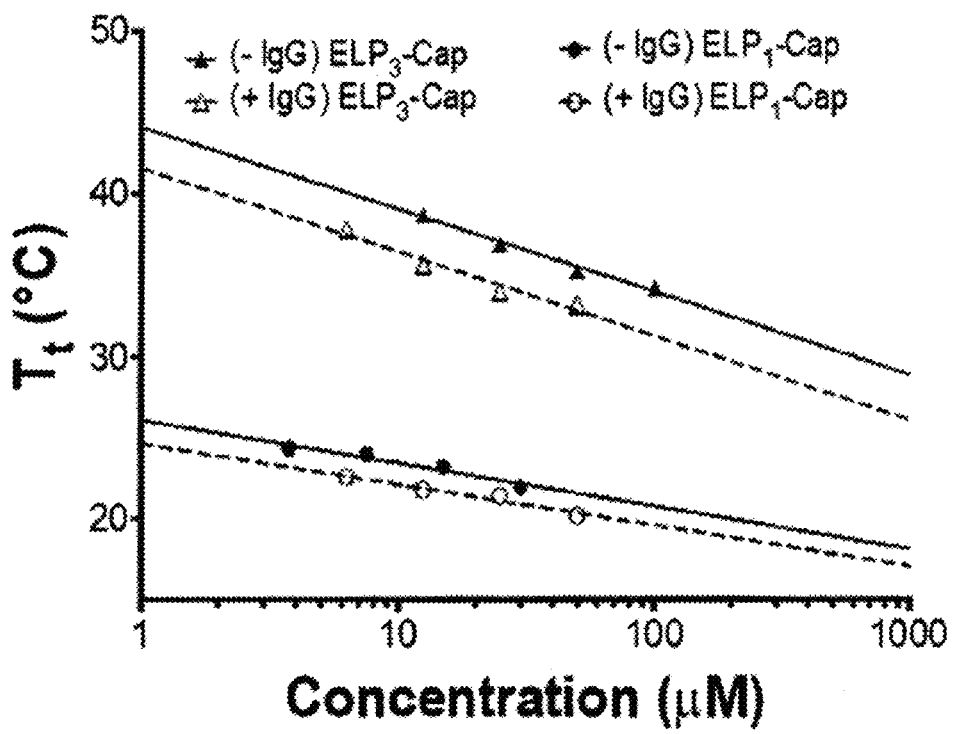
FIG. 5 shows that regardless of the composition of the ELP, its transition temperature is slightly suppressed in the presence of antibody.
Figure 6A:
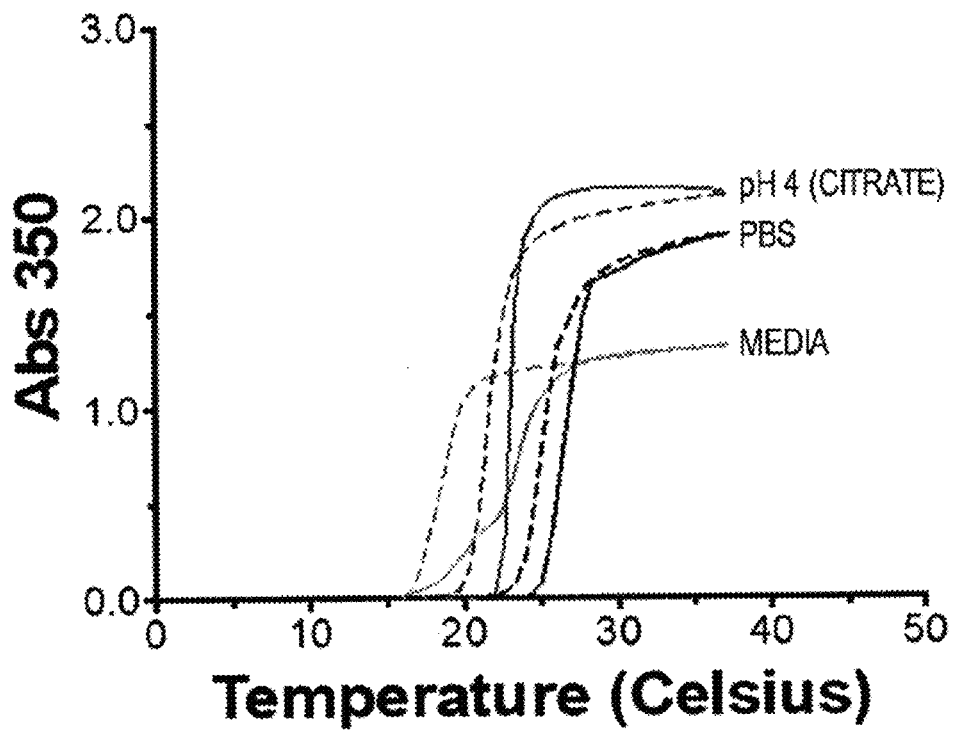
FIGS. 6A-6B show the phase behavior of the ELP-Cap fusion with optimal phase behavior tested in various conditions that will be encountered during the affinity/phase separation process: media during antibody capture, phosphate buffer during resuspension, and low pH buffer during elution. The phase behavior of the fusion was reversible (FIG. 6A) and occurred near room temperature (FIG. 6B) in all conditions.
Figure 6B:
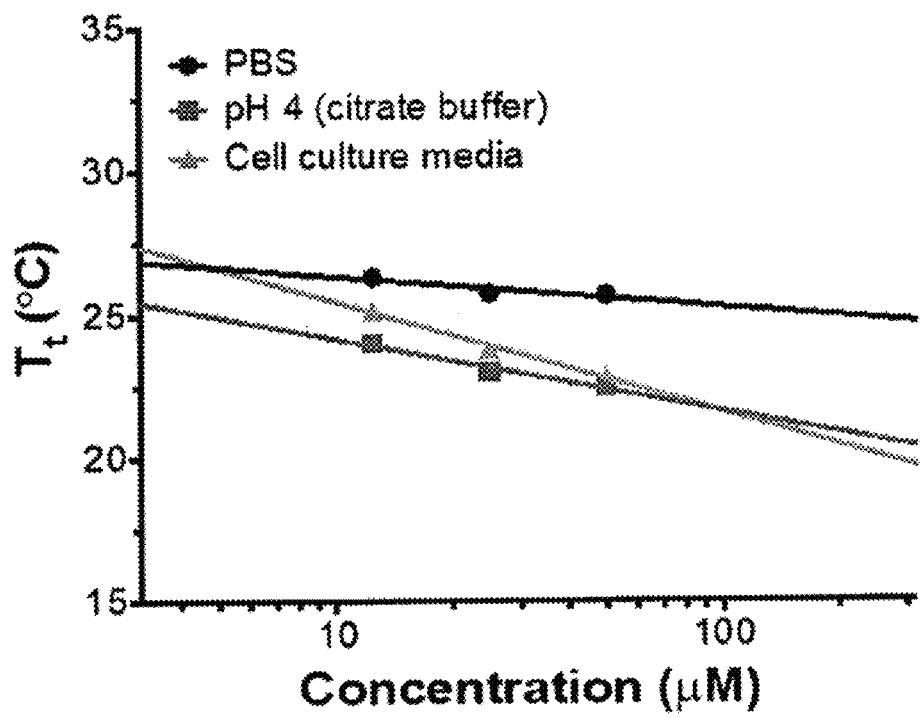

To determine the fusions' transition temperature (Tt) as a function of concentration, the purified fusions were made to concentrations ranging from 5 to 100 M in PBS or other relevant buffers (sodium citrate pH 4 and cell culture media). 800 μL of each sample was pipetted into a quartz cuvette and the absorbance at 350 nm was monitored as the temperature was ramped from 10 to 45° C., and then cooled back down to 10° C. (1° C./min ramp rate, data collection interval of 3/min) This data was collected on an Agilent Cary UV-Vis spectrophotometer. The derivative of this data was calculated and the temperature corresponding to the maximum of this first derivative was defined as the $T_t$. These $T_t$ values were then plotted as a function of log(concentration) as shown in FIG. 3. This demonstrates the high degree of control and tunability over the capture fusion's phase separation behavior (its $T_t$. Raw absorbance values as a function of temperature heating and cooling are shown (FIG. 4) for ELPI-Cap in PBS either with or without hIgG at a 1:4 molar ratio of antibody to fusion protein. This study proves that the capture fusion protein has reversible phase behavior, which is critical to the purification protocol so that the biologic can be resolubilized after capture and separation from contaminants. This study was performed at various concentrations while maintaining the 1:4 molar ratio to generate the Tt versus log(concentration) plots shown in FIG. 5. This demonstrates that the target biologic can impact the fusion protein's phase behavior. An understanding of how the biologic impacts the $T_t$ is important to optimizing the capture fusion protein selected for a given purification application. This procedure was repeated without antibody, but with ELP1-Cap in various buffers relevant to the antibody purification protocol FIGS. 6A-6B to ensure that the fusion protein maintains an optimal $T_t$ (around room temperature) throughout the different steps in the purification procedure.

Figure 7:
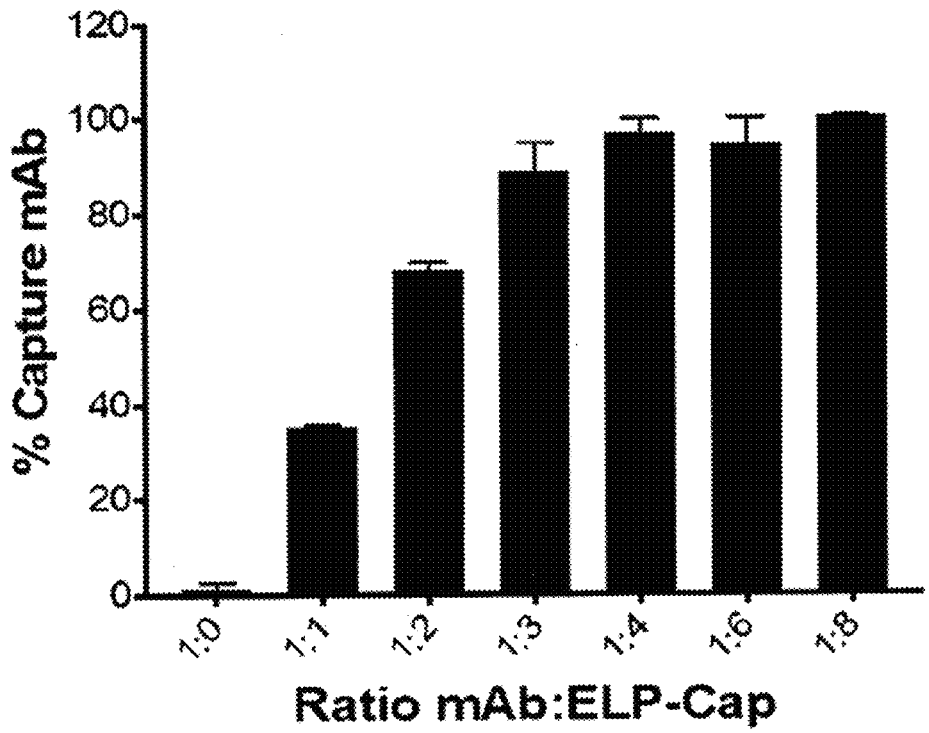
FIG. 7 shows the optimization of the molar ratio of mAb to ELP-Cap. The optimal ratio is between 3 and 4 ELP-Cap fusions per mAb. This is slightly higher than the expected 1:2 ratio, likely because of steric hindrance of the ELP.

To determine an optimal molar ratio, purified Herceptin (trastuzumab, IgG1) was made to a fixed concentration in PBS. ELP1,80-Cap was added to varying ratios spanning 1 to 8-fold molar excess, while keeping the total antibody concentration constant. NaCl was added to 0.6 M and the transitioned solution was centrifuged at 12,000 ref for 5 minutes. The absorbance at 280 nm in the supernatant was then measured to determine the amount of antibody pulled down. Two controls were also centrifuged that contained only $ELP_{1,80}$-Cap or only Herceptin. The data was normalized to the Herceptin only control to calculate a percentage captured for each condition (FIG. 7). This study shows that, for antibody purification, a 4:1 molar ratio of antibody to ELP-cap was optimal for complete capture. This ratio may vary depending on the binding kinetics, number of binding sites, and steric hindrance for any given application.

Figure 8:
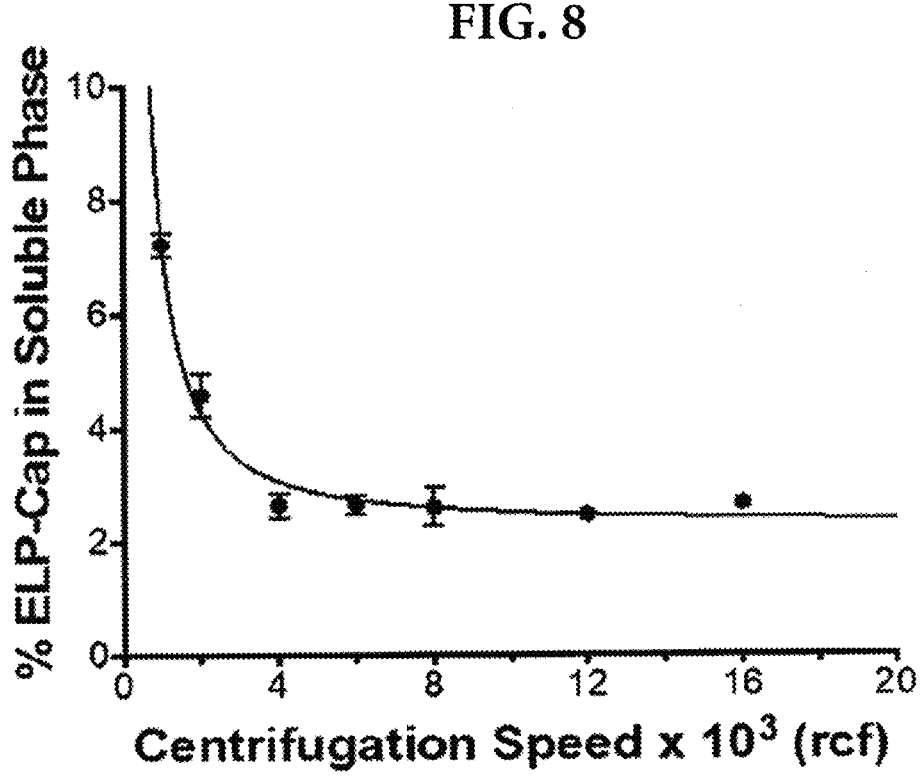
FIG. 8 shows the centrifugal force needed to separate the ELP-Cap from the soluble phase once transition was optimized. The minimum speed that should be used for purification is 4,000 rcf.
Figure 9:
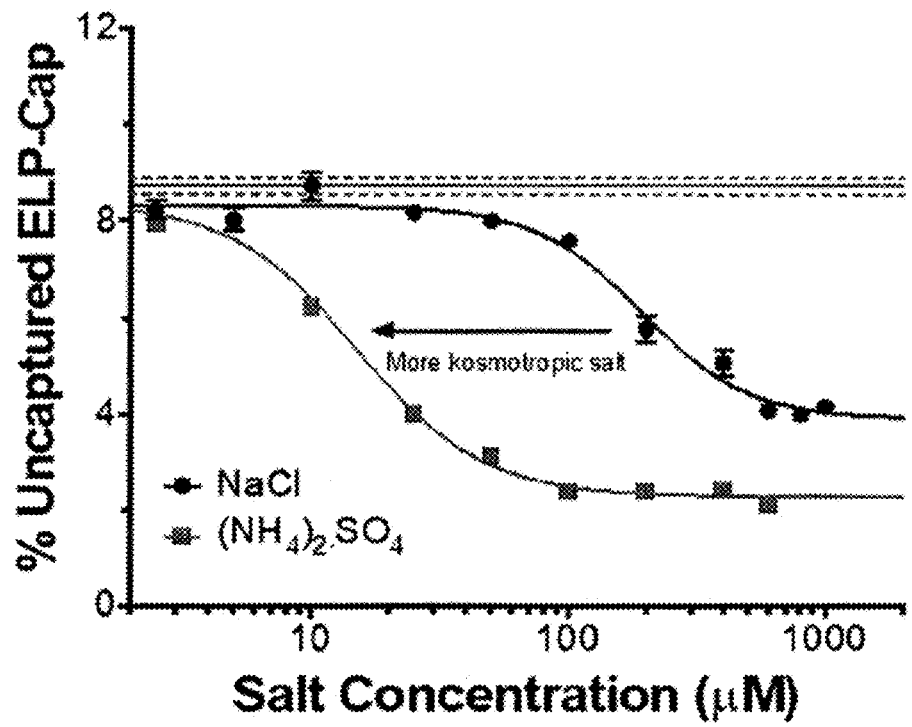
FIG. 9 shows different kosmotropic salts can be used to trigger phase separation of the optimal ELP-Cap fusion at ambient temperature. The optimal concentration for two common salts was determined.

Centrifugation speed and salt concentration were optimized by centrifuging a known concentration of $ELP_{1,80}$-Cap and quantifying the absorbance at 280 nm of the supernatant and pellet (FIG. 8). Total protein remaining in the supernatant was also quantified using a BCA protein assay and a Protein A ELISA (Enzo Life Sciences) with a custom $ELP_{1,80}$-Cap standard curve (FIG. 9). These studies demonstrate that a minimum centrifugal force of 4,000 ref and a minimum salt concentration of 0.1M ammonium sulfate or 0.6M NaCl are needed to optimally separate the ELP-Cap fusion protein once the phase separation was triggered and micron-sized coacervates were formed.

Figure 10:
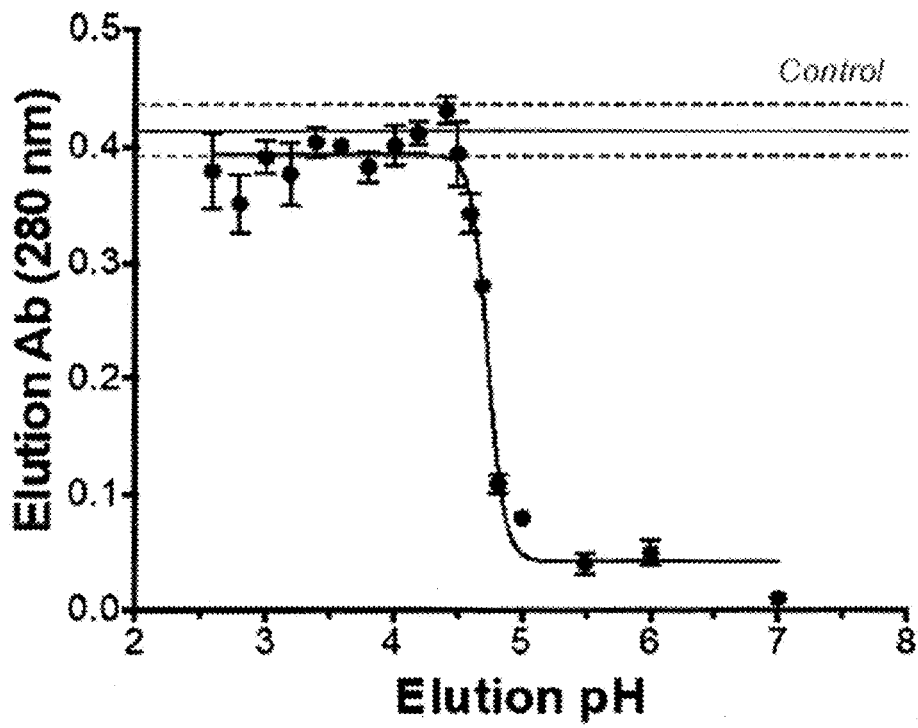
FIG. 10 shows the optimal elution pH as determined by measuring final monoclonal antibody product after performing the low pH phase separation step at variable pH. A pH of ~4 is optimal with HERCEPTIN®.

To optimize the pH required for full antibody elution, purified Herceptin was added to a known concentration (5 μM) and ELP1,80-Cap was added in 4-fold molar excess in 50 μL total volume. 50 μL of elution buffer (100 mM sodium citrate) titrated to pH ranging from 2.4 to 4.8 or 100 mM sodium acetate at pH ranging from 5 to 6 were added to the Herceptin—$ELP_{1,80}$-Cap complex. A control in PBS was performed as a control, where no elution would be expected and all of the Herceptin would be pulled into the pellet. 0.6 M NaCl was added and the solutions were centrifuged at 12,000 rcf for 5 min. The absorbance 280 nm of the supernatants was measured to quantify the amount of Herceptin eluted and remaining in the supernatant (FIG. 10). This study showed that Herceptin is maximally eluted at a pH between 4.0 and 4.5, which is higher (and thus more gentle) than standard Protein A chromatography purification, which often uses elution conditions of pH 3.5 or lower.

Figure 11:
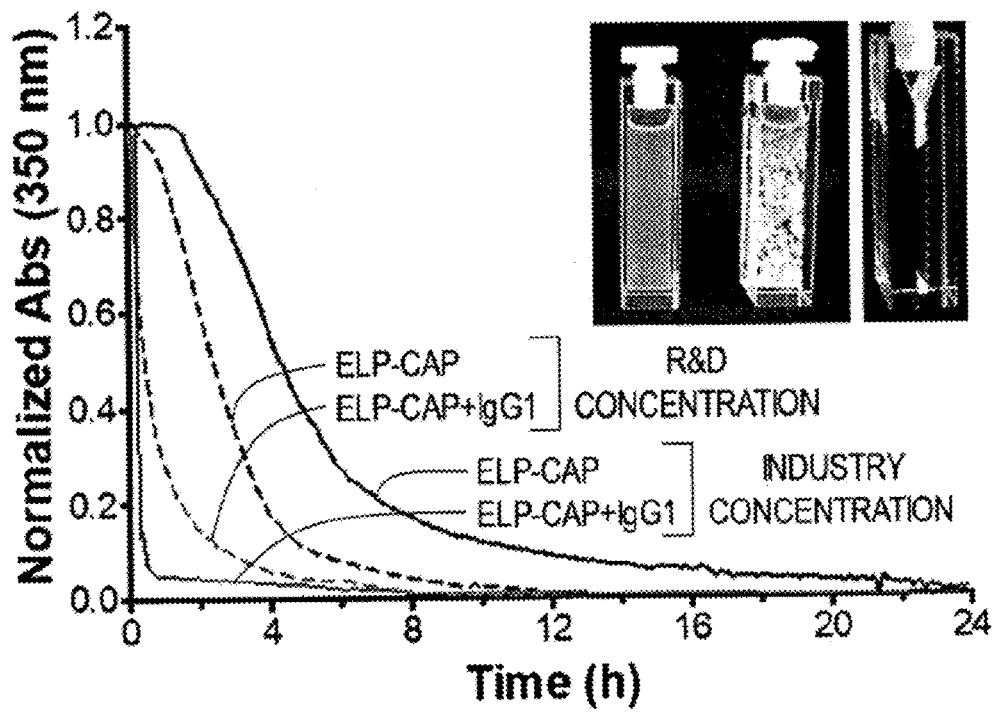
FIG. 11 shows that at industry titers of antibody (2-5 g/L), the capture step can be performed by simply waiting and letting the coacervates reach their settled, phase separated equilibrium state. The flocculation was monitored by measuring the absorbance with time. Images also show the difference between control ELP (left) compared to ELP-Cap+antibody (middle) and settled (right).

To determine the feasibility of passive settling, or flocculation, as an alternative to centrifugation, purified Herceptin was made to either 0.3 or 3 g/L in PBS. ELP1,80-Cap was added at a 4-fold molar excess. The samples were pipetted into quartz cuvettes and the absorbance at 350 nm was monitored at room temperature for 24 hours (FIG. 11) using the kinetics mode on an Agilent Cary UV-Vis spectrophotometer maintained at 25° C. This study demonstrates that passive settling, or flocculation, can be used in place of centrifugation to separate the captured biologic once bound and phase separated with the ELP-Cap protein, particularly at the higher concentrations found in an industry setting.

Figure 12:
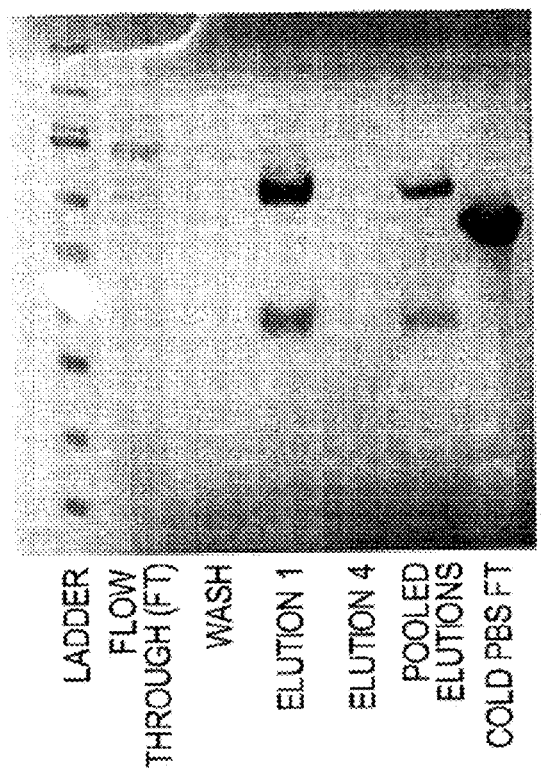
FIG. 12 shows that microfiltration can be used to separate antibody from cell culture contaminants.

To determine the feasibility of filtration as an alternative to centrifugation, Herceptin was cultured, harvested, and clarified. ELP1,80-Cap was added on ice at 10 μM to the clarified harvest. Once the sample had warmed to room temperature, 0.6M NaCl was added and the sample was left for 10-30 minutes. The sample (1 mL) was then applied to a 0.2 or 0.45 μm syringe filter. The flow through was collected and the filter was washed with 250 μL of 0.6 M NaCl in PBS. The flow through was collected and the wash was repeated two additional times. The sample was then eluted using 100 mM sodium citrate, pH 4 with 0.6 M NaCl (100 μL) three times. The flow through from each step was run on an SDS-PAGE gel and stained with SimplyBlue (FIG. 12). This gel shows that filtration can be used to successfully purify Herceptin from cell culture harvest and recover the ELP-cap fusion.

Figure 13:
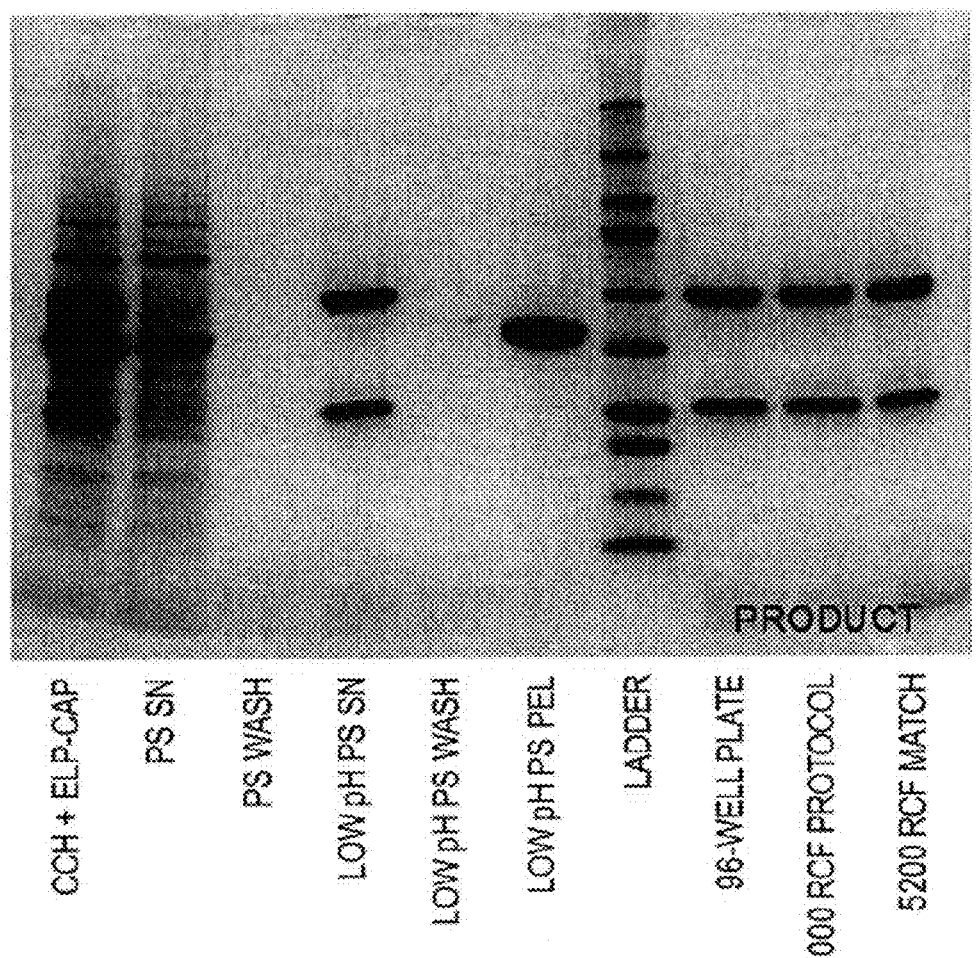
FIG. 13 shows that affinity-based liquid-liquid phase separation with ELP-Cap worked in a high-throughput 96-well plate format, purifying small volumes of antibody to high purity from cell culture harvest.

The standard spin tube purification procedure was repeated in a standard 96-well plate in triplicate. Briefly, 250 μL, of clarified Herceptin culture with 4-fold molar excess $ELP_{1,80}$-Cap was added to either a plate (x3) or spin tubes (x6). NaCl was added to a final concentration of 0.6 M. The plate was spun at 5,200 ref. Three of the six eppendorf tubes were spun at a matched speed (5,200 rcf) and the remaining three were centrifuged at 14,000 rcf. The supernatant was removed. The pellets in the plate and tubes were washed with 0.6 M NaCl. The pellets were resuspended in 50 μL cold PBS and incubated in a 4° C. deli fridge for 15-30 minutes. An equal volume of elution buffer was added and 0.6 M NaCl was added once the samples had warmed to room temperature. The plate and tubes were centrifuged again at speeds equal to their capture step. The final supernatant was removed and neutralized with one-tenth the volume of 1 M Tris-HCl pH 8.5. The pellets were resuspended in 50 μL cold PBS. Each fraction was run on an SDS-PAGE gel and stained with SimplyBlue to assess purity (FIG. 13). This gel demonstrates the centrifugation procedure can be conducted in a high-throughput manner in a 96-well plate format to provide similar purity and yield to the standard spin tube format that is used for larger volumes.

Figure 14C:
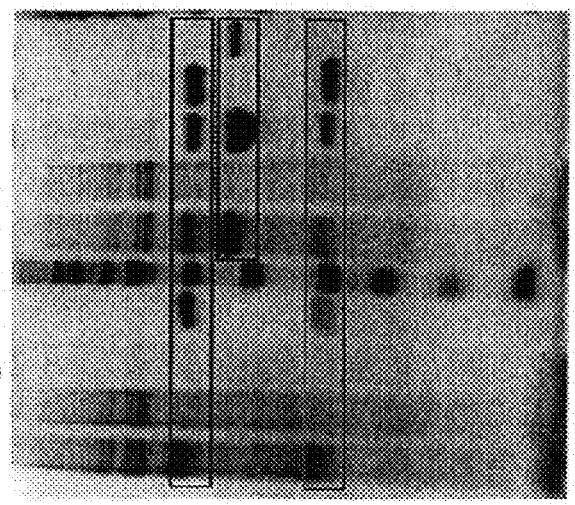
FIGS. 14A-14C show SDS-PAGE gels (stained with SimplyBlue™) demonstrating the purification of mAbs by either PrA affinity chromatography (Pierce) or ELP-Cap affinity/phase transition. Purification was conducted on FDA approved human or humanized IgG therapeutics of varied isotype.
Figure 14B:
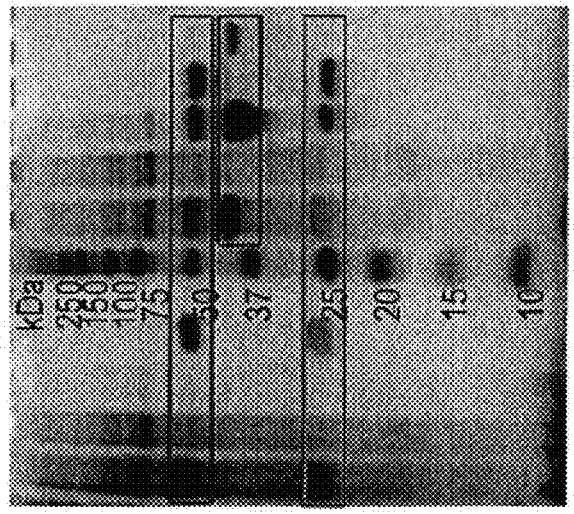
Figure 14A:
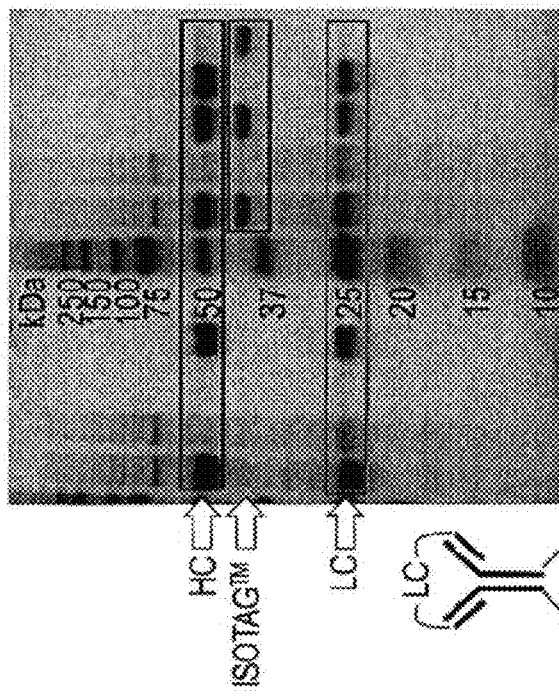
Figures 15A, 15B, 15C:
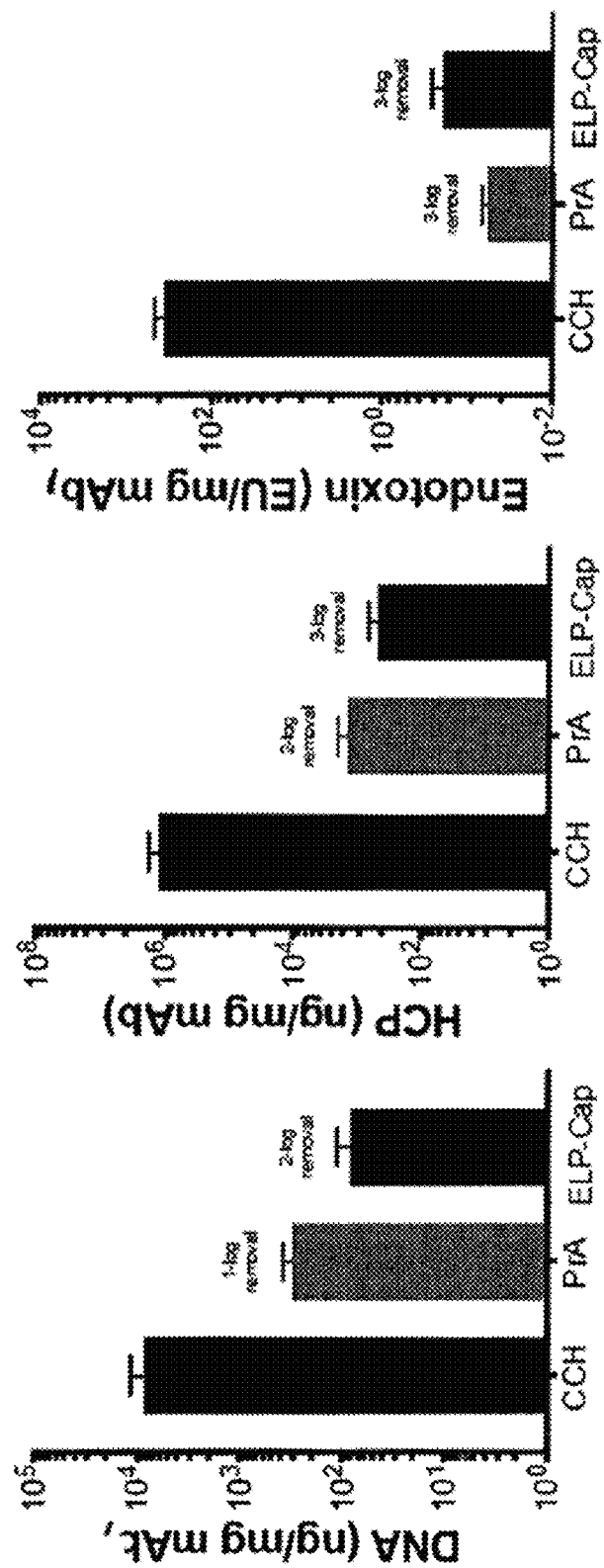
FIGS. 15A-15C show a comparison of major contaminant removal from CCH by PrA column (Pierce) versus ELP-Cap.
Figure 16:
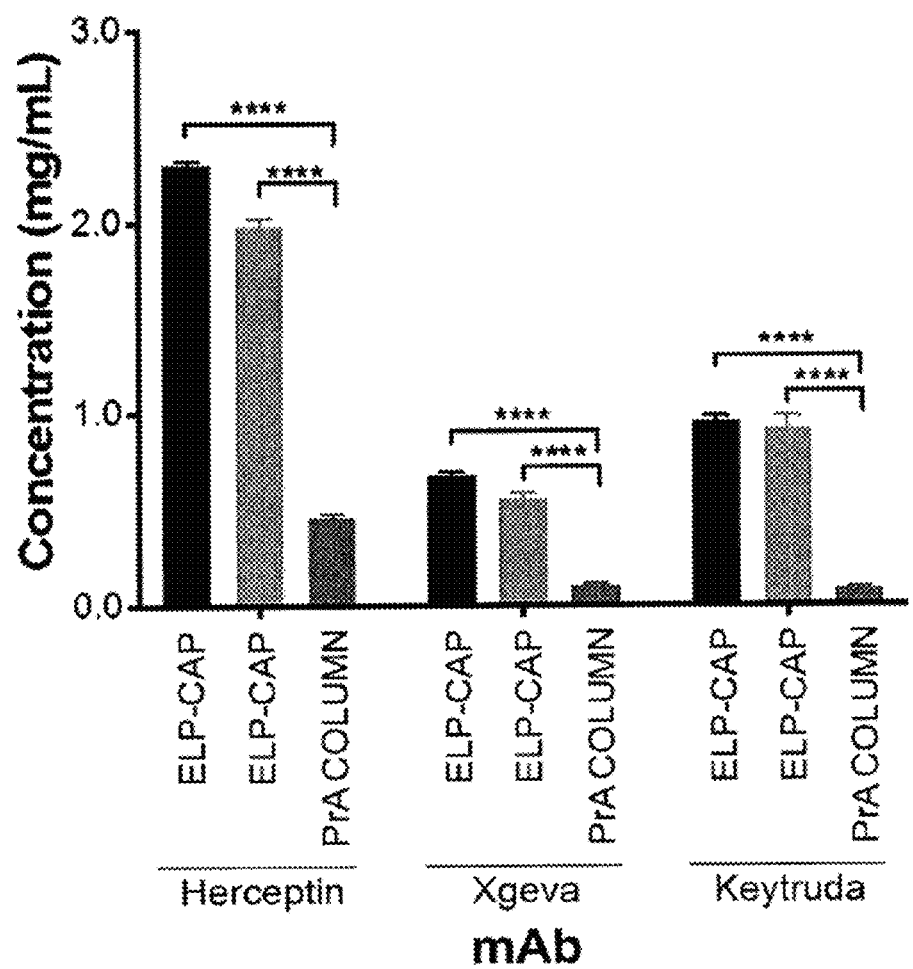
FIG. 16 shows overall antibody yield is statistically significantly greater with ELP-Cap affinity/phase separation purification than with traditional Protein A chromatography for all three IgG isotypes tested.

This same procedure in the spin tube format was performed on cell culture harvests from Expi293 cells transiently transfected with the light and heavy chains for three different FDA-approved therapeutic antibodies (Herceptin, Xgeva, and Keytruda), which represent the three main IgG isotypes used as therapeutics in the clinic (IgG1, IgG2, and IgG4). Equal volumes of the same clarified harvests were also purified using a 1 mL Protein A resin (Pierce). Different fractions from each purification method (Protein A column and ELP-cap affinity/phase separation) and for each antibody (Herceptin, Xgeva, and Keytruda) were collected and run on an SDS-PAGE gel to assess purity (FIGS. 14A-14C). Both methods provided similar levels of purity. The final eluted products were analyzed for contaminant removal (FIGS. 15A-15C) using a host cell protein ELISA (Cygnus), a dsDNA assay (Biotium AccuClear), and an endotoxin assay (Charles River Endosafe). The total concentration (FIG. 16) and yield of the two purification methods was quantified by dividing the 280 nm absorbance values by the antibody's specific extinction coefficient. Together, these results demonstrate that contaminant removal, yield, and concentration are equivalent or superior for the ELP-cap affinity/phase separation method compared to the standard Protein A column method.

Figures 17A, 17B, 17C:
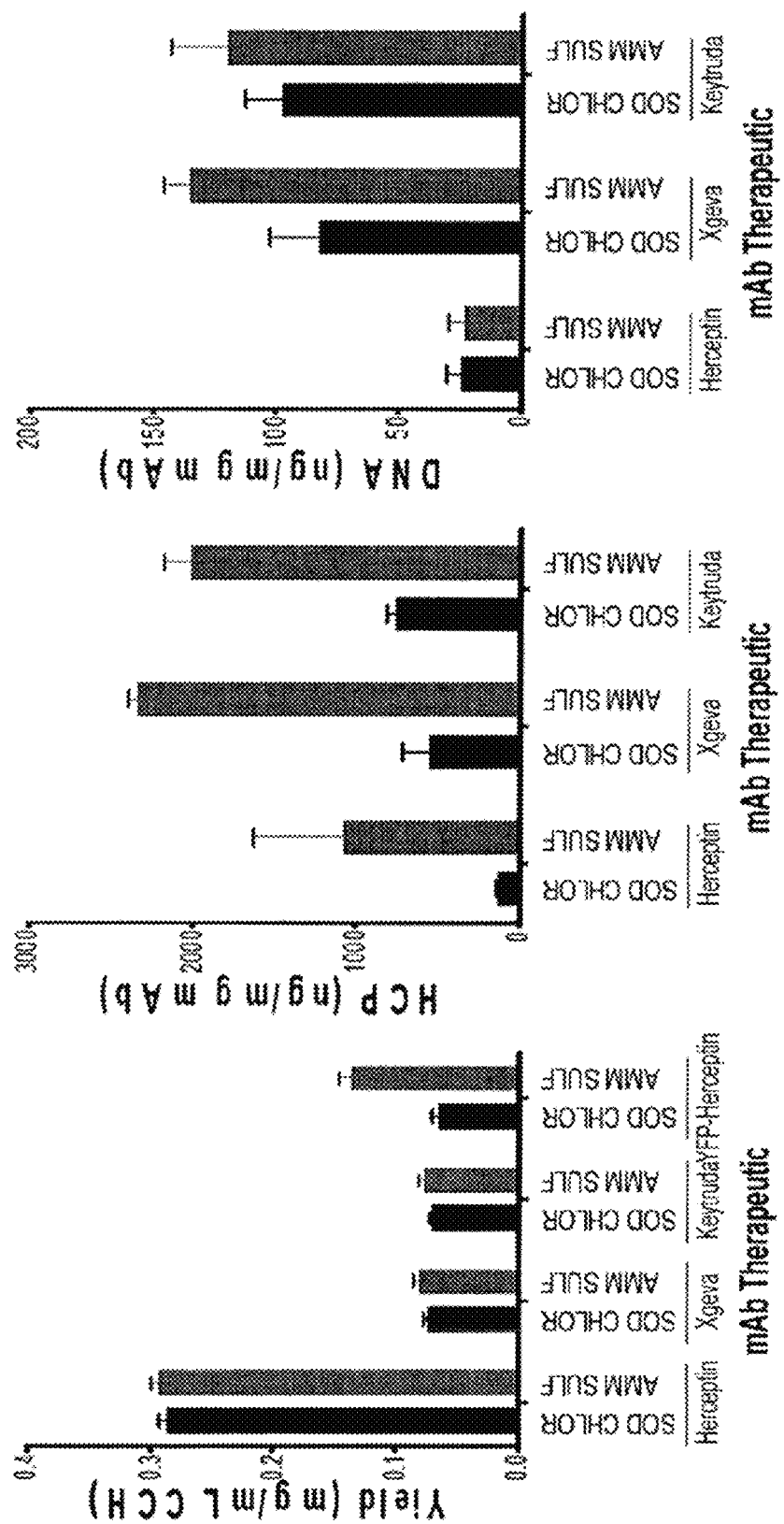
FIGS. 17A-17C show that although yield (FIG. 17A) is slightly higher when the affinity/phase separation is triggered with ammonium sulfate rather than sodium chloride, the more kosmotropic salt yields products with greater amounts of impurities, likely due to the salting out effect on other host cell proteins (FIG. 17B) and DNA (FIG. 17C). This is why it is critical that the ELP-Cap fusion be optimized to undergo phase separation at ambient conditions with a minimal amount of salt. Doing so leads to an antibody with greater purity and less aggregation.

The purification and analysis with $ELP_{1,80}$-Cap was repeated as described above using two different salts, NaCl and ammonium sulfate, to determine the impact of salt on yield and contaminant removal (FIGS. 17A-17C). Ammonium sulfate is a stronger kosomotrope and, thus, can be used at a lower concentration than NaCl to trigger phase separation. This study shows that ammonium sulfate provided slightly higher yields than NaCl, but worse contaminant removal, likely because it was salting out contaminant proteins.

Figure 18:
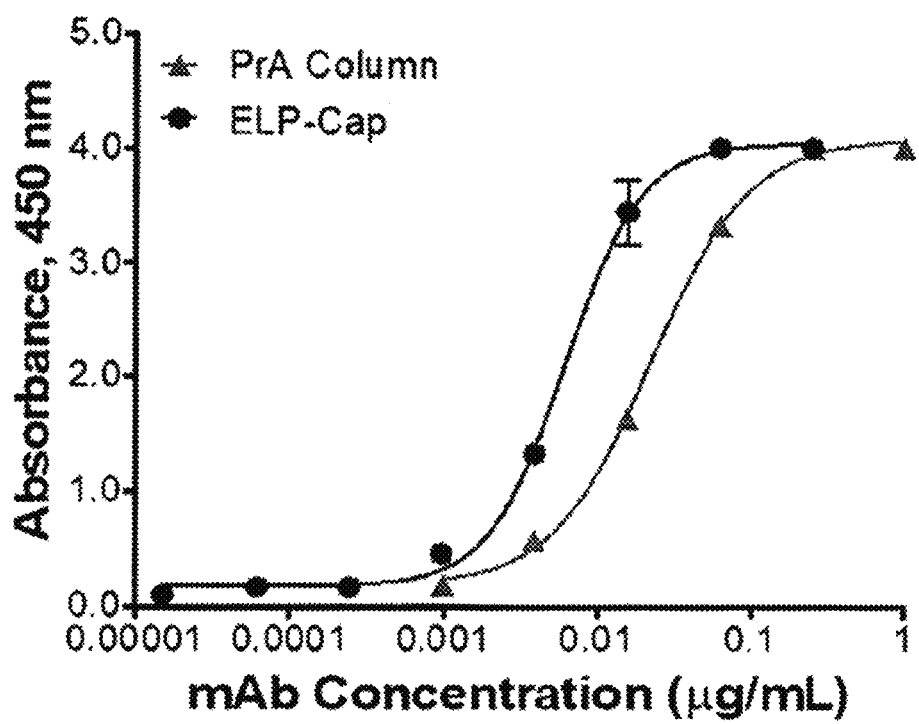
FIG. 18 shows an antigen-down ELISA using fluorescently labeled antibodies purified by either Protein A or ELP-Cap, demonstrating that the affinity/phase separation product is more active, as evidenced by a left shift in this activity assay. One explanation for this is the gentler conditions that are required for elution due to only a single binding domain.

An antigen-down ELISA was performed on samples purified with either ELP-Cap affinity/phase separation or standard Protein A chromatography. The antibody was labeled with a fluorophore using NHS-ester chemistry and each batch was adjusted with unlabeled antibody to the same concentration and degree of labeling. Antigen was printed at varying concentrations and the surface was blocked. Next, known concentrations of labeled antibody were applied and then washed. The final absorbance values were quantified to determine the activity of the detection antibody purified with the two different methods. The antibody purified by ELP-Cap appeared to be left-shifted; this indicates that the ELP-Cap purification method provided a pure product with higher activity at equivalent concentration compared to that purified by Protein A chromatography (FIG. 18).

Herceptin, purified as described above by either ELP-Cap or conventional Protein A chromatography, was analyzed using analytical size exclusion chromatography (SEC) with a Shodex OHPak KB-804 column and PBS as the mobile phase. This study was conducted to compare yield and purity and it showed similar outcomes for ELP-Cap purification versus conventional Protein A (FIG. 19).

Figures 19A, 19B, 20:
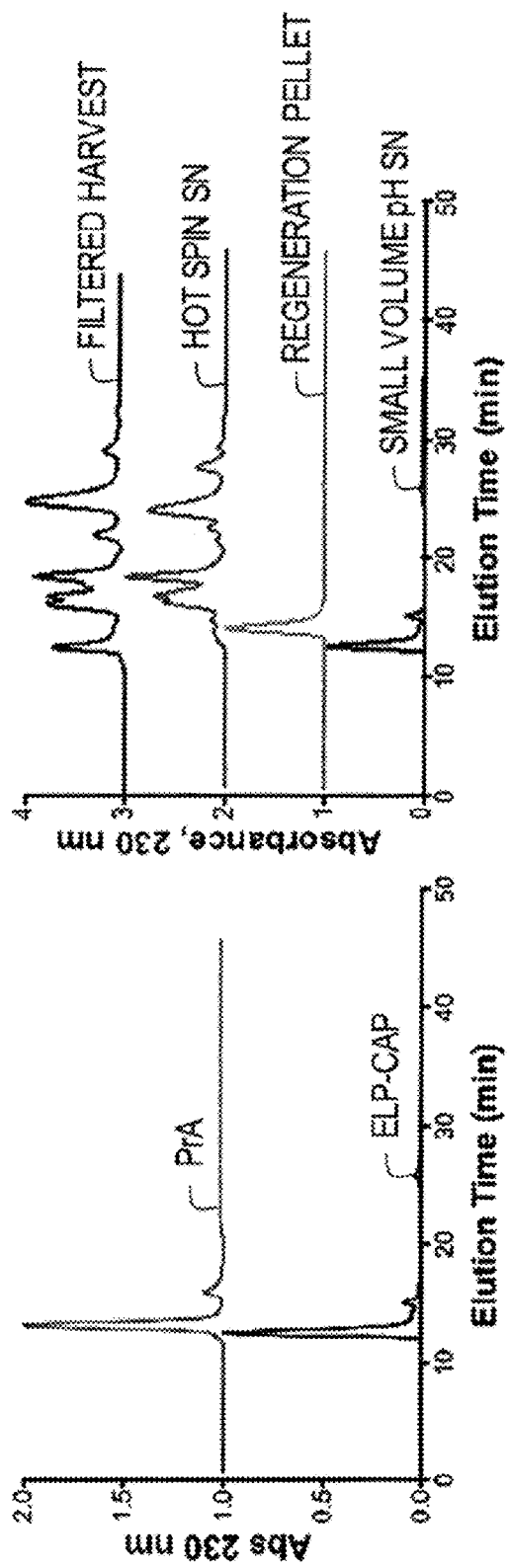
FIGS. 19A-19B show SEC HPLC traces demonstrating similar levels of purity for ELP-Cap versus Protein A purified HERCEPTIN® (A) as well as contaminant removal throughout the various stages of ELP-Cap purification (B). It is worth noting that there is less of a left-hand shoulder in the ELP-Cap product compare to the Protein A product. This is further evidence of reduced aggregation due to the gentle and optimized purification conditions for affinity/phase separation.
FIG. 20 shows affinity/phase separation with the optimized ELP-Cap fusion compared to an industry standard R&D product, the GE Predictor Plate filled with 50 µL Mab Select SuRe resin. For all IgG isotypes tested, the ELP-Cap provided significantly higher levels of purity.

ELP-Cap affinity/phase separation was performed on industry samples with titers ranging from 0.7-3.2 g/L and varied isotype (IgG1, IgG2, or IgG4). Identical volumes of these clarified harvests (1 mL) were purified using an industry standard method—the GE Predictor Plate (deep 96-well containing 50 μL of MabSelectSuRe resin). The yield and concentration of the final, purified products were determined using absorbance 280 nm measurements. Purification with affinity/phase separation showed superior yield and concentration across all samples (FIG. 20).

Figures 21A, 21B:
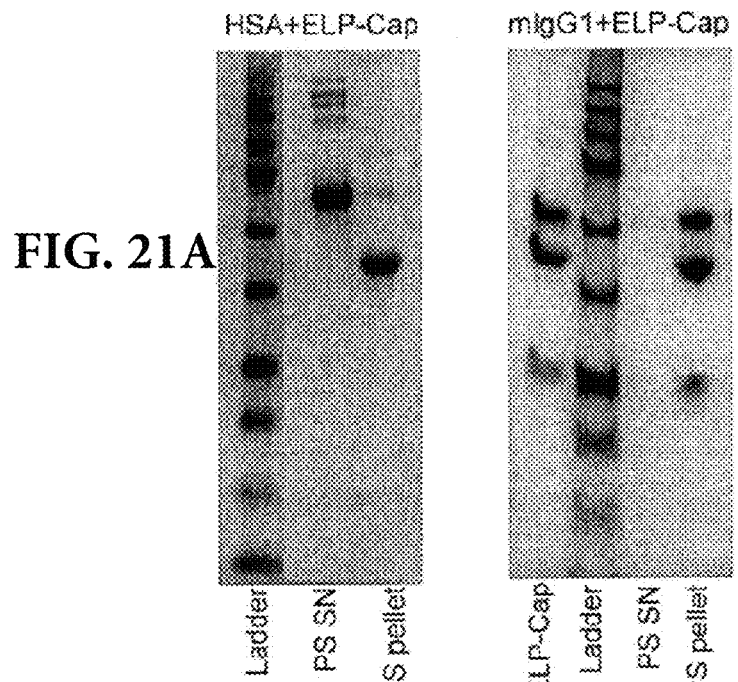
FIGS. 21A-21B show a fusion comprised of an optimal ELP and a Protein G domain can also be used to purify antibodies that do not bind well to Protein A, such as murine IgG1. Unlike full-length Protein G, this ELP-Cap fusion does not pull down albumin, which remains in the phase separation supernatant (SN), rather than the pellet (FIG. 21A), but murine IgG1 is captured into the pellet (FIG. 21B).

$ELP_{1,80}$-CapG was added to a solution of either human serum albumin or pure murine IgG1 (mIgG1), which binds poorly to Protein A (and ELP-Cap). The solution's phase transition was triggered with 0.6 M NaCl and centrifuged. The supernatant and pellet were analyzed by SDS-PAGE to demonstrate the ability of this construct to specifically capture mIgG1, but not albumin (FIGS. 21A-21B).

Figure 22:
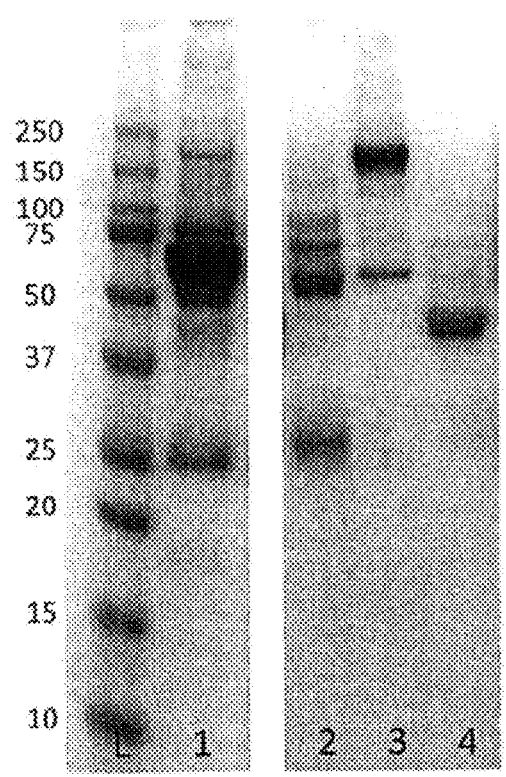
FIG. 22 shows the single, engineered Protein A domain fused to an optimized ELP can also be used to pull antibody out of complex mixtures, such as human serum. In this SDS-PAGE gel, the lanes are: L: ladder, 2: human serum albumin, 3: elution SN reduced, 4: elution SN not reduced, 5: elution pellet.

$ELP_{1,80}$-Cap was added to human serum to determine whether it could adequately pull down polyclonal antibodies of varied isotype from a complex mixture. The final elution supernatant was analyzed by SDS-PAGE in both reducing (antibody broken into heavy and light chain components) and non-reducing (antibody intact) conditions (FIG. 22). It demonstrates the ability to capture human antibodies from serum.

Figure 23:
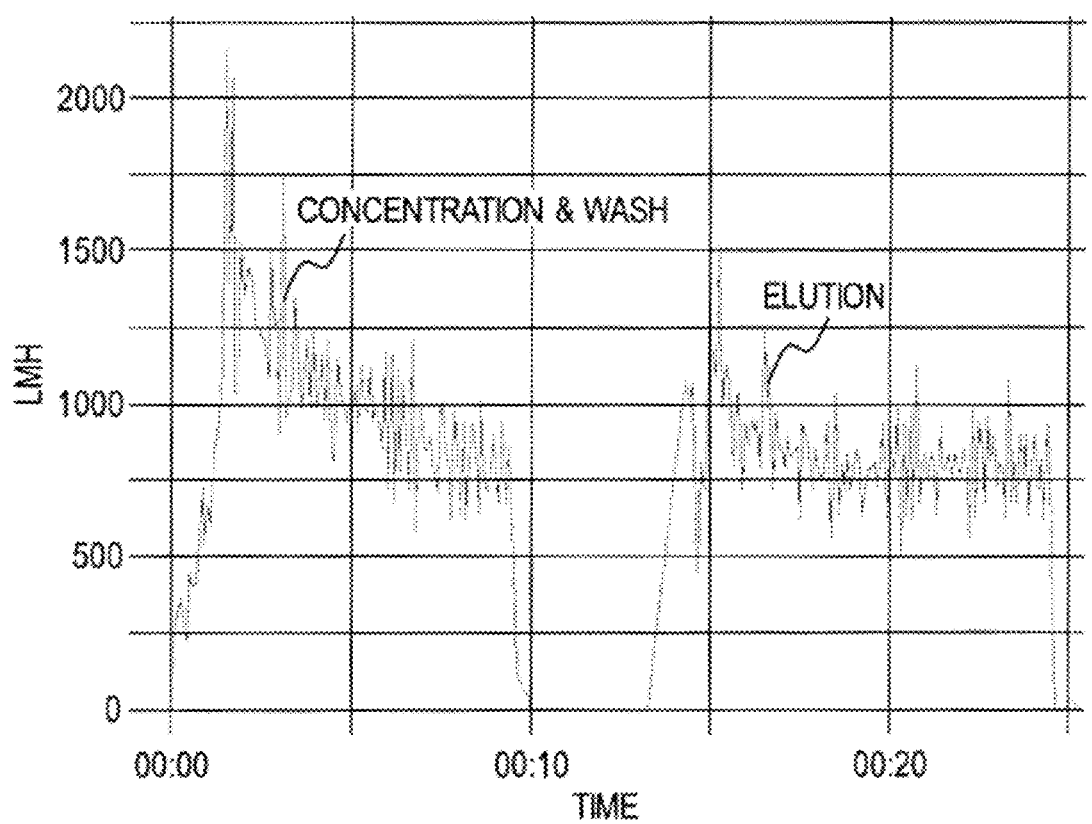
FIG. 23 shows antibody purification with optimized affinity/phase separation shows very high flux values of 750 liters per $m^2$ per hour (LMH) or more and rapid processing time of under 25 minutes from start to finish.
Figure 24:
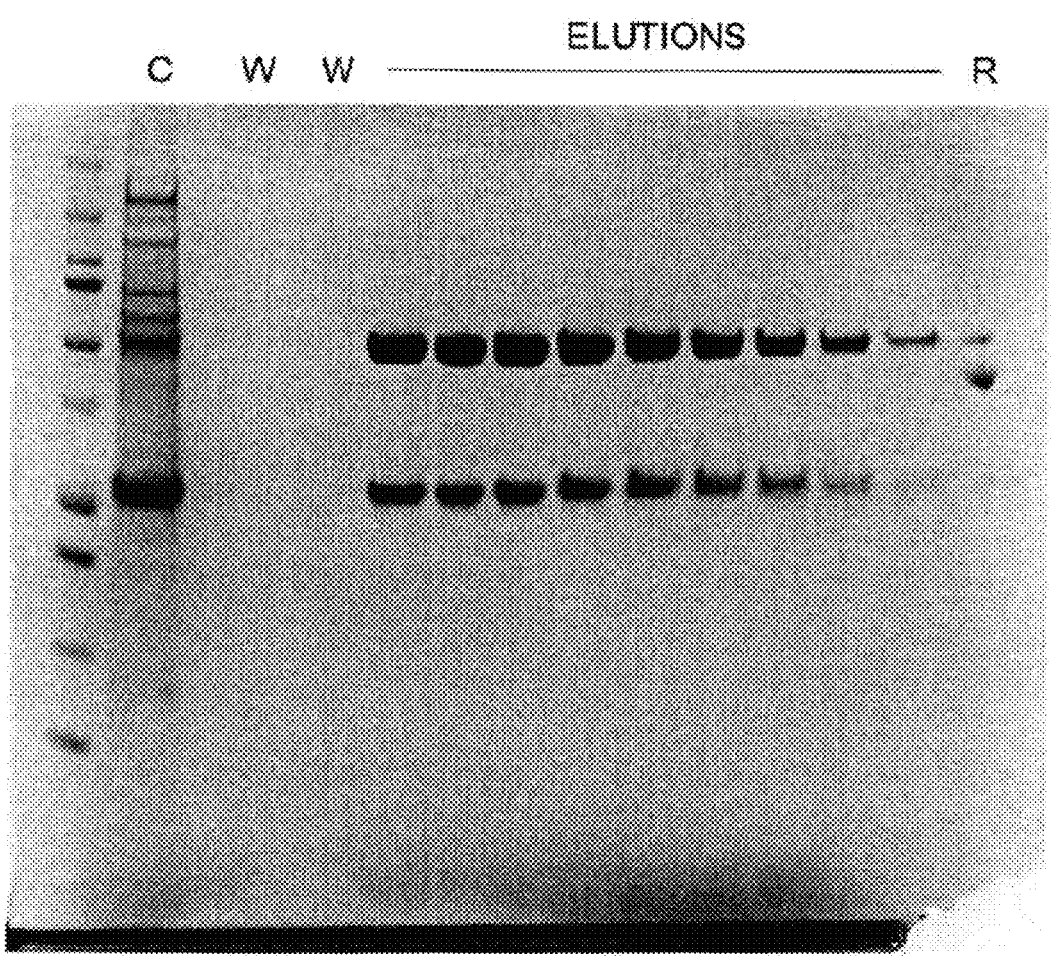
FIG. 24 shows SDS-PAGE gel of various fractions from the optimized TFF run using affinity/phase separation. Little to no antibody is lost during the concentration ("C") or wash ("W") steps, but the product is recovered during the elutions. Very little antibody remains in the retentate ("R") after the product has been eluted with low pH.

Clarified cell culture fluid with IgG1 titer of ~3.6 g/L was mixed with $ELP_{1,80}$-ZD. The optimized amount of salt need to trigger phase separation was added and the phase separation was left 20 minutes at room temperature to allow the particles to equilibrate in size. This mixture was then passed over a tangential flow filtration hollow fiber cartridge (0.2 μm pore size, polyethersulfone) with an area of 16 cm2. The sample was concentrated 4× and washed with 8 diavolumes (DVs) of wash buffer (0.6 M NaCl in PBS). The auxiliary pump was switched over to an elution buffer and the antibody was eluted with 5-10 DVs of 50 mM citrate, 0.6 M NaCl. Flux was monitored throughout this process (FIG. 23). Fractions collected throughout the process and visualized by Coomassie stain on SDS-PAGE show the removal of contaminants and a highly pure final antibody product (FIG. 24). Yields of eluted antibody were >90% and host cell protein contaminants were reduced by 3-log from the starting material (FIG. 23). ELP-Cap affinity/phase separation was performed on HEK cells transfected to produce AAV8 where the capsid contains the gene for a green fluorescent protein (GFP) reporter. AAV8 secreted from the HEK cells during culture was captured using an ELP-Cap$_{AAV}$ fusion protein for affinity/phase separation. AA V8 was purified from cell culture harvest containing AAV8-GFP with a titer of $7.1 \times 10^6$ viral genomes (vg) per μL. After adding ELP-Cap$_{AAV}$, the phase separation was triggered by adding 0.85 M NaCl and centrifuging at 37° C. and 10,000 ref for 5 minutes. The captured AAV8 was resuspended in 500 μL phosphate buffer and eluted with 500 μL of 100 mM sodium citrate buffer at pH 4.0 and a salt concentration of 0.6 M. The final, purified AAV8 had titers ranging from $2.26 \times 10^{10}$ to $3.44 \times 10^{10}$ vg. Titers were quantified using qPCR and the product was visually confirmed using SDS-PAGE (FIG. 26).

All publications, patent applications, patents, patent publications, sequences identified by GenBank® database accession numbers and other references cited herein are incorporated by reference in their entireties for the teachings relevant to the sentence and/or paragraph in which the reference is presented.

The foregoing is illustrative of the present invention, and is not to be construed as limiting thereof. The invention is defined by the following claims, with equivalents of the claims to be included therein.

What is claimed is:

1. A fusion protein comprising at least one capture domain and at least one elastin-like polypeptide (ELP), wherein the at least one capture domain binds to a polypeptide on the surface of a viral particle; wherein the at least one ELP comprises an amino acid sequence of (GVGVPGLGVPGVGVPGLGVPGVGVP)$_m$ (SEQ ID NO: 28), wherein m is an integer between 4 and 25.

2. The fusion protein of claim 1, wherein the at least one capture domain comprises an adeno-associated virus receptor (AAVR), or a domain thereof.

3. The fusion protein of claim 1, wherein the viral particle is an AAV particle.

4. The fusion protein of claim 1, comprising a second ELP.

5. The fusion protein of claim 1, comprising a spacer between the ELP and the capture domain.

6. The fusion protein of claim 1, wherein m is an integer of 16.

7. A method of purifying a viral particle comprising:
  (i) contacting the viral particle with the fusion protein of claim 1, wherein the viral particle binds the fusion protein to form a viral particle-bound fusion protein;
  (ii) triggering a phase transition to allow the viral particle-bound fusion protein to aggregate with one or more additional viral particle-bound fusion proteins;
  (iii) separating the viral particle-bound fusion protein from at least one contaminant; and
  (iv) separating the fusion protein from the viral particle.

8. A fusion protein comprising at least one capture domain and at least one elastin-like polypeptide (ELP), wherein the at least one capture domain binds to a polypeptide on the surface of a viral particle; wherein the at least one ELP comprises an amino acid sequence of (GVGVP)$_n$ (SEQ ID NO: 27) wherein n is an integer between 2 and 120.

9. The fusion protein of claim 8, comprising a second ELP.

10. The fusion protein of claim 8, comprising a spacer between the ELP and the capture domain.

11. The fusion protein of claim 8, wherein n is an integer of 80.

12. A method of purifying a viral particle comprising:
  (i) contacting the viral particle with the fusion protein of claim 8, wherein the particle binds the fusion protein to form a viral particle-bound fusion protein;
  (ii) triggering a phase transition to allow the viral particle-bound fusion protein to aggregate with one or more additional viral particle-bound fusion proteins;
  (iii) separating the viral particle-bound viral protein from at least one contaminant; and
  (iv) separating the fusion protein from the viral particle.

13. A polynucleotide encoding the fusion protein of claim 1.

14. A vector comprising the polynucleotide of claim 13.

15. A cell comprising the vector of claim 14.

16. A polynucleotide encoding the fusion protein of claim 8.

17. A vector comprising the polynucleotide of claim 16.

18. A cell comprising the vector of claim 17.

19. A method of purifying a biologic target, comprising:
  (i) contacting the biologic target with a fusion protein comprising an elastin-like polypeptide (ELP) and a capture domain, wherein the biologic target binds the fusion protein to form a biologic target-bound fusion protein;
  (ii) triggering a phase transition to allow the biologic target-bound fusion protein to aggregate with one or more additional biologic target-bound fusion proteins;
  (iii) separating the biologic target-bound fusion protein from at least one contaminant; and
  (iv) separating the fusion protein from the biologic target, wherein the biologic target is selected from any one of a polynucleotide, polysaccharide, cell, antibody, a non-viral vector, and a viral vector, wherein the viral vector is not an adenovirus or lentivirus vector.

20. A fusion protein comprising at least one capture domain and at least one elastin-like polypeptide (ELP), wherein the at least one capture domain binds to a polypeptide on the surface of a viral particle; wherein the at least one ELP comprises an amino acid sequence of (GVGVPGVGVPGAGVPGVGVPGVGVP)$_m$, wherein m is an integer from 4 to 25 (SEQ ID NO: 29).

21. The method of claim 7, wherein the viral particle is an AAV particle.

22. The fusion protein of claim 8, wherein the viral particle is an AAV particle.

23. The method of claim 12, wherein the viral particle is an AAV particle.

24. The fusion protein of claim 20, wherein the viral particle is an AAV particle.

25. The method of claim 19, wherein the biologic target is a polynucleotide.

26. The method of claim 19, wherein the biologic target is a cell.

27. The method of claim 19, wherein the biologic target is an antibody.

28. The method of claim 19, wherein the biologic target is a non-viral vector.

29. The method of claim 19, wherein the biologic target is a viral vector, wherein the viral vector is not an adenovirus or lentivirus vector.

30. The fusion protein of claim 20, comprising a second ELP.

31. The fusion protein of claim 20, comprising a spacer between the ELP and the capture domain.

32. The method of claim 19, wherein triggering a phase transition comprises introducing a salt to or heating a composition comprising the biologic target-bound fusion proteins.

33. The method of claim 19, wherein separating the biologic target-bound fusion protein from at least one contaminant comprises introducing a salt to a composition comprising the biologic target-bound fusion proteins, adjusting the ionic strength of a composition comprising the viral particle-bound fusion proteins, adjusting the pH of a composition comprising the viral particle-bound fusion proteins, or a combination thereof.

34. The method of claim 7, wherein triggering a phase transition comprises introducing a salt to or heating a composition comprising the biologic target-bound fusion proteins.

35. The method of claim 7, wherein separating the viral particle-bound fusion protein from at least one contaminant comprises introducing a salt to a composition comprising the biologic target-bound fusion proteins, adjusting the ionic strength of a composition comprising the viral particle-bound fusion proteins, adjusting the pH of a composition comprising the viral particle-bound fusion proteins, or a combination thereof.

36. The method of claim 12, wherein triggering a phase transition comprises introducing a salt to or heating a composition comprising the biologic target-bound fusion proteins.

37. The method of claim 12, wherein separating the viral particle-bound fusion protein from at least one contaminant comprises introducing a salt to a composition comprising the biologic target-bound fusion proteins, adjusting the ionic strength of a composition comprising the viral particle-bound fusion proteins, adjusting the pH of a composition comprising the viral particle-bound fusion proteins, or a combination thereof.

* * * * *